(12) United States Patent
Franklin et al.

(10) Patent No.: US 11,748,583 B2
(45) Date of Patent: Sep. 5, 2023

(54) NANOWIRE CHARACTERIZATION AND IDENTIFICATION

(71) Applicant: Regents of the University of Minnesota, Minneapolis, MN (US)

(72) Inventors: Rhonda R. Franklin, Falcon Heights, MN (US); Wen Zhou, Minneapolis, MN (US); Jaime F. Modiano, Minneapolis, MN (US); Bethanie J Stadler, Shoreview, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 17/810,155

(22) Filed: Jun. 30, 2022

(65) Prior Publication Data

US 2023/0026610 A1 Jan. 26, 2023

Related U.S. Application Data

(63) Continuation of application No. 16/151,206, filed on Oct. 3, 2018, now Pat. No. 11,379,677.

(Continued)

(51) Int. Cl.
*G01R 33/00* (2006.01)
*G06K 19/06* (2006.01)
(Continued)

(52) U.S. Cl.
CPC ........ *G06K 7/10366* (2013.01); *A61B 5/6852* (2013.01); *G01N 33/587* (2013.01);
(Continued)

(58) Field of Classification Search
CPC .......... G06K 7/10366; G06K 19/06187; A61B 5/6852; A61B 2562/0223; G01N 33/587;
(Continued)

(56) References Cited

U.S. PATENT DOCUMENTS

| 8,432,164 B2 * | 4/2013 | Kou | ..................... G01R 33/123 324/260 |
| 11,379,677 B2 | 7/2022 | Franklin et al. | |

(Continued)

OTHER PUBLICATIONS

Alonso et al., "FeCo nanowires with enhanced heating powers and controllable dimensions for magnetic hyperthermia," Journal of Applied Physics, vol. 117, No. 17, Jan. 2015, 4 pp.

(Continued)

*Primary Examiner* — Tuyen K Vo
(74) *Attorney, Agent, or Firm* — Shumaker & Sieffert, P.A.

(57) ABSTRACT

The techniques and systems described herein relate to manufacturing, characterizing, and/or identifying one or more types of magnetic nanowires (MNWs). One or more types of MNWs may be associated with different objects, and a system may identify the objects based on the magnetic nanowires associated with the objects. For example, such techniques may involve characterizing the types of MNWs based on magnetic field transmission characteristics and ferromagnetic resonance characteristics of each type of MNW. In some examples, the techniques described herein may enable the identification of each of a plurality of types of MNWs present in a sample or object based on a combined transmission value of the sample. Such techniques may enable the development and use of barcode-like systems of different types of MNWs for labeling and identifying objects of interest.

20 Claims, 30 Drawing Sheets

Related U.S. Application Data

(60) Provisional application No. 62/567,606, filed on Oct. 3, 2017.

(51) Int. Cl.
| | |
|---|---|
| *G06K 7/10* | (2006.01) |
| *G01N 33/58* | (2006.01) |
| *H01Q 1/14* | (2006.01) |
| *H01Q 1/38* | (2006.01) |
| *H01Q 15/00* | (2006.01) |
| *H01Q 19/00* | (2006.01) |
| *A61B 5/00* | (2006.01) |
| *G01R 33/04* | (2006.01) |

(52) U.S. Cl.
CPC .......... *G01R 33/0011* (2013.01); *G01R 33/04* (2013.01); *G06K 19/06187* (2013.01); *H01Q 1/14* (2013.01); *H01Q 1/38* (2013.01); *H01Q 15/006* (2013.01); *H01Q 19/005* (2013.01); *A61B 2562/0223* (2013.01)

(58) Field of Classification Search
CPC ...... G01R 33/0011; G01R 33/04; H01Q 1/14; H01Q 1/38; H01Q 15/006; H01Q 19/005
See application file for complete search history.

(56) References Cited

U.S. PATENT DOCUMENTS

| | | | | |
|---|---|---|---|---|
| 2004/0100278 | A1* | 5/2004 | Haycock | G01R 33/60 324/637 |
| 2011/0080241 | A1 | 4/2011 | Kou et al. | |
| 2015/0085569 | A1 | 3/2015 | Nozaki et al. | |
| 2016/0377575 | A1* | 12/2016 | Chieh | A61B 5/05 324/224 |
| 2018/0105866 | A1* | 4/2018 | Modiano | G16B 5/00 |
| 2018/0267128 | A1* | 9/2018 | Guisan | G01R 31/318511 |
| 2019/0051821 | A1* | 2/2019 | Yoon | H10N 50/85 |

OTHER PUBLICATIONS

Altanerova et al., "Exosomes of human mesenchymal stem/stromal/medicinal signaling cells," MSC Exosomes, Neoplasma, Aug. 16, 2017, 7 pp.

Altman et al., "Unmet needs: Research helps regulators do their jobs," Science Translational Medicine, vol. 7, No. 315, Nov. 2015, 8 pp.

Anderson et al., "Melanoma cell resistance to phagocytosis is unrelated to expression of conventional "eat me/don't eat-me" signals," Cancer Immunology Research, vol. 4, Abstract A143, Jan. 2016, 2 pp.

Angstadt et al., "Characterization of Canine Osteosarcoma by Array Comparative Genomic Hybridization and RT-qPCR: Signatures of Genomic Imbalance in Canine Osteosarcoma Parallel the Human Counterpart," Genes, Chromosomes & Cancer, Wiley Online Library, Aug. 11, 2011, 16 pp.

Angstadt et al., "A genome-wide approach to comparative oncology: high-resolution oligonucleotide aCGH of canine and human osteosarcoma pinpoints shared Microaberrations," Cancer Genetics, Elsevier, Sep. 24, 2012, 16 pp.

Arras et al., "Assessment of post-laparotomy pain in laboratory mice by telemetric recording of heart rate and heart rate variability," BMC Veterinary Research, Aug. 2, 2007, 10 pp.

Atay et al., "Oncogenic KIT-containing exosomes increase gastrointestinal stromal tumor cell invasion," Cell Biology, PNAS, Dec. 3, 2013, 6 pp.

Azevedo et al., "Circulating Microparticles as Therapeutic Targets in Cardiovascular Diseases," Bentham Science Publishers Ltd., Feb. 2007, 11 pp.

Baglio et al., "Human bone marrow- and adipose- mesenchymal stem cells secrete exosomes enriched in distinctive miRNA and tRNA species," Stem Cell Research and Therapy, Jul. 1, 2015, 20 pp.

Banerjee et al., "CD133+ tumor initiating cells (TIC) in a syngenic murine model of pancreatic cancer respond to Minnelide," Clinical Cancer Research, May 1, 2014, 22 pp.

Becker et al., "Extracellular Vesicles in Cancer: Cell-to-Cell Mediators of Metastasis," Cancer Cell, vol. 30, No. 6, Dec. 2016, 26 pp.

Beleggia et al., "Demagnetization factors of the general ellipsoid: An alternative to the Maxwell approach," Philosophical Magazine, vol. 86, No. 16, Jun. 2006, 16 pp.

Berganza et al., "Multisegmented Nanowires: A Step towards the Control of the Domain Wall Configuration," Scientific Reports, vol. 7, No. 1, Sep. 2017, 8 pp.

Biehl et al., "Synthesis, Characterization, and Applications of Magnetic Nanoparticles Featuring Polyzwitterionic Coatings," Polymers (Basel), vol. 10, No. 1, Jan. 2018, 28 pp.

Bielack et al., "Prognostic Factors in High-Grade Osteosarcoma of the Extremities or Trunk: An Analysis of 1,702 Patients Treated on Neoadjuvant Cooperative Osteosarcoma Study Group Protocols," Journal of Clinical Oncology, vol. 20, No. 3, Feb. 1, 2002, 16 pp.

Bolger et al., "Trimmomatic: a flexible trimmer for Illumina sequence data," Bioinformatics, vol. 30, Apr. 1, 2014, 7 pp.

Bran et al., "Co/Au multisegmented nanowires: a 3D array of magnetostatically coupled nanopillars," Nanotechnology, vol. 28, No. 9, Mar. 2017, 7 pp.

Broner et al., "TSAP6 is a novel candidate marker for poor survival in metastatic high-grade serous carcinoma," Human Pathology, Elsevier, Oct. 10, 2016, 180-187 pp.

Brune et al., "Mesenchymal stromal cells from primary osteosarcoma are non-malignant and strikingly similar to their bone marrow counterparts," UICC, International Journal of Cancer, Sep. 28, 2010, 13 pp.

Buford et al., "A technique for error estimation of linewidth and damping parameters extracted from ferromagnetic resonance measurements," Journal of Applied Physics, vol. 117, No. 17, Feb. 2015, 4 pp.

Camussi et al., "Tumor-Derived Microvesicles and the Cancer Microenvironment," Current Molecular Medicine, vol. 13, No. 1, Jan. 2013, 10 pp.

Caswell et al., "Obligate Progression Precedes Lung Adenocarcinoma Dissemination," Cancer Discovery, Research Brief, Apr. 16, 2014, 10 pp.

Chaffee et al., "A Clinically Relevant Mouse Model of Canine Osteosarcoma with Spontaneous Metastasis,"' In Vivo, Sep. 2013, 5 pp.

Chaput et al., "Exosomes" immune properties and potential clinical implementations, Seminars in Immunopathology, vol. 33, No. 5, Sep. 2011, 22 pp.

Chuen Choi et al., "Lessons from patient-derived xenografts for better in vitro modeling of Human cancer," Advanced Drug Delivery Reviews, Elsevier, Oct. 2014, 16 pp.

Contreras et al., "Targeted cancer cell death induced by biofunctionalized magnetic nanowires," 2 nd Middle East Conference on Biomedical Engineering, Feb. 2014, 4 pp.

Coomer et al., Development of an intramuscular xenograft model of canine osteosarcoma in mice for evaluation of the effects of radiation therapy, American Journal of Veterinary Res., vol. 70, No. 1, Jan. 2009, 7 pp.

Corcoran et al., "miR-34a is an Intracellular and Exosomal Predictive Biomarker for Response to Docetaxel with Clinical Relevance to Prostate Cancer Progression," The Prostate 74, accepted Jun. 5, 2014, 1320-1334 pp.

Corrado et al., "Chronic myelogenous leukemia exosomes modulate bone marrow microenvironmental through activation of epidermal growth factor receptor," J. Cell. Mol. Med. vol. 20, No. 10, Mar. 8, 2016, 1829-1839 pp.

Creighton et al., "Profiling of pathway-specific changes in gene expression following growth of human cancer cell lines transplanted into mice," Genome Biology, Jun. 23, 2003, 12 pp.

D'Asti et al., "Extracellular Vesicles in Brain Tumor Progression," Cell Mol Neurobiology, Review Paper, Oct. 24, 2015, 25 pp.

(56) References Cited

OTHER PUBLICATIONS

Daniel et al., "A Primary Xenograft Model of Small-Cell Lung Cancer Reveals Irreversible Changes in Gene Expression Imposed by Culture In vitro," American Association for Cancer Research, Apr. 15, 2009, 11 pp.

Delitto et al., "Patient-Derived Xenograft Models for Pancreatic Adenocarcinoma Demonstrate Retention of Tumor Morphology through Incorporation of Murine Stromal Elements," The American Journal of Pathology, vol. 185, No. 5, May 2015, 7 pp.

Dodd et al., "Myogenic transcription factors regular pro-metastatic miR-182," Oncogene, Apr. 7, 2016, 18 pp.

Donahue et al., "OOMMF User's Guide, Version 1.0," Interagency Report NISTIR 6376, national Institute of Standards and Technology, Sep. 1999, 92 pp.

Egas-Bejar et al., "Theranostic profiling for actionable aberrations in advanced high risk osteosarcoma with aggressive biology reveals high molecular diversity: the human fingerprint hypothesis," Oncoscience, vol. 1, No. 2, Mar. 12, 2014, 13 pp.

Ekstrom et al., "WNT5A induces release of exosomes containing pro-angiogenic and immunosuppressive factors from malignant melanoma cells," Molecular Cancer, 2014 (Applicant points out, in accordance with MPEP 609.04(a), that the year of publication, 2014, is sufficiently earlier than the effective U.S. filing date, so that the particular month of publication is not in issue.), 15 pp.

El-Saghir et al., "ATL-derived exosomes modulate mesenchymal stem cells; potential role in leukemia progression," Retrovirology, Oct. 19, 2016, 13 pp.

Encinas-Oropesa et al., "Dipolar interactions in arrays of nickel nanowires studied by ferromagnetic resonance," Physical Review B, vol. 63, No. 10, Feb. 2001, 6 pp.

Fan et al., "Comparative Aspects of Osteosarcoma Pathogenesis in Humans and Dogs," Veterinary Sciences, Aug. 17, 2015, 21 pp.

Farahani et al., "CLL Exosomes Modulate the Transcriptome and Behavior of Recipient Stromal Cells and are Selectively Enriched in miR-202-3p," PLOS One, Oct. 28, 2015, 18 pp.

Faraji et al., "Magnetic nanoparticles: Synthesis, stabilization, functionalization, characterization, and applications," Journal of the Iranian Chemical Society, vol. 7, No. 1, Mar. 2010, 37 pp.

Fei et al., "B-cell precursor acute lymphoblastic leukemia and stromal cells communicate through Galectin-3," Oncotarget, vol. 6, No. 13, Mar. 30, 2015, 17 pp.

Fenger et al., "Canine Osteosarcoma: A Naturally Occurring Disease to Inform Pediatric Oncology," ILAR Journal, vol. 55, No. 1, Apr. 1, 2014, 17 pp.

Fritz et al., "A phase I clinical study to evaluate safety of orally administered, genetically engineered *Salmonella enterica* serovar Typhimurium for canine osteosarcoma," Veterinary Medicine and Science, Wiley & Sons Ltd., Jun. 6, 2016, 12 pp.

Fujita et al., "Extracellular vesicle transfer of cancer pathogenic components," Cancer Science Article Review, Jan. 18, 2016, 6 pp.

Garimella et al., "Biological characterization of preclinical Bioluminescent Osteosarcoma Orthotopic Mouse (BOOM) model: A multi-modality approach," Journal of Bone Oncology, Elsevier, Dec. 31, 2012, 11 pp.

Goldvaser et al., "Characterisation of blood-derived exosomal hTERT mRNA secretion in cancer patients: a potential pan-cancer marker," British Journal of Cancer, May 16, 2017, 5 pp.

Gopal et al., "Extracellular vesicles: their role in cancer biology and epithelial-mesenchymal transition," Biochemical journal, Oct. 10, 2016, 25 pp.

Gordon et al., " Identification of Three Molecular and Functional Subtypes in Canine Hemangiosarcoma through Gene Expression Profiling and Progenitor Cell Characterization," The American Journal of Pathology, Elsevier, Dec. 16, 2013, 11 pp.

Guo et al., "Exosomes: New players in cancer (Review)," Oncology Reports, May 29, 2017, 11 pp.

Guowei et al., "Research Progress of Mechanism of mesenchymal Stem Cells-Derived Exosomes in Tissue Repair," Chinese Journal of Reparative and Reconstructive Surgery, Translation provided for the Abstract Only, vol. 30, Apr. 2016, 6 pp.

Hannafon et al., "Plasma exosome microRNAs are indicative of breast cancer," CrossMark, BioMed Central, Breast Cancer Research, vol. 18, No. 90, DOI 10.1186/s13058-016-0753-x, Sep. 2016, 14 pp.

He et al., "Progressive epithelial to mesenchymal transitions in ARCaPE prostate cancer cells during xenograft tumor formation and metastasis," NIH Public Access, Apr. 1, 2010, 17 pp.

Hollingshead et al., "Gene expression profiling of 49 human tumor xenografts from in vitro culture through multiple in vivo passages—strategies for data mining in support of therapeutic studies," BMC Genomics, May 22, 2014, 16 pp.

Hood et al., "Exosomes Released by Melanoma Cells Prepare Sentinel Lymph Nodes for Tumor Metastasis," Cancer Research, Jun. 2011, 21 pp.

Huang et al., "Downregulation of estrogen receptor and modulation of growth of breast cancer cell lines mediated by paracrine stromal cell signals," Breast Cancer Res. Treat, HHS Public Access, first published Jan. 2017, 25 pp.

Hultgren et al., "Optimization of Yield in Magnetic Cell Separations Using Nickel Nanowires of Different Lengths," Biotechnology Process, vol. 21, No. 2, Mar. 2005, 7 pp.

Jaffe, "Historical Perspective on the Introduction and Use of Chemotherapy for the Treatment of Osteosarcoma," Current Advances in Osteosarcoma, Advances in Experimental Medicine and Biology, May 2, 2014, 30 pp.

Jain, "Applications of Nanobiotechnology in Clinical Diagnostics," Clinical Chemistry, Vo. 53, No. 11, Aug. 2007, 8 pp.

Jareonsong et al., "Effects of transplantation sites on tumour growth, pulmonary metastasis and ezrin expression of canine osteosarcoma cell lines in nude mice," Veterinary and Comparative Oncology, Blackwell Publishing Ltd, Sep. 9, 2011, 9 pp.

Javeed et al., "Exosomes and their role in the micro-/macroenvironment: a comprehensive review," Journal of Biomedical Research, vol. 31, No. 5, Sep. 2017, 9 pp.

Jiang et al., "Expression of ERCC1, TYMS, RRM1, TUBB3, and non-muscle myosin II, myoglobin and MyoD1 in lung adenocarcinoma pleural effusions predicts survival in patients receiving platinum-based chemotherapy," Molecular Medicine Reports, Spandidos Publications, Dec. 30, 2014, 12 pp.

Johann et al., "Tumour stromal cells derived from paediatric malignancies display MSC-like properties and impair NK cell cytotoxicity," BioMed Central, Sep. 21, 2010, 10 pp.

Jokerst et al., "Nanoparticle PEGylation for imaging and therapy," Nanomedicine (Lond), vol. 6, No. 4, Jun. 2011, 27 pp.

Kalluri, "The biology and function of exosomes in cancer," Journal of Clinical Investigation, vol. 126, No. 4, Apr. 2016, 8 pp.

Kanaya et al., "Anti-Tumor Effect of Adenoviral Vector-Mediated p53 Gene Transfer on the Growth of Canine Osteosarcoma Xenografts in Nude Mice," Internal Medicine, J. Vet. Med. Sci, published online, Feb. 22, 2011, 7 pp.

Kang et al., "Dissecting Tumor-Stromal Interactions in Breast Cancer Bone Metastasis," Endocrinology and Metabolism, Korean Endocrine Society, May 13, 2016, 7 pp.

Kansara et al., "Molecular Pathogenesis of Osteosarcoma," Review Paper, DNA and Cell Biology, vol. 26, No. 1, Jan. 31, 2007, 18 pp.

Kartopu et al., "Size effects and origin of easy-axis in nickel nanowire arrays," Journal of Applied Physics, vol. 109, No. 3, Feb. 2011, 8 pp.

Kawada et al., "Small molecules modulating tumor-stromal cell interactions: new candidates for anti-tumor drugs," The Journal of Antibiotics, Mar. 23, 2016, 4 pp.

Kawamoto et al., "Tumor-Derived Microvesicles Induce Proangiogenic Phenotype in Endothelial Cells via Endocytosis," PLOS One, Mar. 30, 2012, 11 pp.

Kim et al., "HISAT: a fast spliced aligner with low memory requirements," Nat Methods, Apr. 2015, 17 pp.

Kim et al., "Interleukin-8 Promotes Canine Hemangiosarcoma Growth by Regulating the Tumor Microenvironment," Exp. Cell Research, Apr. 15, 2014, 19 pp.

Kucharzewska et al., "Exosomes reflect the hypoxic status of glioma cells and mediate hypoxia-dependent activation of vascular cells during tumor development," PNAS, vol. 110, No. 18, Apr. 30, 2013, 6 pp.

(56) References Cited

OTHER PUBLICATIONS

Kuijjer et al., "mRNA expression profiles of primary high-grade central osteosarcoma are preserved in cell lines and xenografts," BMC Medical Genomics, Sep. 20, 2011, 12 pp.

Landau et al., "On the theory of the dispersion of magnetic permeability in ferromagnetic bodies," Phys. Zeitsch. der Sowjetunion, vol. 8, Jan. 1935, 9 pp.

Laszlo et al., "High expression of myocyte enhancer factor 2C (MEF2C) is associated with adverserisk features and poor outcome in pediatric acute myeloid leukemia: a report from the Children's Oncology Group," Journal of Hematology & Oncology, Oct. 20, 2015, 10 pp.

Lauvrak et al., "Functional characterisation of osteosarcoma cell lines and identification of mRNAs and miRNAs associated with aggressive cancer phenotypes," British Journal of Cancer, published online Sep. 24, 2013, 9 pp.

Lee et al., "Microvesicles as mediators of intercellular communication in cancer—the emerging science of cellular 'debris'," Semin Immunopathology, Jan. 13, 2011, 455-467 pp.

Li et al., "Exosome-mediated transfer of lncRUNX2-AS1 from multiple myeloma cells to MSCs contributes to osteogenesis," Oncogene, May 14, 2018, 12 pp.

Li et al., "Lung tumor exosomes induce a pro-inflammatory phenotype in mesenchymal stem cells via NFkB-TLR signaling pathway," Journal of Hematology & Oncology, Apr. 18, 2016, 12 pp.

Li et al., "The Sequence Alignment/Map format and SAMtools," Bioinformatics Applications Note, vol. 25, May 30, 2009, 2 pp.

Liao et al., "featureCounts: an efficient general purpose program for assigning sequence reads to genomic features," Bioinformatics, vol. 30, Nov. 7, 2013, 8 pp.

Lopatina et al., "Cross Talk between Cancer and Mesenchymal Stem Cells through Extracellular Vesicles Carrying Nucleic Acids," Frontiers in Oncology, vol. 6, Article 125, May 23, 2016, 11 pp.

Lou et al., "Exosomes derived from MiR-122-modified adipose tissue-derived MSCs increase chemosensitivity of hepatocellular carcinoma," Journal of Hematology & Oncology, Oct. 29, 2015, 11 pp.

Lu et al., "Exosomal miR-9 inhibits angiogenesis by targeting MDK and regulating PDK/AKT pathway in nasopharyngeal carcinoma," Journal of Experimental & Clinical Cancer Research, Jun. 26, 2018, 12 pp.

Martin et al., "The Genetics of Osteosarcoma," Review Article, Hindawi Publishing Corporation, vol. 2012, accepted Jan. 31, 2012, 12 pp.

Martins et al., "Tumor-cell-derived microvesicles as carriers of molecular information in cancer," Current Opinion, vol. 25, No. 1, Jan. 2013, 10 pp.

Mayordomo et al., "A Tissue Microarray Study of Osteosarcoma: Histopathologic and Immunohistochemical Validation of Xenotransplanted Tumors as Preclinical Models," Research Article, Applied Immununohistochemical Mol. Morphol. Feb. 24, 2010, 9 pp.

McIntyre et al., "Mouse models of colorectal cancer as preclinical models," Prospects & Overviews, Jun. 26, 2015, 12 pp.

Melzer et al., "Concise Review: Crosstalk of Mesenchymal Stroma/Stem-Like Cells with Cancer Cells Provides Therapeutic Potential," Stem Cells, Mar. 19, 2018, 18 pp.

Milane et al., "Exosome mediated communication within the tumor microenvironment," Elsevier, Science Direct, Journal of Controlled Release, vol. 219, Jul. 2, 2015, pp. 278-294.

Mintz et al., "An Expression Signature Classifies Chemotherapy-Resistant Pediatric Osteosarcoma," Cancer Research Article, Mar. 1, 2005, 8 pp.

Mirabello et al., "Osteosarcoma incidence and survival rates from 1973 to 2004: Data from the Surveillance, Epidemiology, and End Results Program," Cancer, National Institute of Health, Apr. 1, 2009, 18 pp.

Mirzaei et al., "Diagnostic and Therapeutic Potential of Exosomes in Cancer: The Beginning of a New Tale?" Journal of Cellular Physiology, vol. 232, No. 12, Dec. 2017, 10 pp.

Modiano et al., "Inflammation, Apoptosis, and Necrosis Induced by Neoadjuvant Fas Ligand Gene Therapy Improves Survival of Dogs With Spontaneous Bone Cancer," The American Society of Gene & Cell Therapy, Jun. 30, 2012, 10 pp.

Modiano et al., "Mesenchymal stromal cells inhibit murine syngeneic anti-tumor immune responses by attenuating inflammation and reorganizing the tumor microenvironment," Cancer Immunol Immunother, vol. 64, No. 11, Nov. 2015, 21 pp.

Mohseny et al., "Functional characterization of osteosarcoma cell lines provides representative models to study the human disease," Laboratory Investigation, Apr. 25, 2011, 11 pp.

Mohseny et al., "Osteosarcoma Models: From Cell Lines to Zebrafish," Review Article, Hindawi Publishing Corporation, Nov. 24, 2011, 12 pp.

Morello et al., "Biology, diagnosis and treatment of canine appendicular osteosarcoma: Similarities and differences with human osteosarcoma," The Veterinary Journal, Aug. 28, 2010, 10 pp.

Moriarity et al., "A Sleeping Beauty forward genetic screen identifies new genes and pathways driving osteosarcoma development and metastasis," Nat Genet, Jun. 2015, 30 pp.

Muller et al., "Exosomes isolated from plasma of glioma patients enrolled in a vaccination trial reflect antitumor immune activity and might predict survival," OncoImmunology, Jan. 2015, 8 pp.

Muntion et al., "Microvesicles from Mesenchymal Stromal Cells are Involved in HPCMicroenvironment Crosstalk in Myelodysplastic Patients," PLOS One, Feb. 2, 2016, 20 pp.

Nazarenko et al., "Exosomes as Potential Tool for a Specific Delivery of Functional Molecules," Chapter 37, Ovarian Cancer, ISBN: 978-1-62703-546-0, 2013, (Applicant points out, in accordance with MPEP 609.04(a), that the year of publication, 2013, is sufficiently earlier than the effective U.S. filing date, so that the particular month of publication is not in issue.).

Nemati et al., "Exosome enrichment in Blood Biopsies via Radio-Frequency Identification (RFID) Nanowire Tags," Poster presented at Upper-Midwest Agricultural Safety and Health Center, Oct. 3, 2017, 1 pp.

O'Donoghue et al., "Expression profiling in canine osteosarcoma: identification of biomarkers and pathways associated with outcome," BioMed Central, Sep. 22, 2010, 16 pp.

Ohyashiki et al., "Exosomes promote bone marrow angiogenesis in hematologic neoplasia: the role of hypoxia," Co-Hematology, vol. 23, No. 3, Wolters Kluwer Health, Inc., May 2016, 6 pp.

Pacharinsak et al., "Animal Models of Cancer Pain," Comparative Medicine, vol. 58, No. 3, Jun. 2008, 14 pp.

Pando et al., "Extracellular vesicles in leukemia," Leukemia Research, Elsevier, Nov. 21, 2017, 9 pp.

Piraux et al., "Template-grown NiFe/Cu/NiFe nanowires for spin transfer devices," Nano Letters, vol. 7 No. 9, Aug. 2007, 5 pp.

Pondman et al., "Magnetic drug delivery with FePd nanowires," Journal of Magnetism and Magnetic Materials, vol. 380, Apr. 2015, 8 pp.

Prosecution History from U.S. Appl. No. 16/151,206, dated Nov. 7, 2018 through Mar. 1, 2022, 12 pp.

Rana et al., "Exosomal Tumor MicroRNA Modulates Premetastatic Organ Cells," NeoPlasia, vol. 15, No. 3, Mar. 2013, 281-295 pp.

Record et al., "Exosomes as intercellular signalosomes and pharmacological effectors," HAL, Apr. 22, 2012, 20 pp.

Robinson et al., "edgeR: a Bioconductor package for differential expression analysis of digital gene expression data," Bioinformatics, vol. 26, No. 1, Nov. 11, 2009, 2 pp.

Rossi et al., "The Role of Extracellular Vesicles in Bone Metastasis," International Journal of Molecular Sciences, vol. 19, No. 4, Apr. 10, 2018, 13 pp.

Sampson et al., "Xenograft and genetically engineered mouse model systems of osteosarcoma and Ewing's sarcoma: tumor models for cancer drug discovery," Expert Opinion Drug Discovery, Oct. 2013, 16 pp.

Santi et al., "Cancer associated fibroblasts transfer lipids and proteins to cancer cells through cargo vesicles supporting tumor growth," Biochimica et Biophysica Acta, Elsevier, Sep. 11, 2015, 13 pp.

(56) References Cited

OTHER PUBLICATIONS

Sarver et al., "MicroRNAs at the human 14q32 locus have prognostic significance in osteosarcoma," Orphanet Journal of Rare Diseases, Jan. 11, 2013, 11 pp.
Schageman et al., "The Complete Exosome Workflow Solution: From Isolation to Characterization of RNA Cargo," Research Gate, Hindawi Publishing Corporation, vol. 2013, Article 253957, DOI: 10.1155/2013/253957, Sep. 2013, 17 pp.
Scott et al., "Heterotypic mouse models of canine osteosarcoma recapitulate tumor heterogeneity and biological behavior," Disease Models & Mechanisms, The Company of Biologists, Sep. 23, 2016, 10 pp.
Scott et al., "Molecular subtypes of osteosarcoma identified by reducing tumor heterogeneity through an interspecies comparative approach," Bone, Sep. 2011, 26 pp.
Scott et al., "Aberrant Retinoblastoma (RB)-E2F Transcriptional Regulation Defines Molecular Phenotypes of Osteosarcoma," The Journal of Biological Chemistry, vol. 290, No. 47, Published Sep. 16, 2015, 14 pp.
Scott et al., "Characterization of RNA in osteosarcoma-derived exosomes," Proceedings of the Keystone Symposia Exosomes/Microvesicles: Novel Mechanisms of Cell-Cell Communication, Abstract, Jun. 2016, 1 pp.
Scott et al., "Role of osteosarcoma-derived exosomes in interactions with stromal environment and metastasis," University of Minnesota—College of Veterinary Medicine, E4, poster 2050, Jun. 2016, 1 pp.
Scott et al., Unbiased Discovery of Exosome-Associated Biomarkers Using Xenograft Models, Poster 817 presented Jun. 21, 2016, University of Minnesota, 1 pp.
Shao et al., "Chip-based analysis of exosomal mRNA mediating drug resistance in glioblastoma," Nature Communications, May 11, 2015, 9 pp.
Sharma et al., "Alignment of collagen matrices using magnetic nanowires and magnetic barcode readout using first order reversal curves (FORC) (invited)," Journal of Magnetism and Magnetic Materials, vol. 459, Aug. 2018, 6 pp.
Sharma et al., "FMR Measurements of Magnetic Nanostructures," Ferromagnetic Resonance—Theory and Applications, Chapter 4, Jul. 2013, 18 pp.
Sharma et al., "Inducing cells to disperse nickel nanowires via integrin-mediated responses," Nanotechnology, vol. 26, No. 13, Mar. 2015, 12 pp.
Sharma et al., "Magnetic Barcode Nanowires for Osteosarcoma Cell Control, Detection and Separations," IEEE Transactions on Magnetics, vol. 49, No. 1, Jan. 2013, 4 pp.
Sharma et al., "Tumor exosomes: cellular postmen of cancer diagnosis and personalized therapy," Nanomedicine (Lond.), vol. 11, No. 4, Feb. 2016, 17 pp.
Shin et al., "Changes in the biological characteristics of glioma cancer stem cells after serial in vivo subtransplantation," Childs Nerve System, Springer Online, published online Nov. 10, 2012, 10 pp.
Shore et al., "Electrodeposited Fe and Fe—Au nanowires as MRI Contrast Agents," Chemical Communications, vol. 52, Sep. 2016, 4 pp.
Sievers et al., "Microwave Interferometry for High Sensitivity VNA-FMR Measurements," IEEE Transactions on Magnetics, vol. 53, No. 4, Apr. 2017, 4 pp.
Siravegna et al., "Integrating liquid biopsies into the management of cancer," Nature Reviews Clinical Oncology, vol. 14, Mar. 2017, 18 pp.
Sleeman, "The metastatic niche and stromal progression," Cancer Metastasis Review, published online Jun. 15, 2012, Springer Link, 12 pp.
Sokolov et al., "Single-Point FMR Linewidth Measurement by TE10 Rectangular Transmission Cavity Perturbation," IEEE Transactions on Microwave Theory and Techniques, vol. 64, No. 11, Nov. 2016, 9 pp.
Soldevilla et al., "Tumor-derived exosomes are enriched in ?Np73, which promotes oncogenic potential in acceptor cells and correlates with patient survival," Human Molecular Genetics, vol. 23, No. 2, Sep. 18, 2013, 467-478 pp.
Sottnik et al., "Induction of VEGF by tepoxalin does not lead to increased tumour growth in a canine osteosarcoma xenograft," Vet Comparative Oncology, Blackwell Publishing Ltd, Sep. 13, 2010, 13 pp.
Steinbichler et al., "The Role of Exosomes in Cancer Metastasis," Seminars in Cancer Biology, vol. 44, Jun. 2017, 12 pp.
Syn et al., "Evolving landscape of tumor molecular profiling for personalized cancer therapy: a comprehensive review," Expert Opinion on Drug Metabolism & Toxicology, vol. 12, No. 8, Jun. 2016, 12 pp.
Takeshita et al., "Serum microRNA expression profile: miR-1246 as a novel diagnostic and prognostic biomarker for oesophageal squamous cell carcinoma," British Journal of Cancer, Jan. 29, 2013, 9 pp.
Talmadge et al., "Murine Models to Evaluate Novel and Conventional Therapeutic Strategies for Cancer," The American Journal of Pathology, vol. 70, No. 3, Mar. 2007, 12 pp.
Tamburini et al., "Gene Expression Profiles of Sporadic Canine Hemangiosarcoma are Uniquely Associated with Breed," PLOS One, vol. 4, Issue 5, May 20, 2009, 12 pp.
Tan et al., "Osteosarcoma—conventional treatment vs. gene therapy," Cancer Biology & Therapy, published online, Jan. 15, 2009, 12 pp.
Thayanithy et al., "Perturbation of 14q32 miRNAs-cMYC gene network in osteosarcoma," Bone, Jan. 2012, 25 pp.
Tutar, "miRNA and Cancer; Computational and Experimental Approaches," Current Pharmaceutical Biotechnology, vol. 15, No. 5, May 2014, 1 pp.
Um et al., "RFID Biomarkers Using Nanowires," MINT Poster, Oct. 2017, 1 pp.
Valcz et al., "Exosomes in colorectal carcinoma formation: ALIX under the magnifying glass," Modern Pathology, published online May 6, 2016, 11 pp.
Valenzuela et al., "Magnetoimpedance, ferromagnetic resonance, and low field microwave absorption in amorphous ferromagnets," Journal of Non-Crystalline Solids, vol. 353, Nos. 8-10, Apr. 2007, 5 pp.
Van Deun et al., "The impact of disparate isolation methods for extracellular vesicles on downstream RNA profiling," Journal of Extracellular Vesicles, Sep. 18, 2014, 14 pp.
Varshney et al., "Understanding the Osteosarcoma Pathobiology: A Comparative Oncology Approach," Veterinary Sciences, MDPI, Jan. 18, 2016, 15 pp.
Wang et al., "Effector T Cells Abrogate Stroma-Mediated Chemoresistance in Ovarian Cancer," Cell, May 19, 2016, 28 pp.
Wang et al., "Lung cancer exosomes initiate global long non-coding RNA changes in mesenchymal stem cells," International Journal of Oncology, Nov. 11, 2015, 681-689 pp.
Whiteside, "Exosome and mesenchymal stem cell cross-talk in the tumor microenvironment," Seminars in Immunology, Elsevier, Dec. 8, 2017, 11 pp.
Whiteside, "Tumor-Derived Exosomes and Their Role in Cancer Progression," Advances in Clinical Chemistry, vol. 74, Apr. 2016, 35 pp.
Withrow et al., "Comparative Aspects of Osteosarcoma," Clinical Orthopaedics and Related Research, Nov. 29, 1990, 10 pp.
Wolfe et al., "Effect of zoledronic acid and amputation on bone invasion and lung metastasis of canine osteosarcoma in nude mice," Clin Exp Metastasis, Apr. 2011, 27 pp.
Xi et al., "Inter- and intra-nanowire magnetic interaction in Co/Cu multilayer nanowires deposited by electrochemical deposition," Physica B: Condensed Matter, vol. 518, Aug. 2017, 4 pp.
Xu et al., "Serum exosomal hnRNPH1 mRNA as a novel marker for hepatocellular carcinoma," Clin Chem Lab Med, Sep. 11, 2017, 6 pp.
Xu et al., "Serum exosomal long noncoding RNAs ENSG00000258332.1 and LINC00635 for the diagnosis and prognosis of hepatocellular carcinoma," Apr. 12, 2018, 23 pp.
Xu et al., "Lung adenocarcinoma cell-derived exosomal miR-21 facilitates osteoclastogenesis," Gene, Elsevier, May 2, 2018, 7 pp.

(56) References Cited

OTHER PUBLICATIONS

Yang et al., "Role of Exosomal miRNA in Multiple Myeloma Progress and Its Possible Mechanism," Translation of the Abstract Only, J. Exp. Hematol, Feb. 2017, 6 pp.

Zhang et al., "Exosomes in cancer: small particle, big player," Journal of Hematology & Oncology, Jul. 10, 2015, 13 pp.

Zhang et al., "The Ferromagnetic Resonance Measurements of Magnetic Nanowire Biolabels," University of Minnesota Institute for Engineering (EIM) Annual Conference and Retreat, Sep. 2018, 1 pp.

Zhang et al., "Transfer of microRNAs by extracellular membrane microvesicles: a nascent crosstalk model in tumor pathogenesis, especially tumor cell-microenvironment interactions," Journal of Hematology & Oncology, Feb. 22, 2015, 8 pp.

Zhou et al., "Reprogramming Malignant Cancer Cells toward a Benign Phenotype following Exposure to Human Embryonic Stem Cell Microenvironment," PLOS One, Jan. 9, 2017, 14 pp.

Zhou et al., "Robustly detecting differential expression in RNA sequencing data using observation weights," Nucleic Acids Research, vol. 42, Issue 11, Mar. 31, 2014, 10 pp.

Zhou et al., "Development of a Biolabeling System Using Ferromagnetic nanowires," IEEE Journal of Electromagnetics, RF and Microwaves in Medicine and Biology, vol. 3, No. 2, Dec. 2018, 10 pp.

Zhou et al., "Ferromagnetic Resonance Characterization of Magnetic Nanowires for Biolabel Applications," 2018 IEEE International Microwave Biomedical Conference (IMBioC), Jun. 2018, 3 pp.

Zimmerman et al., "Cellular uptake and dynamics of unlabeled freestanding silicon nanowires," Science Advances, vol. 2, No. 12, Dec. 2016, 12 pp.

Zoller, "Pancreatic cancer diagnosis by free and exosomal miRNA," World Journal of Gastrointestinal Pathophysiology, Nov. 15, 2013, 18 pp.

\* cited by examiner

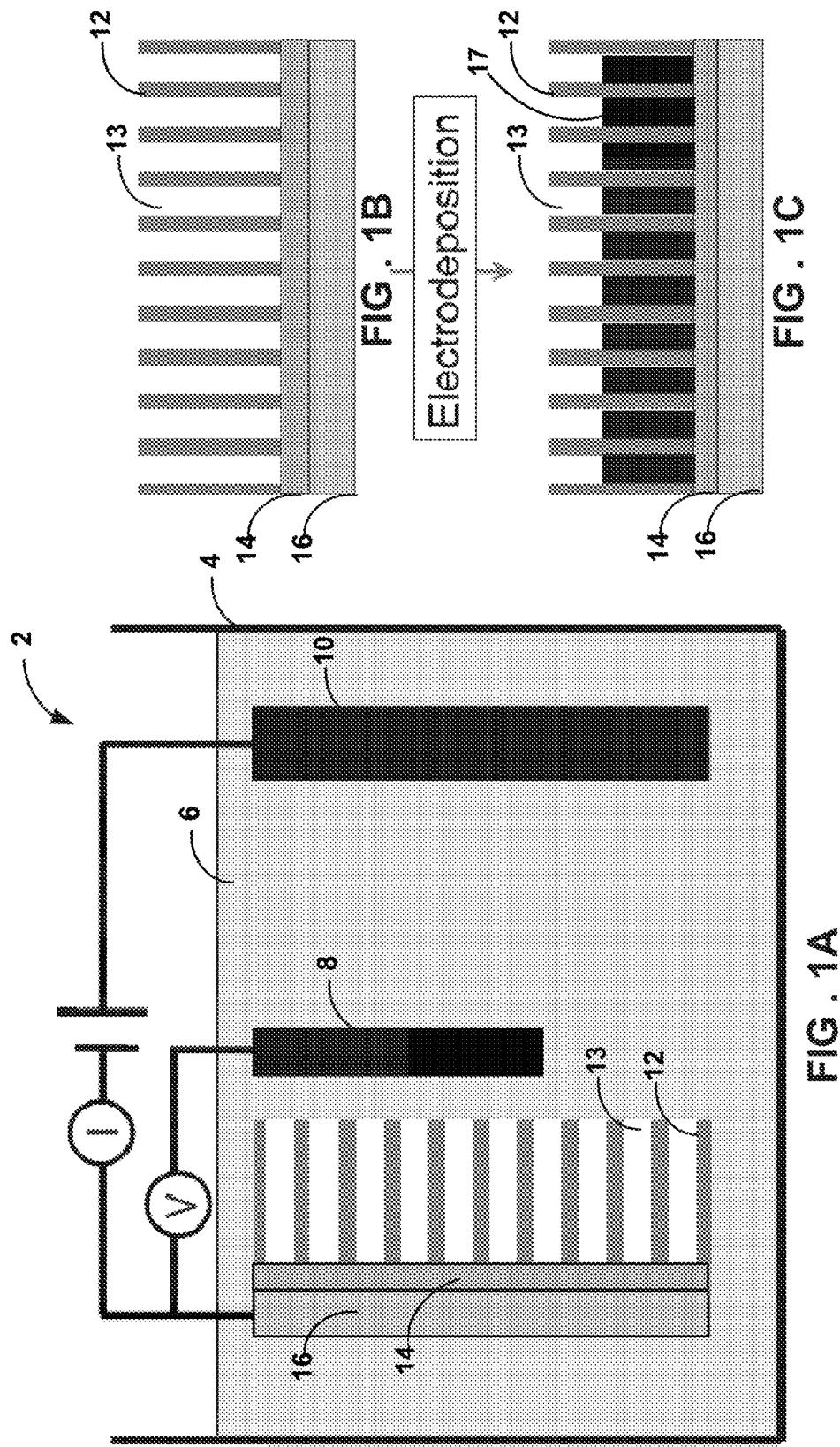

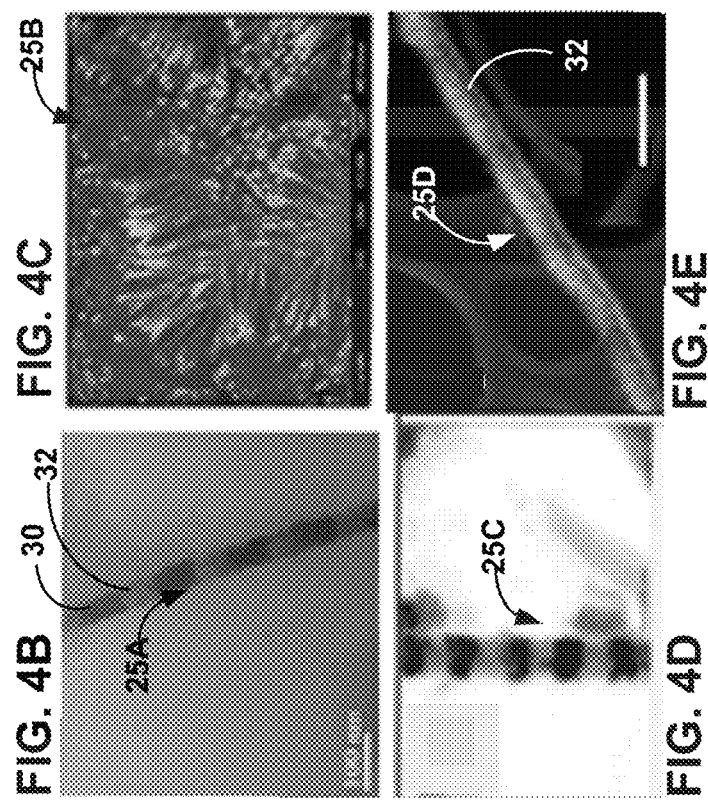
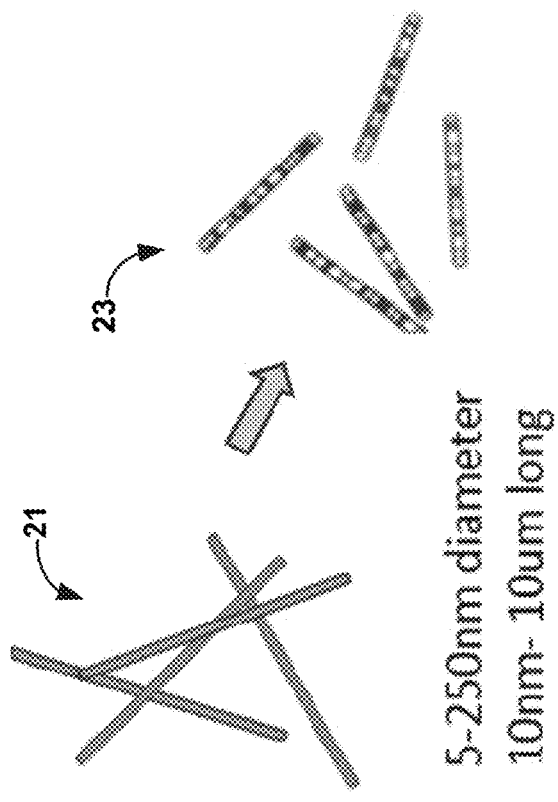

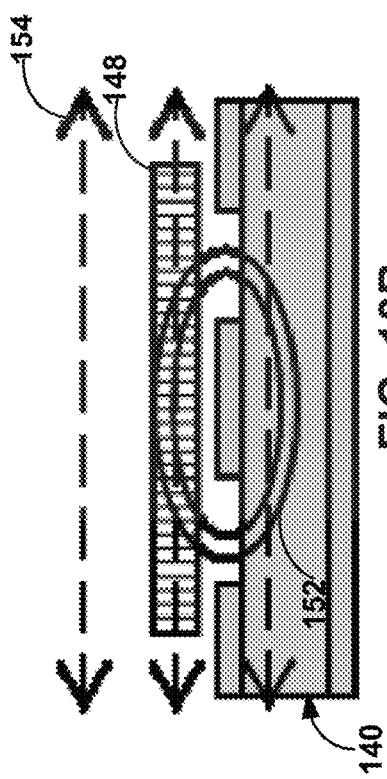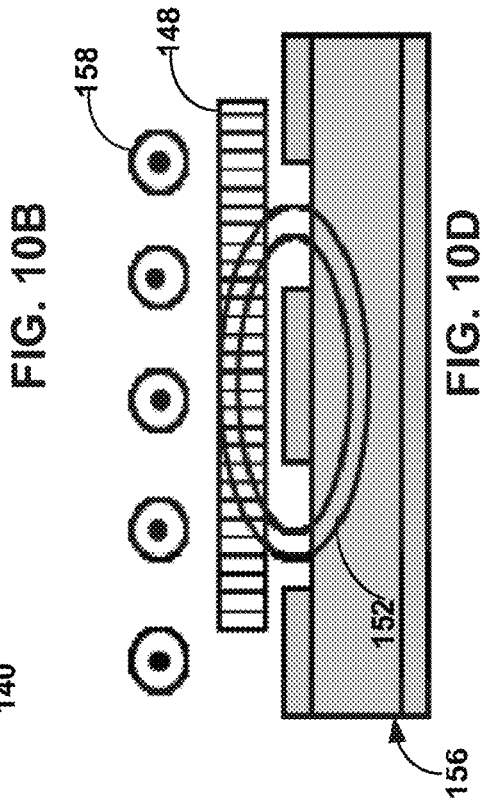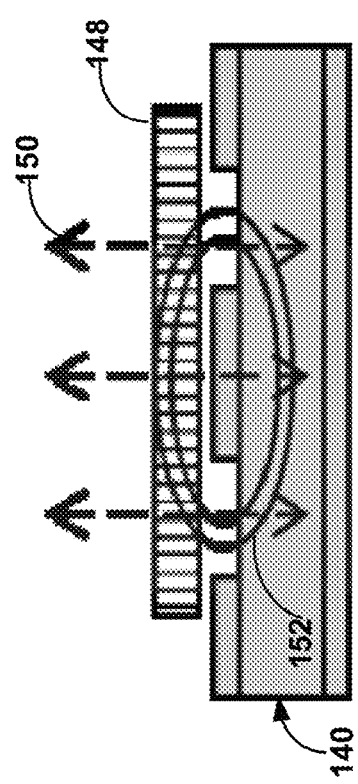

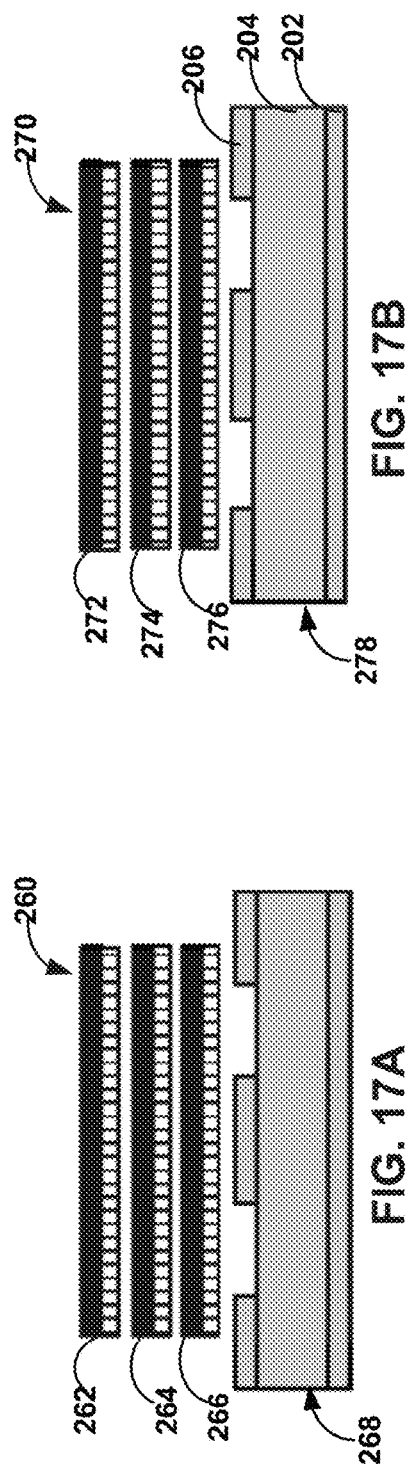
FIG. 17A
FIG. 17B
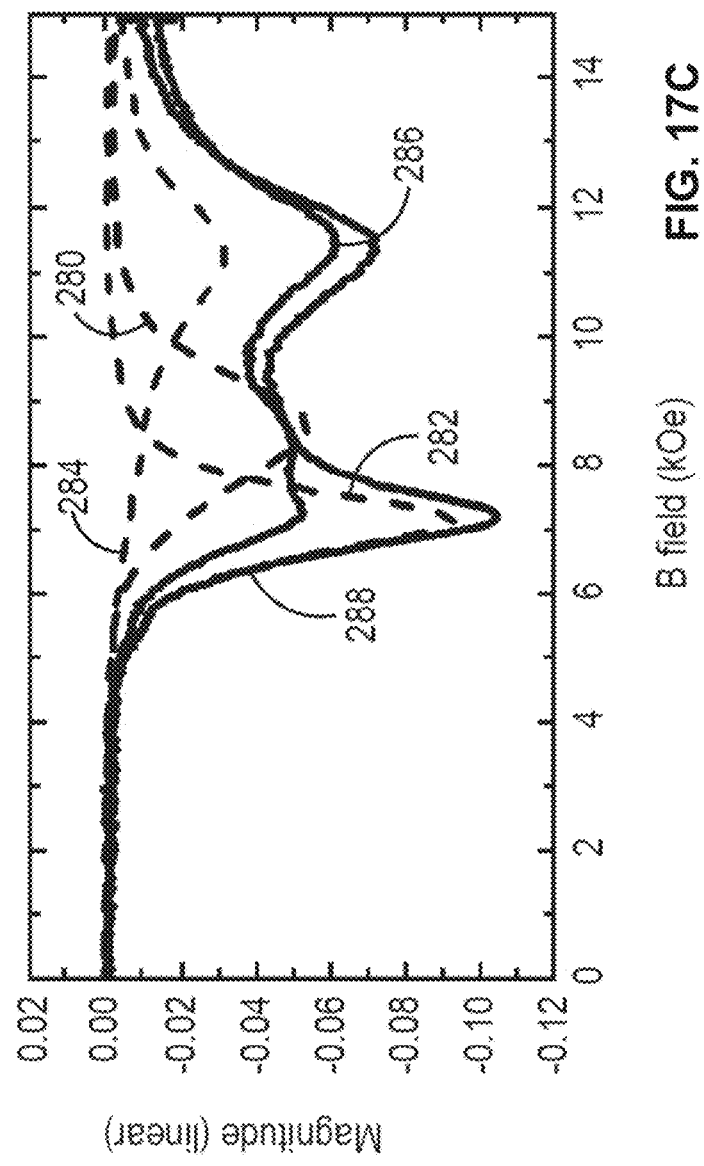
FIG. 17C

NANOWIRE CHARACTERIZATION AND IDENTIFICATION

This application is a continuation of U.S. patent application Ser. No. 16/151,206, filed Oct. 3, 2018, which claims the benefit of, and priority to, U.S. Provisional Patent Application Ser. No. 62/567,606, entitled "EXOSOME ENRICHMENT" and filed on Oct. 3, 2017, the entire content of these applications being incorporated by reference herein.

TECHNICAL FIELD

This disclosure relates generally to nanowires, and, more specifically, methods, devices, and systems for detecting, identifying, and/or characterizing magnetic nanowires.

BACKGROUND

Methods and systems for the labeling and identification of objects have widespread use in modern society. Labeling systems can include visual barcodes or a microchip identification tag containing identifying information. These systems typically utilize a scanning device configured to obtain information from the barcode or tag. For example, a radio-frequency identification (RFID) system may include a scanning device that interrogates RFID tags by emitting a radio-frequency (RF) signal toward the tag and receiving the identifying information from the tag in response to the RF signal.

SUMMARY

Devices, systems, and methods are described for detecting, identifying, and characterizing magnetic nanowires (MNWs) and uses thereof. Despite improvements in the miniaturization of conventional microchip-based identification tags (e.g., radio frequency identification or "RFID" tags), their macroscopic size limits the applications in which they can be used. Labeling methods and systems utilizing nanoscale magnetic wires as identifying labels have broad applicability to labeling applications on both macroscopic and microscopic scales. Such approaches enable the labeling of objects too small to be labeled with conventional identification tags, for example, and enable the incorporation of MNW tags into the material of the object to be labeled. The MNWs and labeling systems described herein may have applications associated with inanimate objects or even biological materials and systems.

MNWs can be manufactured to have distinguishing magnetic characteristics that enable each type of MNW to be individually identified and distinguished from other types of MNWs. The distinguishing magnetic characteristics of the types of MNWs are tunable and can be varied based on one or more design factors such as composition, dimension, and/or segmented MNW configuration. Once manufactured, the distinguishing magnetic characteristics of different types of MNWs can be determined to characterize the MNW for later identification of the MNW and an associated object, such as by ferromagnetic resonance (FMR) analysis of the MNW and/or an object associated with the MNW. Techniques and systems described herein can identify multiple types of MNWs present in a sample or object via modeling based on known characteristics of each MNW type. Therefore, MNWs can be used as part of a barcode-like system of MNWs for labeling and identification of objects that may range in size from microscopic to macroscopic sizes.

In one example, a method comprises: determining a magnetic field transmission characteristic corresponding to each type of magnetic nanowire (MNW) of a plurality of types of MNWs; determining a ferromagnetic resonance (FMR) characteristic of each type of MNW of the plurality of types of MNWs, wherein each type of MNW has an FMR characteristic that differs from an FMR characteristic of each other type of MNW of the plurality of types of MNWs; identifying each type of MNW of the plurality of types of MNWs based on the corresponding magnetic field transmission characteristic and the corresponding FMR characteristic; and associating each type of MNW of the plurality of MNWs with a corresponding object of a plurality of objects, wherein each object differs from at least one other object of the plurality of objects.

In another example, a system comprises: a memory; and processing circuitry configured to: receive, from a remote computer, data representative of a magnetic field transmission characteristic corresponding to each type of magnetic nanowire (MNW) of a plurality of types of MNWs; receive, from the remote computer, data representative of a ferromagnetic resonance (FMR) characteristic of each type of MNW of the plurality of types of MNWs, wherein each type of MNW has an FMR characteristic that differs from an FMR characteristic of each other type of MNW of the plurality of types of MNWs; identify each type of MNW of the plurality of types of MNWs based on the corresponding magnetic field transmission characteristic and the corresponding FMR characteristic; and associate, in the memory, each type of MNW of the plurality of MNWs with a corresponding object of a plurality of objects, wherein each object differs from at least one other object of the plurality of objects.

In another example, a non-transitory computer-readable storage medium comprising instructions that, when executed by processing circuitry, cause the processing circuitry to: receive, from a remote computer, data representative of a magnetic field transmission characteristic corresponding to each type of magnetic nanowire (MNW) of a plurality of types of MNWs; receive, from the remote computer, data representative of a ferromagnetic resonance (FMR) characteristic of each type of MNW of the plurality of types of MNWs, wherein each type of MNW has an FMR characteristic that differs from an FMR characteristic of each other type of MNW of the plurality of types of MNWs; identify each type of MNW of the plurality of types of MNWs based on the corresponding magnetic field transmission characteristic and the corresponding FMR characteristic; and associate, in a memory, each type of MNW of the plurality of MNWs with a corresponding object of a plurality of objects, wherein each object differs from at least one other object of the plurality of objects.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIGS. 1A-1C are graphical representations of an example technique for manufacturing MNWs in accordance with the examples of this disclosure.

FIG. 4A is a graphical representation of MNWs having unique FMR signatures that may be produced, such as single-component MNWs and multi-segmented MNWs, in accordance with the examples of this disclosure.

FIGS. 4B-4E are electron micrographs of multi-segmented MNWs produced in accordance with the examples of this disclosure.

FIG. 10A is a graphical representations of example magnetic field distributions at an A-B cross-section on a through-line co-planar waveguide (CPW) board with $B_{DC}$ in the easy axis.

FIG. 10B is a graphical representations of example magnetic field distributions at an A-B cross-section on a through-line CPW board with $B_{DC}$ in the hard axis.

FIG. 10C is a graphical representations of example magnetic field distributions at an A-B cross-section on a Z-shape CPW board with $B_{DC}$ in the easy axis.

FIG. 10D is a graphical representations of example magnetic field distributions at an A-B cross-section on a Z-shape CPW board with $B_{DC}$ in the hard axis.

FIGS. 17A and 17B are graphical representations of multiple example types of MNW samples arranged on a CPW board in accordance with this disclosure.

FIG. 17C is a graphical representation of a comparison of data obtained via an application of an example MNW identification technique to the multiple types of MNW samples FIGS. 17A and 17B with known data pertaining to individual MNW types.

DETAILED DESCRIPTION

Figure 2B:
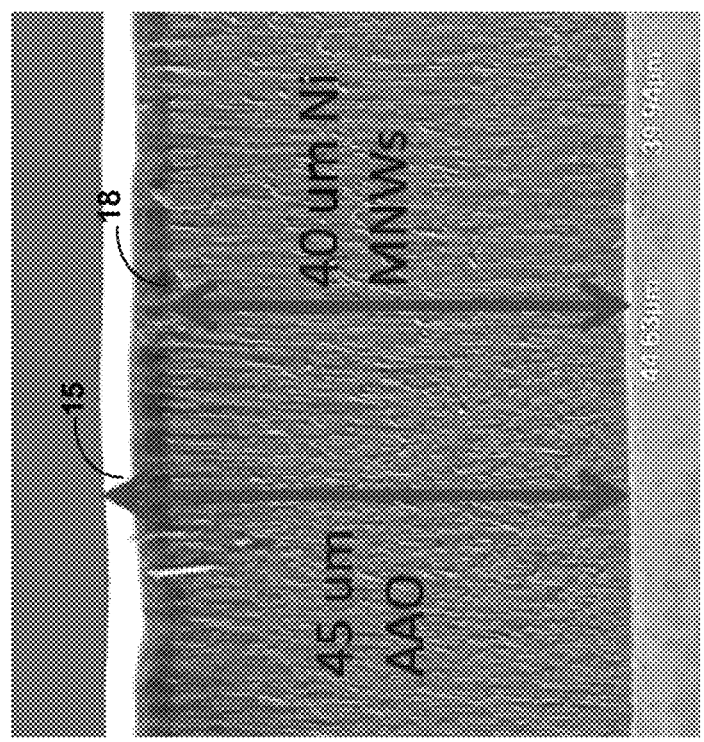
FIGS. 2A and 2B are scanning electron microscope (SEM) images of example MNWs manufactured in accordance with the examples of this disclosure.

In general, this disclosure describes example systems, devices, and techniques related to the manufacturing, characterization, detection, and identification of one or more types of magnetic nanowires (MNWs). For example, based on a magnetic field transmission characteristic (e.g., using an FMR technique) of each type of MNW, a system may be configured to detect and/or identify the one or more types of MNWs present in a sample. In this manner, a system may leverage MNWs for labeling objects with one or more types of MNWs and then identifying objects based on the identification of the one or more types of MNWs associated with each object.

Several different labeling mechanisms can be used to identify various objects. For example, one dimensional or two dimensional visual bar codes are commonly used to identify goods in the marketplace. As another example, RFID tags can be attached to objects and interrogated without the need for line of sight to the tag. A scanner can transmit an RF signal to the RFID tag that energizes the RFID tag circuit, and the energized circuit broadcasts a unique signal detectable by the scanner. However, both visual bar codes and RFID tags have limitations on the types of objects to which they can be attached and the mechanism for interrogation. For example, visual bar codes and RFID tags are not suitable for labeling very small objects (e.g., microscopic scales) or some biological systems or biological components. As described herein, MNWs may be associated with (e.g., attached to, formed in, or otherwise contained by) very small and/or biological objects and detected by an interrogation system to detect and/or identify objects associated with respective types of MNWs.

A magnetic field transmission characteristic of a type of MNW may be determined, such as by subjecting the type of MNW to a magnetic field from a magnetic field source (e.g., a vibrating sample magnetometer (VSM) to determine a hysteresis curve for the type of MNW. An example FMR measurement system may be used to detect signals associated with an FMR characteristic of each type of MNW to enable the characterization and identification of individual types of MNWs. Such FMR measurement systems may include a microwave power source, a magnetic field source, and a microwave structure on which a sample may be placed. In some examples, the microwave power source of an FMR measurement system may be a vector network analyzer (VNA) that includes a microwave power source and transmission detector. In some examples, the microwave structure may be coplanar waveguide board (CPW board) to provide an AC magnetic field ($H_{AC}$), and the magnetic field source may be an electromagnet to provide a DC magnetic field ($B_{DC}$). A computing device that includes processing circuitry configured to analyze quantitative power measurements. For example, in examples in which an FMR measurement system includes a VNA, such quantitative measurements may include reflection data ($S_{11}$) and transmission data ($S_{21}$) of $H_{AC}$ corresponding to one or more types of MNWs contained in a sample positioned between poles of the electromagnet may be coupled to the FMR measurement system. The FMR measurement system may be used to characterize types of MNWs based on the principle that types of MNWs that differ in composition, dimension, and/or segmented or non-segmented configuration each will have an FMR characteristic specific to that type of MNW. As discussed further below, a segmented configuration of the MNW may be constructed of different types of materials along the axial length of the MNW.

To determine an FMR characteristic specific to a type of MNW, a processing unit of the computing device may cause one or more electromagnets to apply $B_{DC}$ to the type of MNW and control the microwave power source of the VNA to direct a first RF signal or microwave signal to the type of the MNW while the type of MNW is positioned on the CPW and subjected to the magnetic field. Although first signals having frequencies in the RF or in the microwave ranges may be used, such signals may be referred to herein as being RF signals for the sake of clarity, though such descriptions are not intended to be limiting. In some examples, the processing unit of the computing device may include software and/or hardware (e.g., processing circuitry) configured to carry out one or more of the functions described herein with respect to the comping device. Although such functions may be described herein as being carried out by processing circuitry, any suitable software may be used to carry out such functions in other examples. For example, the processing circuitry may control the one or more electromagnets to apply $B_{DC}$ to the type of MNW at varying field strength while the frequency of the first RF signal is held constant. The processing circuitry of the computing device may detect a second RF signal resulting from the first RF signal passing by and/or through the type of MNW, where the difference between the first RF signal and the second RF signal corresponds to a RF absorption of the type of MNW. It should be noted that although such second signals may be referred to herein as being transmitted RF signals, such signals also may be referred to as being AC transmission ($S_{21}$) signals due to the nature of the microwave power source and the CPW board.

The processing circuitry then may determine a $B_{DC}$ strength at which FMR is induced in the type of MNW when the MNW is subjected to the $B_{DC}$ and the first RF signal, such as by determining a $B_{DC}$ at which nulls, or reductions, in $S_{21}$ occur for a particular frequency of the first RF signal. In some examples, such as in example techniques for the characterization and identification of the example MNW types described herein, the frequency of the first RF signal or microwave signal respectively may be from about 1-3 GHz to about sub-millimeter wave≥about 110 GHz and about 3-30 GHz to about millimeter-wave 30-110 GHz. Such nulls in $S_{21}$ correspond to an increase in RF absorption by the type of MNW, which may be indicative of induced FMR at a particular magnetic field strength and RF signal frequency. In some examples, the processing circuitry may determine that FMR has been induced in the type of MNW by determining whether an $S_{21}$ value resulting from the application of the $B_{DC}$ and the first RF signal satisfies a threshold $S_{21}$ associated with FMR.

The processing circuitry then may determine the FMR characteristic of the MNW to be a $B_{DC}$ strength at which FMR is induced in the type of MNW. This technique may be carried out for each type of MNW of a plurality of MNWs to determine an FMR characteristic of each type. Based on the FMR characteristic and the magnetic field transmission characteristic of each type of MNW, the processing circuitry may identify each type of MNW of the plurality of types of MNWs (e.g., by storing one or more of the magnetic field transmission characteristic and the $B_{DC}$ at which FMR occurs in a memory of the computing device or other device. The processing circuitry then may associate each type of MNW of the plurality of types of MNWs with a corresponding object of a plurality of objects, each of which may differ from at least one other object of the plurality of objects. In some examples, the magnetic field transmission characteristic may refer to the magnetic field strength at a particular frequency of RF signal, one or more coefficients of a formula characterizing the AC transmission, or any other such parameters indicative of the particular FMR response for each type of MNW.

In some examples, the $B_{DC}$ strength at which FMR is induced in a type of MNW may be a first $B_{DC}$ at which FMR occurs in the type of MNW. In some such examples, the processing circuitry may determine one or more additional $B_{DC}$ strengths at which FMR occurs in the type of MNW by varying a frequency of the first RF signal directed toward the type of MNW, and may determine the FMR characteristic of the type of MNW as further being at least one of a second $B_{DC}$ or a second RF frequency at which FMR is induced in the type of MNW.

Once the processing circuitry identifies a type of MNW, the processor may associate, or enable a user to associate (e.g., via a user interface) a type of MNW to an object. In some such examples, the object may be a chemical composition (e.g., a material), an article of manufacture (e.g., a circuit board, microchip, polymer, etc.), or an organism (e.g., a biological object or system), and associating the type of MNW with the object may include storing the FMR characteristic of the MNW in a memory of the computing device in association with the chemical composition, article of manufacture, or organism. The processing circuitry may so associate a plurality of types of MNWs with a plurality of different objects in the memory of the computing device.

Associating the type of MNW with a chemical composition or article of manufacture may further include incorporating the type of MNW into the material of the chemical composition or the article of manufacture or attaching the type of MNW to the chemical composition or the article of manufacture, such as during the manufacture thereof. Such chemical compositions or articles of manufacture may be ones of many types of objects that it may be desirable to label at the nanoscale level. Examples of such types of objects may include, but are not limited to, microchip circuitry, textiles, personal identification devices, packaging, parts of a larger article of manufacture, raw materials, or others. In some such examples, the MNW label may help enable identification (e.g., via a detector or interrogation device) of an origin of the chemical composition or article of manufacture, track its movement (e.g., through a supply chain), indicate where or how an article of manufacture is configured to be incorporated into a larger article of manufacture, regulate access to secured areas, or other such results.

In other examples, associating a type of MNW with an object may include introducing the type of MNW into an organism or attaching the type of MNW to the organism. For example, the type of MNW may be introduced into a bloodstream or tissue of choice of an organism, where the type of MNW may be taken up by cells circulating in the bloodstream or within the tissue. In some such examples, the type of MNW may include a biocompatible coating disposed at least partially external from a core of ferromagnetic material. A biocompatible coating may help reduce surface oxidation of the MNWs, reduce metal toxicity, and/or reduce MNW agglomeration. Polyethylene glycol (PEG) is an example of one such coating, although others may be used. A biologically-active compound, which may help functionalize the type of MNW for interaction with a cell type or tissue of interest within the organism, may be linked to the coating. For example, arginylglycylaspartic Acid (RGD) linked to PEG adheres to integrins in U87MG tumors and folate linked to PEG adheres to folate receptor inside KB3-1 cells and M109 cells. Thus, MNWs may be targeted to cells of interest. In some examples, the biologically active compound linked to the coating may be a signaling molecule configured to regulate the activity of one or more biochemical pathways, such as pathways that regulate gene expression.

Types of MNWs may be manufactured such that at least one of a composition or dimension of each type of MNW of the plurality of types of MNWs differs from at least one of a composition or dimension of at least one of a composition or dimension of each other type of MNW of the plurality of types of MNWs, which contribute to the different FMR characteristics of the types of MNWs. In some examples, the composition of each type of MNW of the plurality of MNWs may comprise at least one of cobalt (Co), iron (Fe), nickel (Ni), copper (Cu), or gold (Au). The types of MNWs may include a single ferromagnetic material or may include a plurality of segments. In examples in which a type of MNW includes a plurality of segments, a first segment of the plurality of segments may be a ferromagnetic material (e.g., Co, Fe, or Ni) and a second segment may be a second material different from the ferromagnetic material (e.g., Cu or Au). The first and second segments may be adjacent (e.g., next to or serially connected) to each other in some examples, and may have different dimensions. In some examples, segments of an insulating material, which may be any suitable electrically insulating material, may be positioned between one or more of the first segments and/or between one or more of the second segments, such that one or more insulating segments may be interspersed among the first segments and/or the second segments within a MNW, in any suitable configuration.

Using the characterization of the types of MNWs (e.g., determination of the magnetic field transmission characteristic and FMR characteristic of each type of MNW), processing circuitry of a computing device configured to interrogate the object, which may be the same computing device used in the characterization of the types of MNWs or a different computing device, may be configured to identify an object associated with one or more MNWs based on received data. For example, the processing circuitry may receive data representative of a FMR characteristic of each type of MNW of a plurality of types of MNWs that each have an FMR characteristic that differs from an FMR characteristic of each other type of MNW of the plurality of types of MNWs, such as from another computing device that stores the FMR characteristics of the types of MNWs in a memory thereof. The processing circuitry also may receive data representative of an FMR scan comprising an application of a magnetic field to the object, determine a magnetic field transmission characteristic of the object based on the data, identify one or more types of MNWs of the plurality of types of MNWs associated with the object based on the magnetic field transmission characteristic of the object, and identify the object based on the one or more types of MNWs identified based on the magnetic field transmission characteristic of the object.

In some such examples, the FMR scan of the object may be conducted, such as by a scanning device including electromagnets and a FMR measurement system that includes a microwave power source, a magnetic field source (e.g., a VNA) as described herein. For example, such a device may conduct the FMR scan by at least applying a magnetic field to the object, directing a first radio frequency signal toward the object while the object is subject to the magnetic field, detecting a second radio frequency signal resulting from the first radio frequency signal passing by the object, generating data representative of the second radio frequency signal, and transmitting the data representative of the second radio frequency signal to the processing circuitry of the computing device. The processing circuitry thus may identify the object based on the one or more types of MNWs identified by the magnetic field transmission characteristic of the object by comparing the magnetic field transmission characteristic of the object to the respective FMR characteristics of the at least one type of MNW of the plurality of MNWs, and identify the object based on the comparison.

In some examples, processing circuitry of a computing device may be configured to interrogate a sample containing at least two types of MNWs of a plurality of MNWs. The computing device used to interrogate the sample may be the same computing device used in the characterization of the types of MNWs or may a different computing device. The processing circuitry of the computing device may identify the at least two types of MNWs of a plurality of types of MNWs contained within the object or sample. For example, the processing circuitry may receive data representative of a FMR characteristic of each type of MNW of a plurality of types of MNWs that each have an FMR characteristic that differs from an FMR characteristic of each other type of MNW of the plurality of types of MNWs, such as from another computing device that stores the FMR characteristics of the types of MNWs in a memory thereof. The processing circuitry also may receive data representative of an FMR scan comprising an application of a magnetic field to the sample.

In some such examples, the processing circuitry may determine a magnetic field transmission characteristic of the sample based on the data, where the magnetic field transmission characteristic of the sample corresponds to a combination of the respective FMR characteristics of the at least two types of MNWs contained in the sample, and identify each of the at least two types of MNW of the plurality of types of MNWs contained in the sample based on the magnetic field transmission characteristic of the sample and the FMR characteristics corresponding to the plurality of types of MNWs. For example, the processing circuitry may identify sample based on the magnetic field transmission characteristic of the sample and the FMR characteristics corresponding to the plurality of types of MNWs by comparing the magnetic field transmission characteristic of the sample to respective FMR characteristics of at least two types of MNWs of the plurality of MNWs and identifying each of the at least two types of MNWs based on the comparison.

In some such examples, the FMR scan of the object may be conducted, such as by a scanning device including electromagnets and a VNA as described herein. For example, such a device may conduct the FMR scan by at least applying the magnetic field to the sample, directing a first radio frequency signal toward the sample while the sample is subject to the magnetic field, detecting a second radio frequency signal resulting from the first radio frequency signal passing by the object, generating data representative of the second radio frequency signal, and transmitting, to the processing circuitry, the data representative of the second radio frequency signal.

The techniques and systems described herein may have broad applicability. For example, miniaturization and personalization of goods, services, and healthcare can benefit from the ability to label objects with labels of decreasing size. In some such applications, the MNWs may function as biolabels that may help identify a presence of a biomarker of interest within a biological sample derived from an organism. For example, a plurality of MNWs may be introduced into one or more cells, such as tumor cells from a donor organism or other cells of interest, which then may be introduced into a body of a host organism. The cells and/or their progeny may release exosomes containing the MNWs into the bloodstream of the host organism. A plurality of such exosomes then may be obtained from a sample of bodily fluid from the host organism and one or more exosomes that each contain one or more MNWs of the plurality of MNWs may be isolated from the plurality of exosomes. The exosomes containing the one or more MNWs may be analyzed to determine whether the sample contains a biomarker indicative of a biological status based on the presence of the one or more MNWs of the plurality of MNWs. The biological status may be associated with one of a presence, an absence, or a stage of a health condition or any other biological status of interest.

In some examples, the plurality of MNWs comprises a plurality of types of MNWs, wherein each type of MNW of the plurality of types of MNW comprises a respective composition different from compositions of other types of MNWs of the plurality of types of MNWs, and wherein the respective FMR characteristic of each type of MNW of the plurality of types of MNWs differs from FMR characteristics of other types of MNWs of the plurality of types of MNWs, the method further comprising identifying each of the one or more types of MNWs of the plurality of MNWs contained within the one or more exosomes.

In some such examples, an FMR scan of the one or more exosomes may be conducted, such as by applying a magnetic field to the one or more exosomes, directing a first radio frequency signal toward the one or more exosomes while the one or more exosomes are subject to the magnetic field, and detecting a second radio frequency signal resulting from the first radio frequency signal passing by the object. A magnetic field transmission characteristic of the one or more exosomes then may be determined based on the FMR scan. In such examples, identifying each of the one or more types of MNWs contained within the one or more exosomes may include comparing the magnetic field transmission characteristic of the one or more exosomes to respective FMR characteristics of one or more types of MNWs of the plurality of MNWs and identifying each of the one or more types of MNWs based on the comparison.

In some examples in which the plurality of MNWs comprises a plurality of types of MNWs, the one or more cells comprise a plurality of cell types. In some such examples, each of the types of MNWs of the plurality of types of MNWs may correspond to a cell type of the host organism, and at least one cell type contained within in the sample of bodily fluid may be identified based on the identity of each of the one or more types of MNWs contained within the one or more exosomes.

In any of the examples described above, techniques and systems for labeling objects with MNWs may enable the labeling of objects at the nanoscale level. Labeling objects at the nanoscale level may provide one or more benefits. For example, the nanoscale proportions of MNWs may enable incorporation of the MNWs into the very material of an object during manufacturing of the object. The incorporation of MNWs into the material of an object may help prevent the label from becoming detached from the object. In some applications in which visual or tactile detectability of the label may be a consideration, such as in loss-prevention applications, the incorporation of MNWs into the object may help such labels escape detection. In some applications in which damage to larger-scale or more complex labels may be a consideration, the simplicity of MNW design and the ability to incorporate MNWs into the material of an object may enable labeling of objects that may be subjected to conditions that may degrade other types of labels. Labeling of objects with MNWs at the nanoscale level also enables labeling of objects that are too small to be labeled with other types of labels such as conventional chip-based RFID tags. For example, as described herein, MNWs may be used in biolabeling applications, where their small size enables the MNWs to be incorporated into microscopic biological structures such as cells and exosomes released from cells. In some examples, the use of MNWs as biolabels may help facilitate prompt diagnosis of disease, accurate determination of prognosis, and/or help predict response to drug therapy, as described in further detail below.

The MNW labeling systems described herein may provide various advantages over other systems, such as the conventional RFID tags described above, which utilize tags that are much larger in size. In addition, the use of MNWs in nanoscale labeling systems may be advantageous over the use of other nanoscale materials, such as magnetic nanoparticles (MNPs). For example, MNPs are typically fabricated by co-precipitation from metallic salt solutions, which often leads to broad size distribution. MNWs, however, are electrodeposited inside anodic aluminum oxide (AAO) templates, which enable better control of shapes and sizes and, if desired, segmented construction of the MNWs. The large surface area of MNWs relative to MNPs also better enables bio-functionalization of MNWs with coatings and other molecules relative to MNPs. In addition, MNWs have large shape anisotropy for a wider range of engineered magnetic properties compared to MNPs, which facilitates the production of "barcode"-like systems of MNWs that each have different magnetic characteristics. The example systems and techniques for MNW manufacture, characterization, and identification thus provide a tunable nanoscale labeling system with broad applicability.

FIGS. 1A-22 illustrate example systems and techniques for the manufacture, characterization, and identification of MNWs. FIGS. 23-30 illustrate an example application of MNWs as biolabels for the determination of a biological state of an organism. Although some of the illustrated examples described below are described with respect to a particular material, measured value, or application, the concepts pertaining to such examples may be applicable to other materials, values, or applications and are not intended to be limiting.

FIGS. 1A-1C are graphical representations of technique for manufacturing MNWs by electrodeposition in accordance with the examples of this disclosure. FIG. 1A illustrates an example MNW electrodeposition system 2, which includes a vessel 4 that contains electrolyte solution 6, reference electrode 8, and counter electrode 10. Vessel 2 further contains porous AAO template 12, which defines pores 13 in which MNWs will be formed during electrodeposition. A titanium (Ti) adhesion layer 14 having a thickness of about 7 nanometers (nm) and a Cu working electrode 16 having a thickness of about 300 nm (thicknesses not shown to scale) may be fabricated onto AAO template 12. By monitoring the amount of charge deposited to the system, the amount of material deposited may be controlled, thereby controlling the MNW length.

FIG. 1B illustrates AAO template 12, pores 13, Ti adhesion layer 14, Cu working electrode 16 prior to electrodeposition of MNWs. FIG. 1C illustrates MNWs 17 formed within pores 13 prior to electrodeposition. Example electrodeposition parameters for the electrodeposition of Co, Fe, and Ni may be as follows. For Co MNWs, a solution of $CoSO_4$ and $H_3BO_3$ at a pH of 2 and V=−0.95 versus Ag/AgCl at room temperature (approx. 20 C) may be used. For Fe MNWs, a solution of $FeSO_4$, $H_3BO_3$, and $C_6H_6O_6$ at a pH of 3 and V=−1.1 versus Ag/AgCl at room temperature may be used. For Ni MNWs, a solution of $NiSO_4$, $H_3BO_3$ at a pH of 3 and V=−0.9 versus Ag/AgCl at room temperature may be used. After electrodeposition of MNWs 17, coatings and/or functionalizing ligands may be applied to an exterior of MNWs 17 as may be suitable for a desired application of MNWs 18, such as the PEG coatings and biofunctionalizing ligands described above.

Figure 2A:
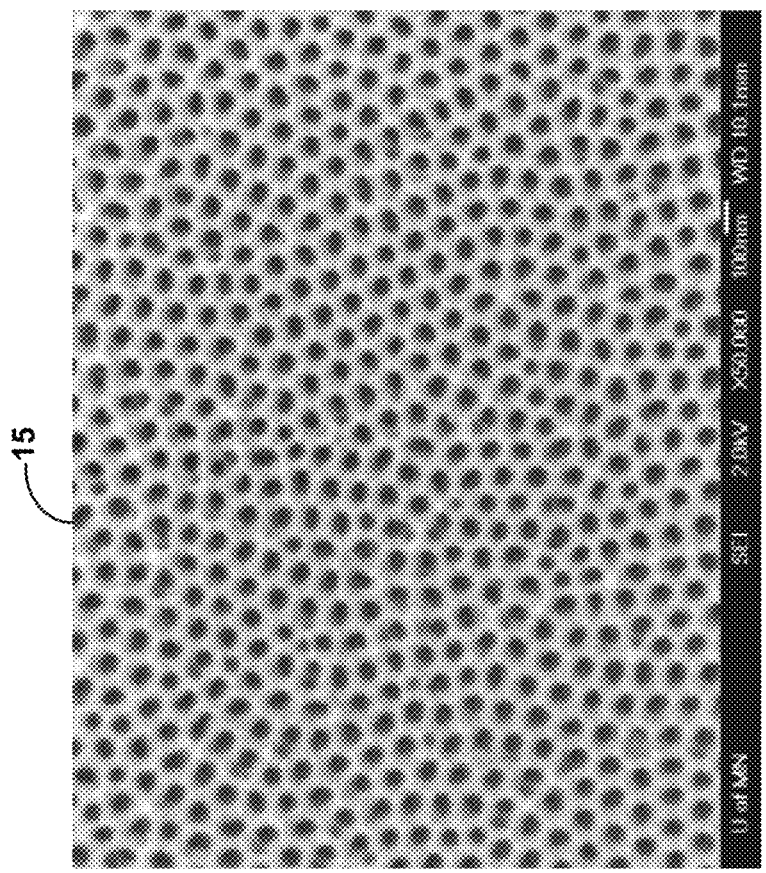

FIGS. 2A and 2B are scanning electron microscope (SEM) images of an AAO template and MNWs manufactured in accordance with the examples of this disclosure, such as according to the example described with respect to FIGS. 1A-1C. FIG. 2A is SEM image of an AAO template 15, which may be substantially similar to AAO template 12 illustrated in FIGS. 1A-1C, taken at a working depth (WD) of 10.1 millimeters (mm). A 100 nm scale is illustrated for reference at the bottom of the image. The image depicts a top view of an AAO template 15. The AAO template 15 shown in FIG. 2A has a pore diameter of about 40 nm and a porosity of about 12%. AAO template 15 may be used in the manufacture of Co or Fe MNWs. AAO templates having other pore diameters and/or other porosities may be desirable for use with other MNW materials. For example, an AAO template having a pore diameter of about 80 nm and a porosity of about 15% may be used in the manufacture of Ni MNWs, although AAO templates having any suitable pore diameter and porosity may be used in the manufacture of any of the MNWs described herein.

FIG. 2B is a SEM image of a cross-section of a Ni MNW array sample 18, the MNWs of which may be substantially similar to MNWs 17 of FIGS. 1A-1C. In the example of FIG. 2B, the Ni MNWs 18 having a length of about 40 μm and are pictured on an AAO template having a thickness of about 45 μm. MNWs 18 may be grown by pulsed electrodeposition in an array format inside AAO template 12. In this example, before the electrodeposition, a 100 nm thick titanium (Ti) followed by a 300 nm thick Cu film was sputtered on one side of AAO template 12 as an adhesion layer and an electric contact for the electrodeposition, respectively.

Figure 3A:
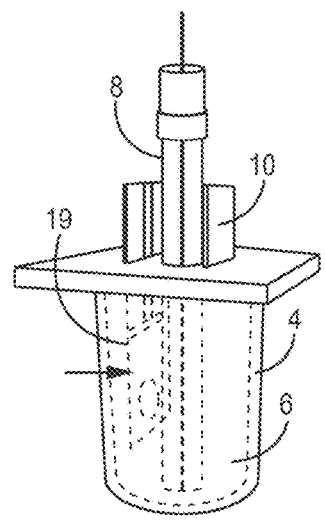
FIG. 3A is a graphical representation of an example apparatus for preparing multi-segmented MNWs by electro-chemical deposition in accordance with the examples of this disclosure.
Figure 3B:
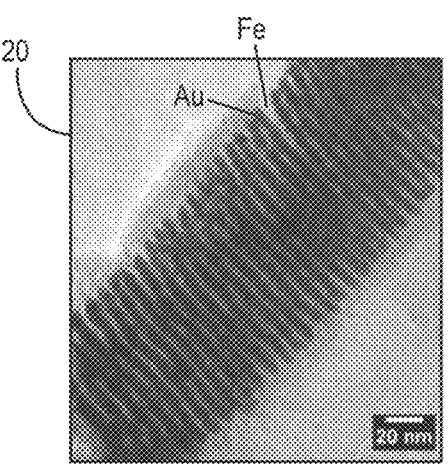
FIG. 3B is a digital image of an example multi-segmented MNW in accordance with the examples of this disclosure.
Figure 3C:
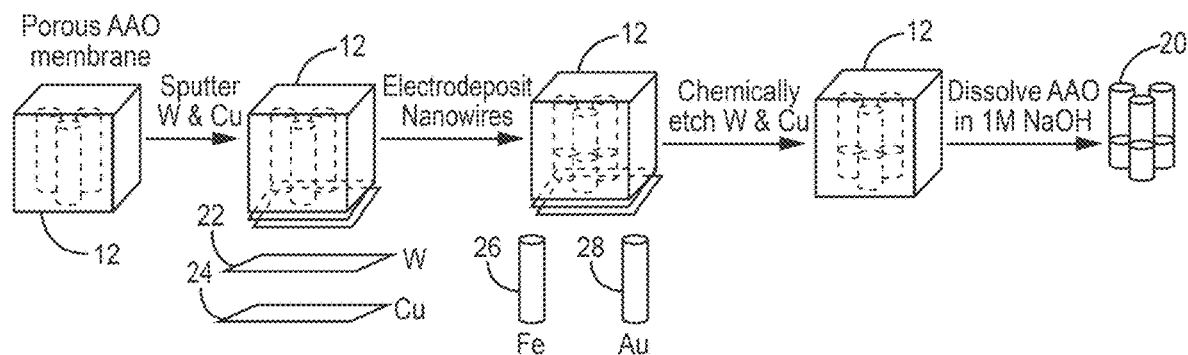
FIG. 3C is a graphical representation of an example method for producing multi-segmented MNWs in accordance with the examples of this disclosure.

FIGS. 3A-3C illustrate an application of electrodeposition system 2 of FIG. 1A to the manufacture of segmented MNWs. FIG. 3A is another side view of electrodeposition system 2, which in the example of FIGS. 3A-3C is used with AAO template 19, which may be substantially similar to AAO template 12 of FIGS. 1A-1C and/or AAO template 15 of FIGS. 2A and 2B.

FIG. 3B is a digital image of an example multi-segmented MNW 20 in accordance with the examples of this disclosure, which may be produced using electrodeposition system 2 of FIG. 1A. As described above, MNWs may include a plurality of segments. MNW 20 is an example of a Fe/Au MNW, with alternating Fe and Au segments, although in other examples segmented MNWs may have other configurations, as described below with respect to FIGS. 4A-4E.

FIG. 3C is a graphical representation of a method for producing multi-segmented MNWs, such as MNW 20 using electrodeposition system 2 or another suitable electrodeposition system. In the example of FIG. 3, a tungsten (W) adhesion layer 22 and a Cu working electrode 24 may be applied to AAO template 19. Next, MNWs 20 are electrodeposited into pores (not shown) of AAO template 19 using compounds containing Fe 26 and Au 28 in electrolyte solution 6. W adhesion layer 22 and Cu working electrode 24 then may be chemically etched away from AAO template 19, and AAO template 19 may be dissolved in 1M NaOH, leaving behind segmented Fe/Au MNWs 20. This technique for producing multi-segmented MNWs may be used in the production of other types of multi-segmented MNWs than Fe/Au MNW 20, such as Co/Cu MNWs or other suitable material combinations.

FIG. 4A is a graphical representation of MNWs having unique FMR signatures that may be produced, such as single-component MNWs 21 and multi-segmented MNWs 23, in accordance with the examples of this disclosure. The manufacture of MNWs having a segmented configuration like MNW 23 is tunable to enable the production of MNWs having different segmented configurations, which in turn may facilitate the production of "barcode"-like systems of MNWs that each have different magnetic characteristics.

FIGS. 4B-4E are electron micrographs of one or more of multi-segmented MNWs, which may be similar to multi-segmented MNWs 23 of FIG. 4A, and which may be produced in accordance with the examples of this disclosure. In the illustrated examples of FIGS. 4B-4E, respective multi-segmented MNWs 25A, 25B, 25C, and 25D may be Fe/Au MNWs having Fe segments 30 and Au segments 32, although multi-segmented MNWs 25A-25D may include other suitable material combinations, such as Co/Cu. The FMR characteristics of MNWs 25A-25D may be envisioned by picturing spinning "tops." The "tops" are the magnetic moments of each Fe segment 30. The moment can be made to spin by applying a customized radio frequency (cRF) signal in which the RF frequency matches the characteristic frequency of the "top." A short, flat "top" may spin at a different characteristic frequency than a tall, skinny "top," and the same is true of magnetic moments where the magnetic material has different aspect ratios (aspect ratio=length/diameter). In addition, the moments can be made to spin like a heavy "top" by applying a DC magnetic field together with the cRF input signal.

This DC magnetic field can be internal to each of multi-segmented MNWs 25A-25D. For example, segment geometries can be designed such that the segments impose an "effective field" on each other. A similar force can be felt when refrigerator magnets are stacked on top of each other or next to each other. In the first case, all of the segments want to align (north poles pointing "up" the MNW stack, not north-north or south-south) but in the second (next to each other) case, the segments have alternating orientations (north/south poles alternately pointing out of the side of the MNW). By spacing Fe segments 30 of multi-segmented MNWs 25A-25D closer to or further from each other using non-magnetic Au segments 32, the effective field the Fe segments impose on each other can be controlled. Multi-segmented MNWs 25A-25D may be synthesized as described above with respect to FIGS. 3A-3C. In this manner, MNWs with different FMR signatures can be engineered.

Figure 5C:
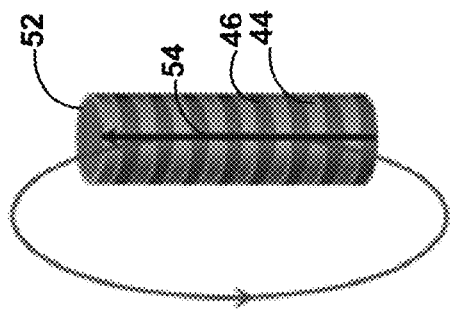
FIG. 5C is a graphical representation of an intra-MNW effective field that one MNW can exert on another.
Figures 5A, 5B:
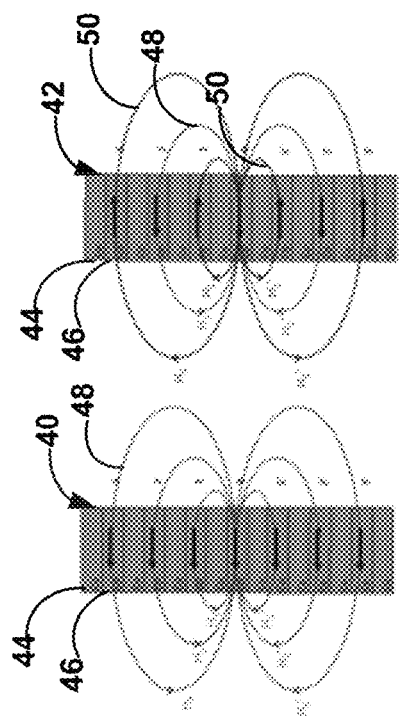
FIG. 5A is a graphical representation of example intra-MNW effective fields of ferromagnetic segments having parallel configurations.
FIG. 5B is a graphical representation of intra-MNW effective fields of ferromagnetic segments having antiparallel configurations.

FIG. 5A is a graphical representation of intra-MNW effective fields of a MNW 40 having Cu segments 44 and ferromagnetic Co segments 46, in which Co segments 46 have parallel configurations. FIG. 5B is a graphical representation of intra-MNW effective fields of a MNW 42 having Cu segments 44 and ferromagnetic Co segments 46, in which Co segments 46 have anti-parallel configurations. As shown in FIGS. 5A, magnetic fields 48 (i.e., $H_1$ $H_2$, and $H_3$) of Co segments 46 of MNW 40 are oriented in parallel. As shown in FIG. 5B, magnetic field 48 (i.e., $H_2$) of Co segments 46 of MNW 42 is oriented in anti-parallel to magnetic fields 50 (i.e., $H_1$ and $H_3$) of Co segments 46 of MNW 42. Thus, MNWs with different FMR signatures can be engineered by varying the direction of magnetic fields of multi-segmented MNWs in addition to, or instead of, varying the segment configurations.

The following Equation 1A may be used for calculating the effective fields of parallel MNW 40 of FIG. 5A and antiparallel MNW 42 of FIG. 5B, and Equation 1B may be used for calculating an intra-MNW effective field of the multi-segmented MNWs described below with respect to FIG. 5C:

$$\vec{H}_{dip} = \frac{1}{4\pi} \int \frac{d^2 r' \vec{M} . \hat{n}' (\vec{r} - \vec{r}')}{|\vec{r} - \vec{r}'|^3} \quad (1\ A)$$

$$H_{inter} = 6\pi M_s P \left(1 - 3 \sum_{i=0}^{N} (-1)^i N_i \right) \quad (1\ B)$$

When Co segments 46 are pancake-like in shape, they interact with each other as shown schematically in FIGS. 5A and 5B. The effective field that each Co segment 46 experiences can be calculated by the equation in FIG. 5C, where $6\pi M_s P$ is the interwire effective field, and the term in parentheses is a factor representing the effect of segmenting (i.e., adding nonmagnetic spacers between the magnetic segments). $M_S$ is the saturation magnetization, P is the density of the MNWs, N is the number of segments, and $N_i$ is the ith demagnetizing tensor that depends on the aspect ratios of the magnetic and nonmagnetic segments. In some examples, the MNWs may be too far apart to interact magnetically with each other, and segment-segment interactions may be engineered for appropriate cRFID signals.

FIG. 5C is a graphical representation of an intra-MNW effective field, which can be calculated according to Equation 2, that multi-segmented MNW 52, which includes Cu segments 44 and Co segments 46, can exert on another MNW. As shown in FIG. 5C, MNWs can also be designed to have anisotropies that are parallel to the MNW axis 54 of MNW 52. There are multiple approaches to engineer MNW with different FMR in the designated range. Large shifts in FMR frequency can be achieved by changing material composition (i.e. iron, nickel or cobalt) whereas small shifts of FMR can be achieved by adjusting MNW dimensions (e.g., length and/or diameter).

Table 1 summarizes the calculated demagnetizing factors with prolate ellipsoid model and the OOMMF simulated FMR and linewidth with respect to length. With same 40 nm diameter, when Co MNW length is under 1000 nm, there is a monotonic correlation between length and FMR frequency. However, when the length is over 1000 nm, the corresponding FMR change becomes insignificant.

TABLE I

SIMULATED SINGLE CO MNW FMR
WITH 1 KOE AXIAL BIAS FIELD

| Dimension | | Calculation | | Simulation | |
|---|---|---|---|---|---|
| Diameter (nm) | Length (nm) | Nz | Nx, Ny | FMR (GHz) | Linewidth (Oe) |
| 40 | 100 | 1.48 | 5.54 | 21.6 | 240 |
| 40 | 200 | 0.69 | 5.94 | 24.7 | 190 |
| 40 | 500 | 0.18 | 6.19 | 26.7 | 175 |
| 40 | >1000 | 0 | 6.28 | 27.1 | 175 |

Table 1 shows aspects of MNW tunability with MNW length. To have numerous FMR signatures to function as biolabels, and to maintain a constant FMR before and after incubation and separation, segmented MNWs are introduced. With segmented MNWs (e.g., MNWs 40, 42, 52), intra-MNW interaction provides additional tunability to FMR. By adjusting the spacing between each MNW segment, adding conductors like Au and Cu, or different magnetic materials, FMR shifts even with same overall diameter and length.

Figure 6:
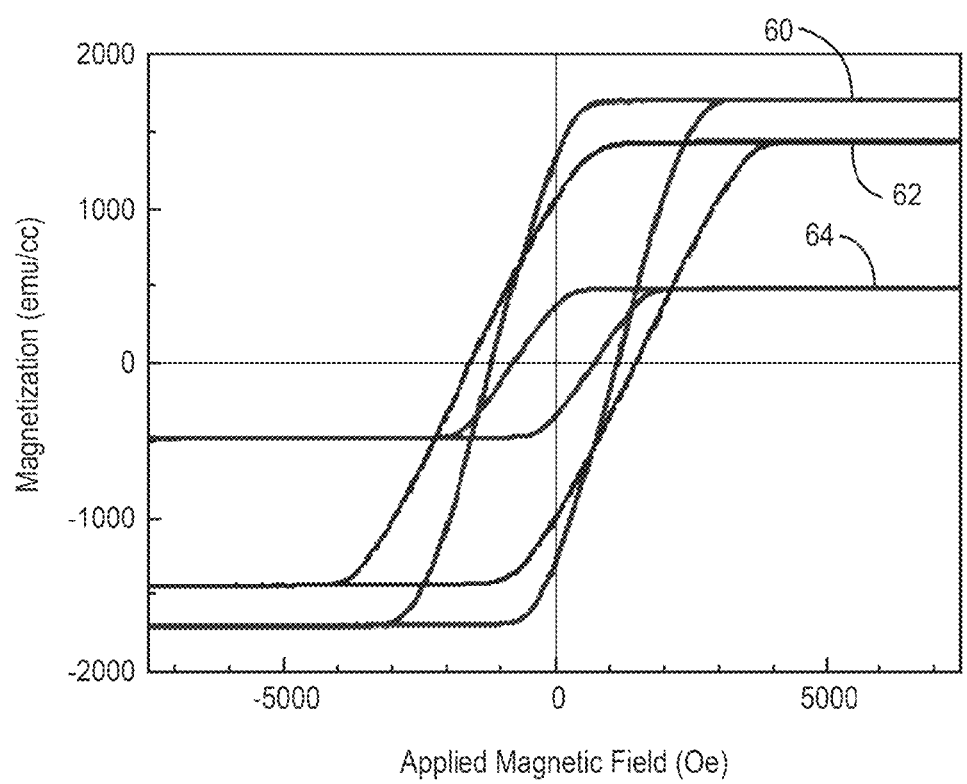
FIG. 6 is a graphical representation of example data pertaining to an application of an example technique for characterizing MNWs in accordance with this disclosure.

FIG. 6 is a graphical representation of data pertaining to an application of an example technique for characterizing MNWs in accordance with this disclosure. In some examples, it may be desirable to determine magnetic characteristics of one or more types of MNWs by obtaining hysteresis curves for the MNWs, as illustrated in FIG. 6. In this example, hysteresis curves for a Fe MNW array 60, a Co MNW array 62, and a Ni MNW array 64 were obtained by applying a magnetic field to the MNW array via a magnetic field source, such as a VSM, and are shown in FIG. 6. From these curves, the saturation magnetization (M) was calculated for each of MNW arrays 60, 62, and 64 as follows: Ni: 0.6 T (485 emu/cc). Fe: 2.1 T (1707 emu/cc), and Co: 1.8 T (1440 emu/cc). The characterization of MNW arrays by the calculation of the saturation magnetization of such MNW arrays (e.g., MNW arrays 60, 62, and 64) may then be used in the FMR identification of such MNWs in association with an object or a sample.

Figure 7:
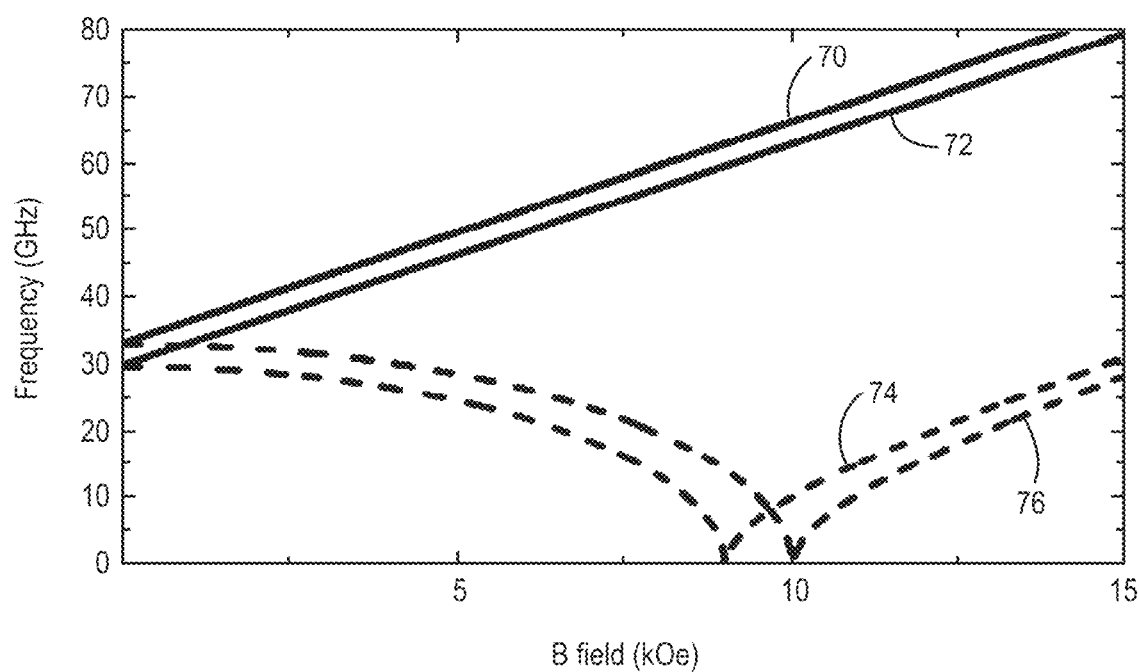
FIG. 7 is a graphical representation of example data pertaining to an application of another example technique for characterizing MNWs in accordance with this disclosure.

FIG. 7 is a graphical representation of data pertaining to an application of another example technique for characterizing MNWs in accordance with this disclosure. A key characteristic of MNWs is their anisotropy. Effective anisotropy field consists of shape anisotropy, magneto-crystalline anisotropy, magnetoelastic anisotropy and magnetostatic interaction field. Take a long (aspect ratio>25) Co MNW with face centered cubic (fcc) structure as an example. Shape anisotropy in this specific MNW dominates. Its effective anisotropy field equals the demagnetization field if a magnetic field is applied along MNW axis. When it is subjected to a high frequency magnetic field, FMR will be excited under the following specific criteria:

$$\left(\frac{\omega}{\gamma}\right)^2 = [H\cos(\theta - \theta_H) + H_{eff}\cos 2\theta][H\cos(\theta - \theta_H) + H_{eff}\cos^2\theta], \quad (2)$$

where $\theta_H$ is the angle between magnetization orientation and the MNW axis and $\theta$ is the angle between external H field and MNW axis. FIG. 7 illustrates the calculated FMR frequency of example Co MNWs 1 and 2 based on Equation 2; i.e., that calculated FMR for a single Co MNW1 with $H_{eff1}$=9.05 kOe (lines 72, 74) and a single Co MNW with $H_{eff2}$=10 kOe (lines 70, 76). Solid lines are FMR with H field along MNW axis and dashed curves are FMR with H field orthogonal to MNW axis. FIG. 7 demonstrates the shift of FMR with respect to material $H_{eff}$ change and also shows the frequency and B field range for single or sparse MNW characterization.

Figure 8:
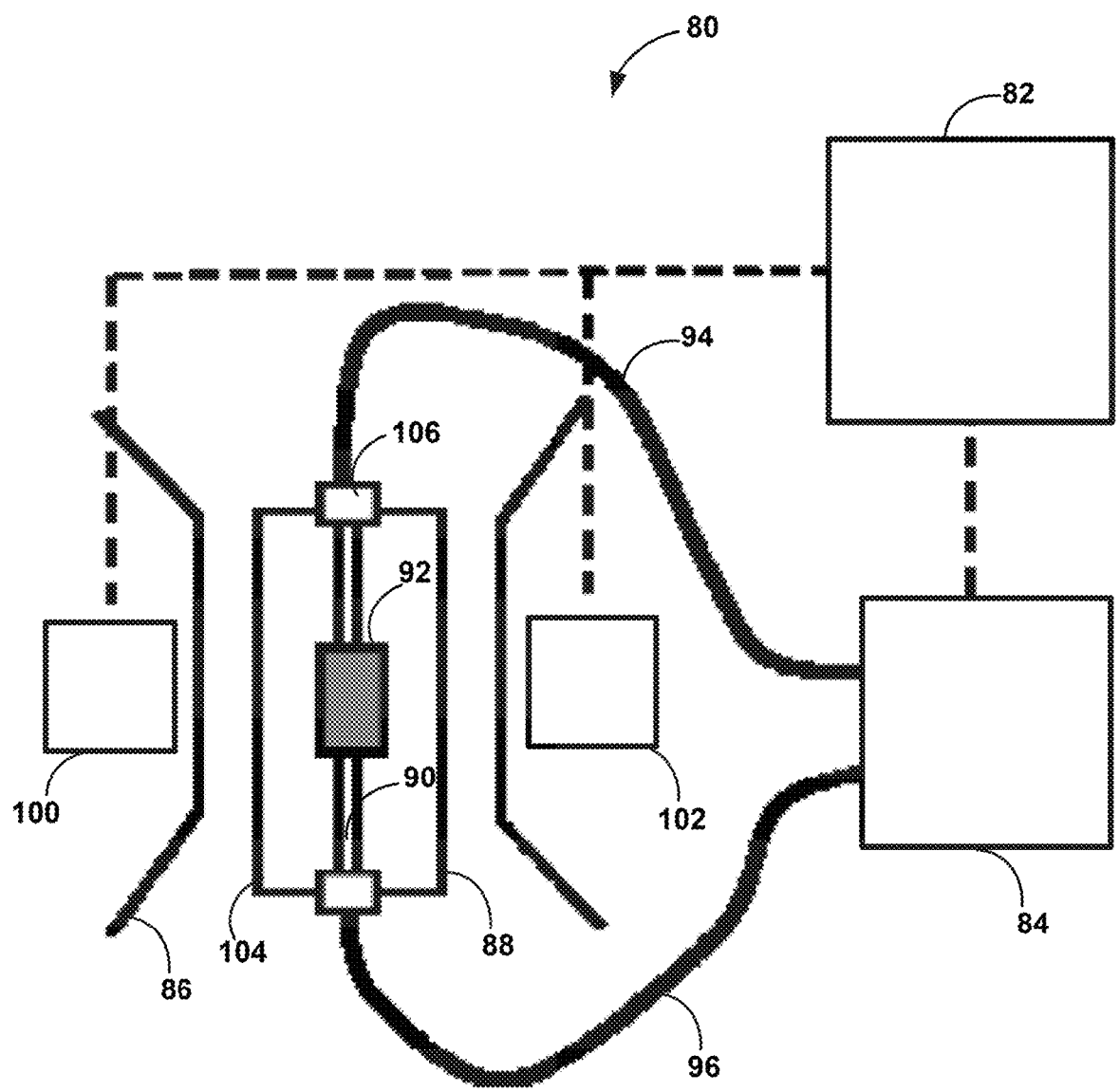
FIG. 8 is a graphical representation of an example configuration of an FMR detection system that may be used to implement the FMR measurement techniques described herein.
Figure 9:
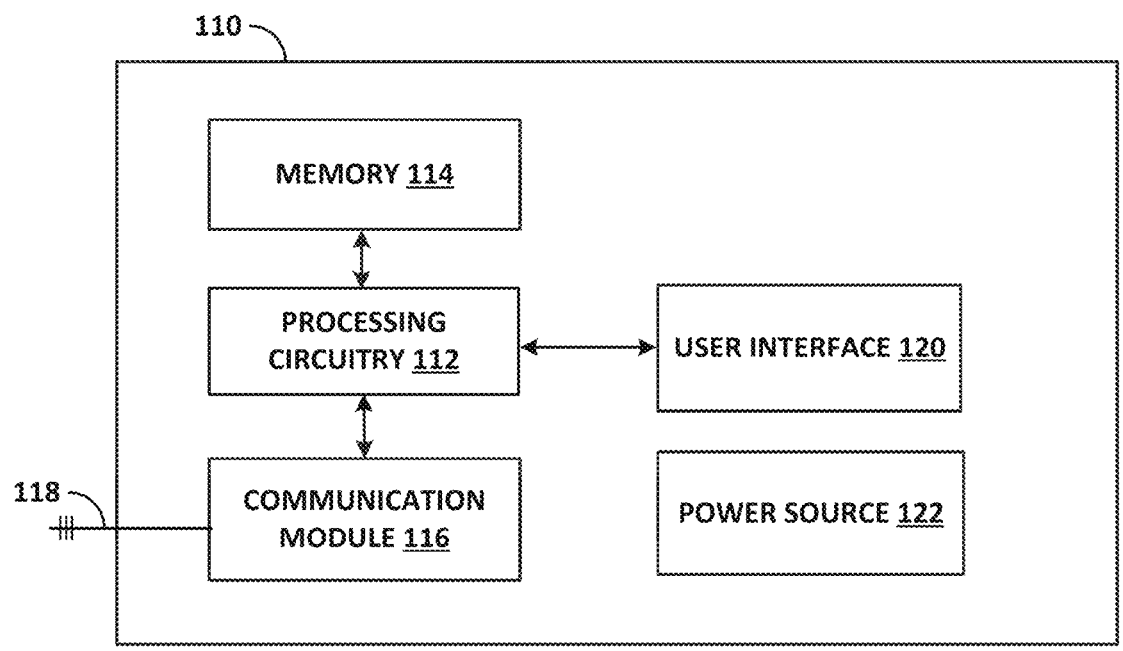
FIG. 9 is a functional block diagram illustrating an example configuration of a computing device that may be used to implement the MNW characterization and identification techniques described herein.

FIGS. 8-18 illustrate example results of MNW FMR identification carried out using the example experimental system illustrated in FIGS. 8 and 9 and example algorithms for identifying MNW types based on measured and known properties of magnetic materials of the MNWs. To quantify magnetic properties of MNWs, measurements like hysteresis loops, first order reversal curves (FORC), and FMR can be applied. Among them, FORC and FMR measurements can reveal the characteristics of multiple MNW types. In one experimental result, different mixtures of two types of nickel MNWs, FORC data showed distinguishable coercivity differences. However, some disadvantages of FORC and other approaches using vibrating sample magnetometry (VSM) are the slow measurement process and the low sensitivity. FMR measurements, on the other hand, detect the unique FMR frequencies of different MNWs, and may provide faster measurements with higher sensitivity. FMR measurement techniques on MNWs have been demonstrated on microstrip and CPW topologies. To enhance sensitivity, a cavity resonator and a CPW-based interferometer also may be implemented. As described below, tuning bandwidth, CPW-based measurement technique is employed. In the examples described herein, FMR may be measured by placing MNWs on top of a CPW board to detect nulls in the transmission response $S_{21}$. Other mechanisms are also captured during the FMR measurement at low field strength, such as the low field absorption (LFA) which corresponds to a broad-linewidth absorption centered at zero kOe.

FIG. 8 is a graphical representation of an example configuration of an FMR detection system 80 that may be used to implement the FMR measurement techniques described herein. FMR detection system 80 includes computing device 82, VNA 84 to provide a microwave power source, and chamber 86. CPW board 88 with through-channel 90 provides magnetic field $H_{AC}$ through sample 92, which may be placed on CPW board 88 within chamber 86. System 80 further includes electromagnets 100, 102, which are configured to apply a DC magnetic field $B_{DC}$ perpendicular to CPW board 88. CPW board 88 may be coupled to VNA 84 with nonmagnetic cables 94, 96 via nonmagnetic end-launch connectors 104, 106. The electromagnet sweep range of system 80 during FMR analysis of sample 92 may be from about +1.5 T to −1.5 T with ramp rate of 250 Oe/s, in some examples. Other magnetic field strengths may be used for other example materials or NMW configurations. The output frequency of VNA 84, in continuous wave (CW) mode, increments from 5 GHz to 40 GHz, for example, with an interval of 1 GHz after each sweep. The reflection ($S_{11}$) and transmission ($S_{21}$) data is obtained by computing device 82 every 0.2 s. In other examples, different frequencies may be used based on the type of material(s) or dimensions used to construct the MNW.

FIG. 9 is a functional block diagram illustrating an example configuration of a computing device 110 that may be used to implement the MNW characterization and identification techniques described herein. For example, computing device 110 includes processing circuitry 112, which may be configured to carry out such MNW characterization and identification techniques, such as receiving data pertaining to characteristics of MNWs and characterizing or identifying MNWs based on such characteristics and/or identifying objects associated with MNWs based on such characteristics. Computing device 110 further includes a memory 114, which may be configured to store data pertaining to characteristics of MNWs, such as FMR characteristics, magnetic transmission characteristics, MNW configurations, and other data pertaining to the characterization and identification of MNWs and/or the identification of objects associated with MNWs. Computing device 110 may further include a communication module 116, which may be configured to receive data from other computing devices via an antenna 118 and transmit such data to processing circuitry 112 and a user interface 120, with which a user may interact to control computing device 110, such as based on data received from such other computing devices. Computing device 110 also may include power source 122, which may be any suitable power source (e.g., a rechargeable or non-rechargeable battery).

FIGS. 10A-10D illustrate different configurations of CPW boards that may be used with system 80 of FIG. 8. CPW boards used with system 80 may have different configurations (e.g., topologies). For example, a through-channel of such CPW boards may have a straight-line configuration or may have a Z-shaped configuration, as described in further detail below. FIGS. 10A-10D are described in the context of an experiment carried out on such CPW boards to investigate the fields distribution inside MNW array samples when placed on through-line and Z-shape board and with static magnetic field in both in-plane (IP) and out-of-plane (OOP) directions and examined the impact of board topologies and MNW array topologies on FMR. However, the concepts and results described with respect to the experiment of FIGS. 10A-10D may be applicable to any CPW boards used in the FMR analysis any of arrays of MNWs of any of the MNW types described herein.

FIG. 10A is a graphical representation of magnetic field distributions at an A-B cross-section on a through-line CPW board 140 with DC magnetic field transmission $B_{DC}$ in the easy axis. A sample MNW array 148 is illustrated atop through-line CPW board 140, with $B_{DC}$ 150 depicted as arrows and AC magnetic field transmission $H_{AC}$ 152 depicted as ovals. FIG. 10B is a graphical representation of magnetic field distributions at an A-B cross-section on through-line CPW board 140 of FIG. 10A with $B_{DC}$ in the hard axis. FIG. 10C is a graphical representation of magnetic field distributions at an A-B cross-section on a Z-shape CPW board 156 with $B_{DC}$ in the easy axis, and FIG. 10D is a graphical representation of magnetic field distributions at an A-B cross-section on Z-shape CPW board 156 of FIG. 10C with $B_{DC}$ in the hard axis.

With OOP $B_{DC}$ inside sample 148, through-line CPW board 140 as shown in FIG. 10A and Z-shape CPW board 156 as shown in FIG. 10C have the same $H_{AC}$ and $B_{DC}$ orientation, which may produce similar results. With IP $B_{DC}$, however, through-line CPW board 140, shown in FIG. 10B, may have a portion of $H_{AC}$ parallel to $B_{DC}$ inside sample 148, which cannot contribute to FMR absorption. Z-shape CPW board 156 as shown in FIG. 10D, however, maintains constant orthogonality between $B_{DC}$ and $H_{AC}$ inside sample 148, which may enhance FMR absorption. Measured magnitude of $S_{21}$, shown in FIG. 11A and discussed below, confirms the enhancement. With Z-shape board 156, an FMR with peak amplitude of 0.01 is observed at 11.8 kOe; whereas with through-line CPW board 140, the absorption at the same bias magnetic field is not detectable. Thus, in some examples, it may be advantageous to use a Z-shape CPW board (e.g., Z-shape CPW board 156) in the characterization and identification of FMR characteristics of MNWs, such as in examples in which an $S_{21}$ signal strength is low due to low MNW concentration or other factors.

Figure 11A:
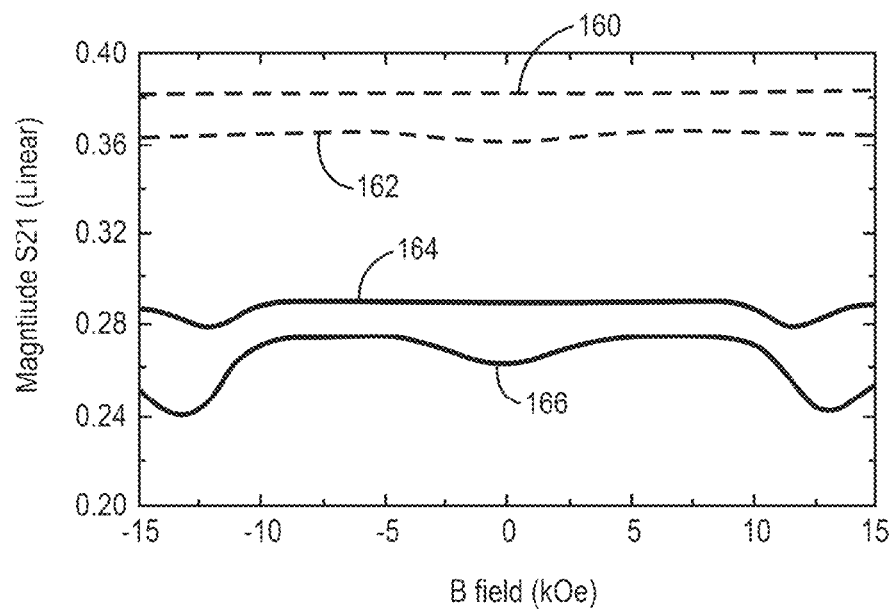
FIGS. 11A and 11B are graphical representations of example effects of different MNW array topologies on magnetic transmission magnitude and FMR characteristics in accordance with examples of this disclosure.
Figure 11B:
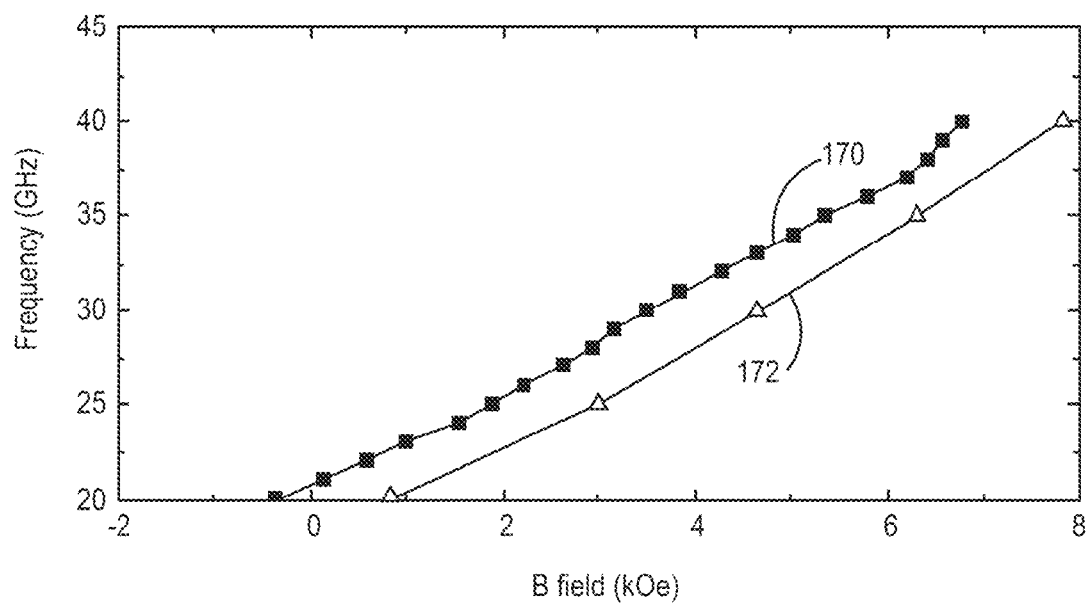

FIGS. 11A and 11B are graphical representations of effects of different MNW array topologies on magnetic transmission magnitude and FMR characteristics of the MNW array in accordance with examples of this disclosure. As with a Z-shape CPW board, the inclusion of a Cu layer in an MNW array may, in some examples, may enhance the magnitude of $S_{21}$ measured during FMR analysis of the MNW array, which may facilitate the characterization and/or identification of MNWs in examples in which a $S_{21}$ signal strength is low.

FIG. 11A is a graphical representation of the enhancement of the measured magnitude of $S_{21}$ that may result from the inclusion of a Cu layer in the CPW board relative to both through-line and Z-shape CPW topologies (e.g., through-line CPW board 140 of FIGS. 10A and 10B and Z-shape CPW 156 of FIGS. 10C and 10D). Besides connecting all the MNWs in the Co MNW array or other MNW arrays, a Cu layer may affect the field distribution provided by CPW board. When testing a MNW array sample with a Cu layer, the sample is placed with the Cu layer on top and with the AAO side contacting the CPW board. In this setup, the top Cu layer becomes a floating ground plane. The small height of AAO (approx. 50 micrometers) may position the Cu layer closer to the CPW signal line than the adjacent ground planes of the CPW board. Thus, the E-field and the corresponding H-field in a sample are concentrated right above the signal line, with a higher field intensity than the CPW region over the slots.

The graphical representation of FIG. 11A illustrates the relative magnitudes of $S_{21}$ that may be obtained during FMR analysis of a Co MNW array that either includes or does not include a Cu layer, and which is measured on either a through-line CPW board or a Z-shape CPW board. FIG. 11A illustrates magnitudes of $S_{21}$ that may be obtained during analysis of: a Co MNW array including a Cu layer and is measured on a Z-shape CPW board (dashed line 160), a Co MNW array that does not include a Cu layer and is measured on Z-shape CPW board (dashed line 162), a Co MNW array that includes a Cu layer and is measured on a through-line CPW board (dashed line 162), a Co MNW array that does not include a Cu layer and is measured on through-line CPW board (solid line 164), and a Co MNW array that does not include a Cu layer and is measured on through-line CPW board (solid line 166).

As shown in FIG. 11A, the magnitude of $S_{21}$ during FMR measurements is greatest at dashed line 160, which corresponds to the Co MNW array that includes a Cu layer and is measured on a Z-shape. The magnitude of $S_{21}$ transmission associated with a Co MNW array that does not include a Cu layer and is measured on Z-shape CPW board, illustrated by dashed line 162, is greater than a magnitude of $S_{21}$ transmission associated with a Co MNW array that includes a Cu layer and is measured on a through-line CPW board, illustrated by solid line 164. A Co MNW array that does not include a Cu layer and is measured on through-line CPW board, illustrated by solid line 166, is less than a magnitude of $S_{21}$ associated with a Co MNW array that includes a Cu layer and is measured on the through-line CPW board. Thus, the combination of a Z-shape CPW board and a MNW array that includes a Cu layer may provide greater signal absorption (corresponding to lesser signal transmission), and thus potentially easier and/or more accurate MNW FMR analysis than through-line CPW boards and/or MNW arrays that do not include a Cu layer.

In addition to field intensity boost, the presence of the additional Cu layer may affect an FMR characteristic of a sample. FIG. 11B is a graphical representation of a shift in a frequency at which FMR occurs for a given $B_{DC}$ for Co MNW arrays, which summarizes the OOP FMR measurements for a Co68 MNW array 170 (with Cu layer) and a Co72 MNW array 172 (without Cu layer) from 20 to 40 GHz. Throughout the frequency range, corresponding B fields in these two samples differ approximately 1 kOe. It suggests there is a change of internal $H_{eff}$ inside the sample with the Cu layer connection. FIGS. 11A and 11B thus illustrate the shifts in $S_{21}$ and FMR characteristic that may occur with MNW arrays that include a Cu layer relative to MNW arrays that do not include a Cu layer. In some examples, processing circuitry of a computing device (e.g., processing circuitry 112 of computing device 110) configured to analyze $S_{21}$ and FMR measurements of a sample may account for the presence or absence of a Cu layer of a MNW when determining values pertaining to such MNW arrays.

Figure 12B:
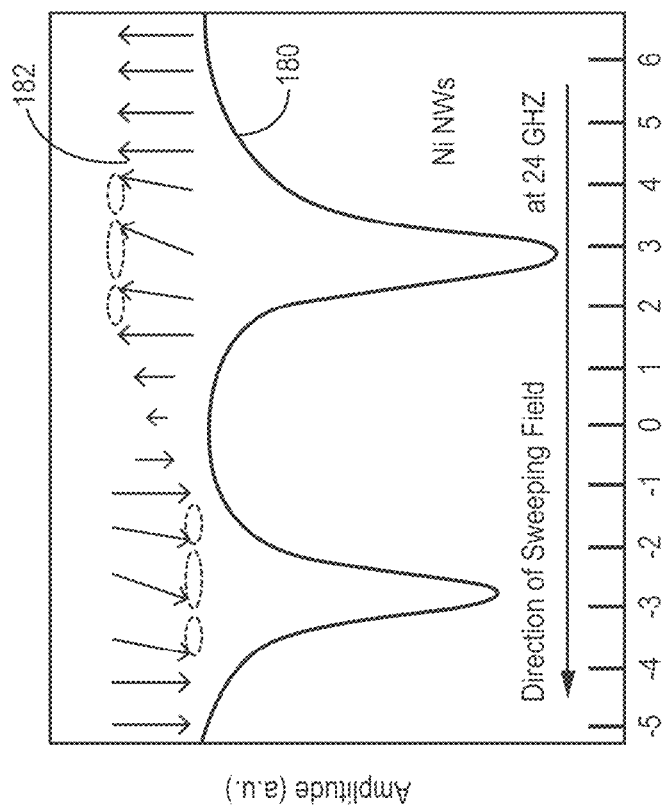
FIGS. 12A and 12B are graphical representations of example data pertaining to an application of an example technique in accordance with this disclosure.
Figure 12A:
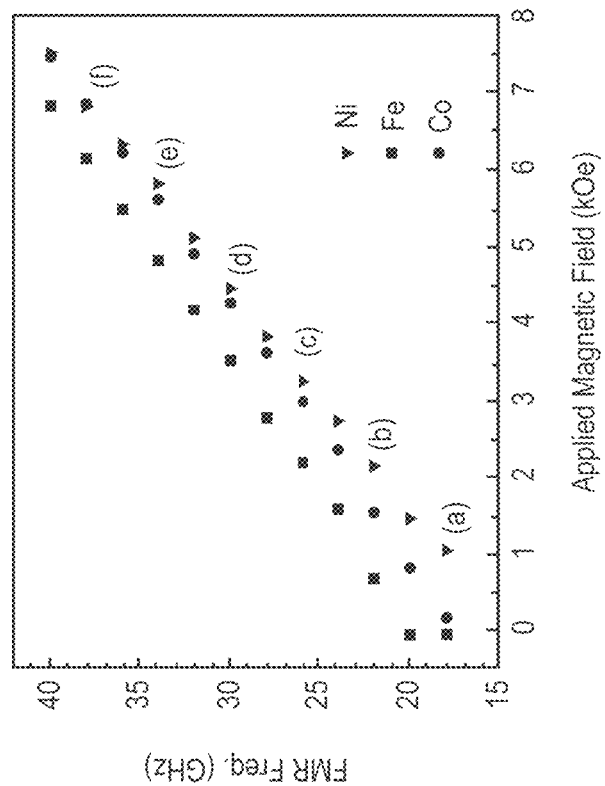

FIGS. 12A and 12B are graphical representations of data pertaining to an application of an example technique in accordance with this disclosure. FIG. 12A illustrates differences in FMR trends that may be associated with different types of MNWs, such as Ni, Fe, and Co MNWs. FMR occurs when a frequency of an applied microwave (GHz) and a strength of an applied magnetic field kOe are equal. As illustrated in FIG. 12A, FMR may occur at multiple combinations of microwave frequency and strength of magnetic field for each of the different types of MNWs, as denoted by triangles pertaining to Ni MNWs, squares pertaining to Fe MNWs, and circles pertaining to Co MNWs in the chart of FIG. 12A.

Moreover, as shown in FIG. 12A, for a plurality of types of MNWs such as Ni, Fe, and Co, the points at which FMR occurs for two or more of the types of MNWs may be closer together at some portions of the range than others. For example, the points at which FMR occurs for Ni and Co are further apart at points having relatively lower GHz and lower kOe than at points having relatively higher GHz and kOe. Because it may be easier for processing circuitry of a computing device (e.g., processing circuitry 112 of computing device 110) to distinguish between FMR characteristics of different types of MNWs that are spaced relatively farther apart, this observation may help inform GHz and kOe at which a FMR detection system may operate when conducting an FMR scan of a sample or object. In such a manner, FMR detection systems and computing devices configured to carry out the MNW characterization and identification techniques described herein may distinguish between FMR characteristics of different types of MNWs, as further described below with respect to FIGS. 16A-18B.

FIG. 12B illustrates example changes in $S_{21}$ transmission amplitude 180 and changes in spin 182 of a MNW array that may occur in a Ni MNW array under an applied microwave field of 24 GHz and a sweeping DC magnetic field from about −5 kOe to about 6 kOe, although broader or narrower ranges in DC sweep may be used in other examples. As shown in FIG. 12B, RF signal may be absorbed at two kOe (indicated by a reduction in $S_{21}$ transmission amplitude, which corresponds to an increase in absorption amplitude), symmetric about the kOe origin. Differences in the two peak absorption amplitudes may be attributed to remanence in the ferromagnetic material of the Ni MNW array, which may restrict complete spin reversal with magnetic field reversal. In some examples, MNW types may be selected that have the two peak absorption amplitudes relatively further apart to help enable processing circuitry to distinguish between different types of MNWs, as also further described below with respect to FIG. 13.

Figure 13:
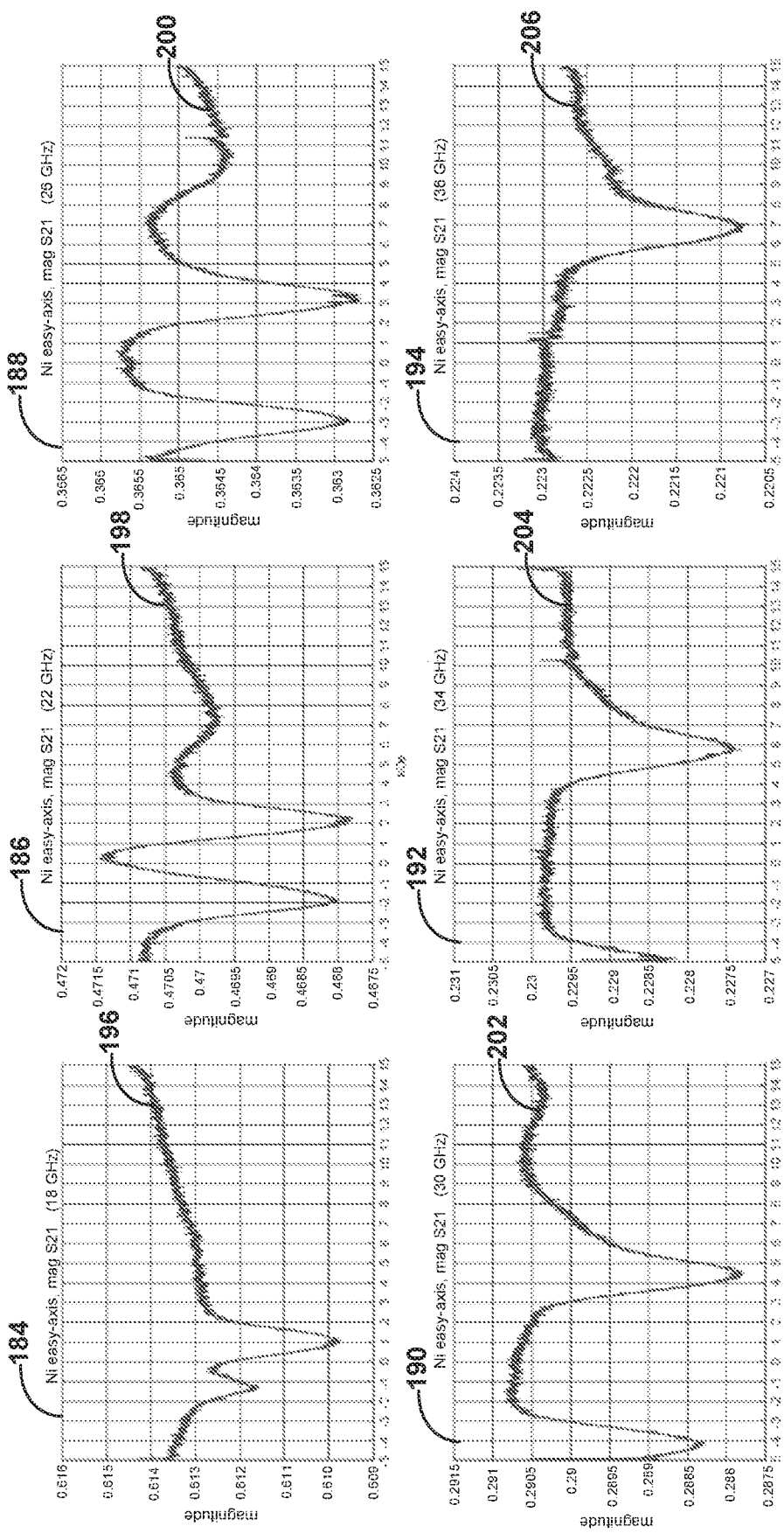
FIG. 13 is a graphical representation of example data pertaining to an application of an example technique in accordance with this disclosure.

FIG. 13 is a graphical representation of data pertaining to an application of an example technique in accordance with this disclosure. FIG. 13 includes six charts 184, 186, 188, 190, 192, and 194 that illustrate changes in $S_{21}$ amplitude of an example Ni MNW array that occur when the Ni MNW array is subjected to respective microwave fields of 18 GHz, 22 GHz, 26 GHz, 30 GHz, 34 GHz, and 38 GHz when an applied DC magnetic field is swept from about −5 kOe to about 15 kOe. As illustrated by $S_{21}$ amplitudes 196, 198, 200, 202, 204, and 206, which respectively correspond to the microwave fields of 18 GHz, 22 GHz, 26 GHz, 30 GHz, 34 GHz, and 38 GHz, the spacing of the peak absorption amplitudes of the Ni MNW array change (i.e., occur at increasingly different kOe) with changes in the frequency of the applied microwave field.

FIGS. 14A-18B illustrate aspects of example techniques for identifying different types of MNWs from within a mixture of MNWs. Such techniques may be advantageous to numerous applications of MNWs as nanoscale labels. For example, some such applications may involve the use of a plurality of types of MNWs, such as examples in which different types of cells are labeled with different types of MNWs and later obtained as a mixture of a fluid sample from a host organism, examples in which multiple parts of an article of manufacture are each labeled with a different type of MNW, or others. As discussed above, FMR is a relatively fast, sensitive method for detecting unique characteristics of types of MNWs. However, when an object or sample containing multiple types of MNWs is subjected to an FMR scan, a single absorption trend representative of the combined microwave absorption trends of the multiple types of MNWs results as an applied DC magnetic field is swept. Thus, provided that characterizing information pertaining to each individual type of MNW is known, algorithms may be used to parse $S_{21}$ absorption trends representative of a combination of absorption trends of different types of MNWs. To demonstrate the concept of labeling with multiple MNW types, it may be important to understand the FMR absorption of each MNW type on AC transmission ($S_{21}$). The model described below to describe MNW FMR absorption is based on Lorentzian function. The Lorentzian function model has been proven accurate in extracting magnetic properties from measurements with both thin-films and MNW arrays. The same model, illustrated by Equation 3 below, may be used for both single MNW type and MNW array identifications:

$$S_{21} = a + bH + \frac{c(H - M_{eff})M_{eff}}{(H - M_{eff})^2 - H_{eff}^2 \pm i\frac{\Delta H}{2}(H - M_{eff})} \quad (3)$$

In Equation 3 for defining transmission $S_{21}$, a, b and c are coefficients. The first two terms model linear drift in a measurement system and the third term is a Lorentzian function that models the FMR absorption with respect to linewidth ($\Delta H$), effective magnetization ($M_{eff}$), effective internal field ($H_{eff}$) of the MNW and the applied external field (H). Some such parameters of a given MNW may be determined during MNW characterization using the example techniques described above, which may be used in measurements pertaining to a plurality of types of MNWs. For example, any of the coefficients (e.g., a, b, or c in Equation 3) may be used, alone or in any combination, as one or more FMR characteristics used to detect and/or identify MNWs described herein.

Figure 14A:
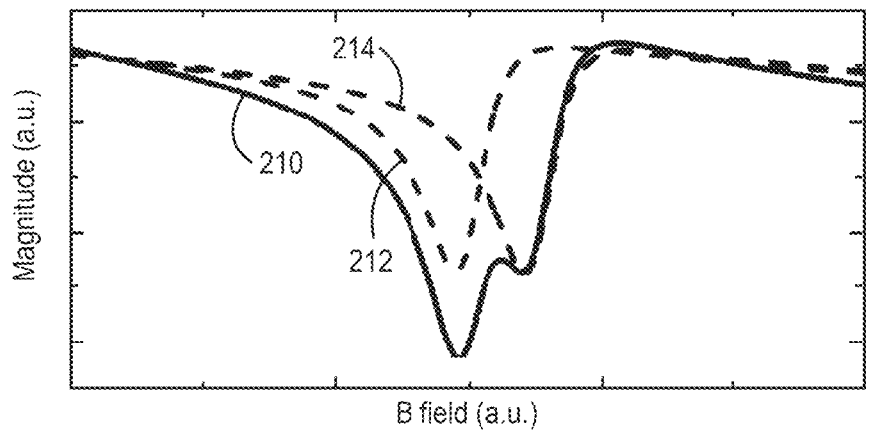
FIGS. 14A-14C are graphical representations of data pertaining to an application of an example technique in accordance with this disclosure.
Figure 14B:
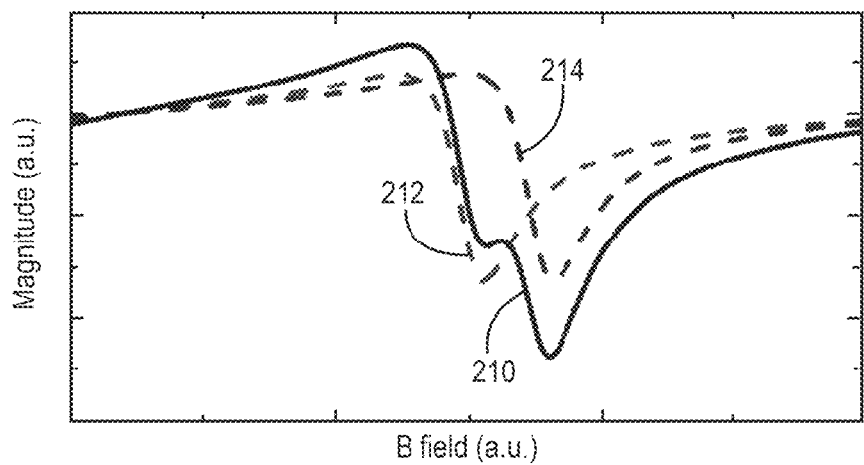
Figure 14C:
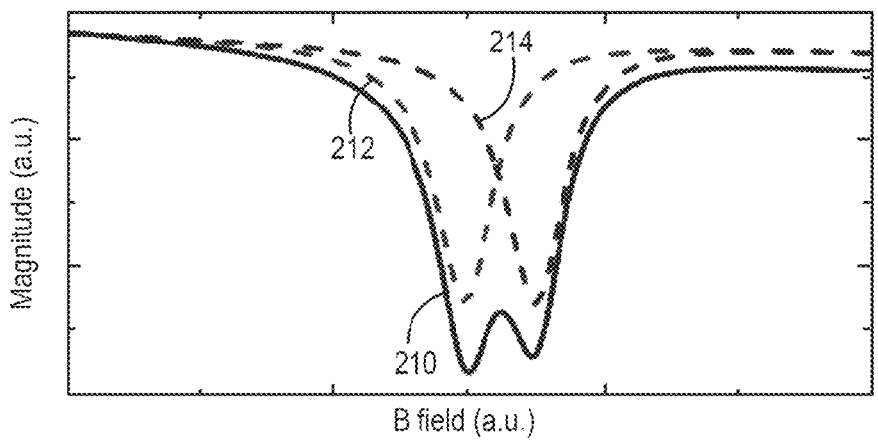

FIGS. 14A-14C are graphical representations of data pertaining to an application of an example technique for identifying a plurality of types of MNWs present in a mixture 220 of types of MNWs in accordance with this disclosure. For a measurement with two types of MNWs, the first two terms of Equation 3 remain the same, while the third term becomes the addition of two sets of Lorentzian functions, referred to as mixed $S_{21}$. FIG. 14A illustrates the real portion of overall $S_{21}$ response 210 of two magnetic materials, MNW type 1 and MNW type 2, which respectively correspond to component $S_{21}$ responses 212 and 214, whose effective internal fields ($H_{eff}$) differ by half the linewidth, $H_{eff1} - H_{eff2} = 0.5\Delta H$. FIG. 14B illustrates the imaginary portion of overall $S_{21}$ response 210 and component responses 212 and 214. As illustrated in FIGS. 14A and 14B, although the two MNW types share highly similar magnetic properties, the real and imaginary parts of the mixed $S_{21}$ do not show high similarity. However, FIG. 14C, which illustrates the magnitude of $S_{21}$ with component responses 212 and 214 separated by 0.5 linewidth, shows a direct connection to the two individual MNW nulls corresponding to FMR of MNW type 1 and FMR of MNW type 2. For this reason, most of the data described below with respect to the identification of MNWs present in a mixture of a plurality of types of MNWs is presented in magnitude format.

$M_{eff}$, $H_{eff}$ and $\Delta H$ are the common set of parameters that describe magnetic material properties in both single and multiple MNW types measurements. These three parameters can be extracted from the fitting of Equation 3 to the measurement data of each individual MNW type. Then, extracted parameters are used to interpret the measured $S_{21}$ of multiple MNW types. Given a set of MNW types that assigns a k value and has extracted magnetic parameters as $He_{ff,k}$, $Me_{ff,k}$, $\Delta Hk$, (k=1 . . . n) for the properties of each MNW type, the transmission coefficient expression of the mixture of MNW types is as follows:

$$S_{21} = a + bH + \sum_{k=1}^{n} \frac{c_k(H - M_{eff,k})M_{eff,k}}{(H - M_{eff,k})^2 - H_{eff,k}^2 \pm i\frac{\Delta H_k}{2}(H - M_{eff,k})} \quad (4)$$

By fitting Equation 4 to measured $S_{21}$ for the mixture of MNWs, the coefficient ck for each MNW array type may be extracted. To determine whether a specific MNW type is present, processing circuitry of a computing device (e.g., processing circuitry 112 of computing device 110) may determine whether the back-fitted ck is significant. If the back-fitted ck is significant, then the processing circuitry may determine that the corresponding type of MNW is present in the mixture of the plurality of types of MNWs. In some examples, a global optimization function may be programmed to fit $S_{21}$ mathematical model Equations 3 and 4 to the measured data with a least square error term. Since $S_{21}$ is a complex number, the overall error term equals the summation of the error from both real and imaginary terms. Therefore, in this example, the back-fitted ck coefficient may be used as an FMR characteristic in some examples.

Figure 15:
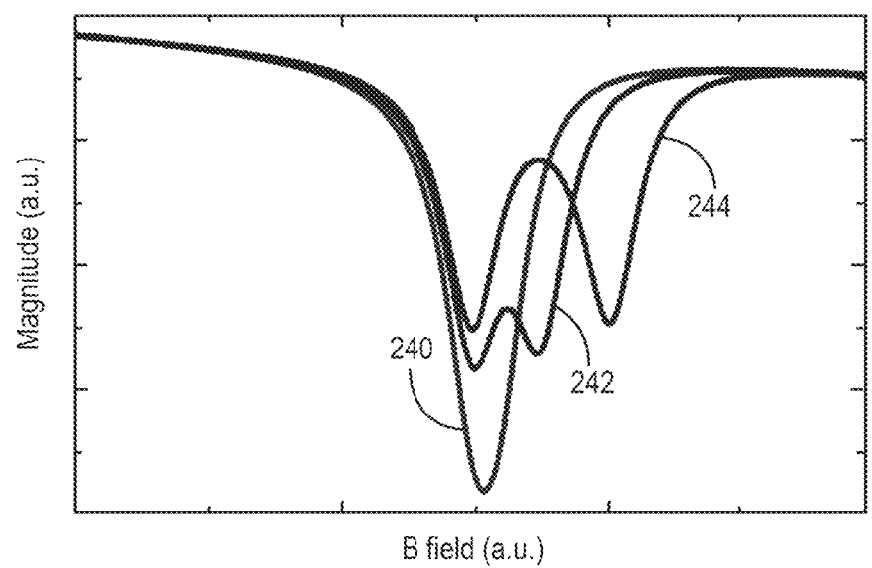
FIG. 15 is a graphical representation of data pertaining to an application of an example technique in accordance with this disclosure.

FIG. 15 is a graphical representation of data pertaining to an application of an example technique in accordance with this disclosure. As illustrated in FIG. 15, $S_{21}$ nulls of MNW types may have varying $dH_{eff}$ of 0.2$\Delta H$, 0.5$\Delta H$ and 1$\Delta H$. In systems having enlarged spacing between each FMR signal, such as with increased spacing from 0.2$\Delta H$ (240) to 0.5$\Delta H$ (242) to 1$\Delta H$ (244), the superposition of FMR absorption may be mitigated and thus sensitivity may be improved. In some examples labeling systems using MNWs, such as in biolabeling or other example applications, tuning FMR spacing between each type of MNW to be used in the labeling system may help enable the different types of MNWs to be differentiated from one another based on their different FMR signatures.

Figure 16A:
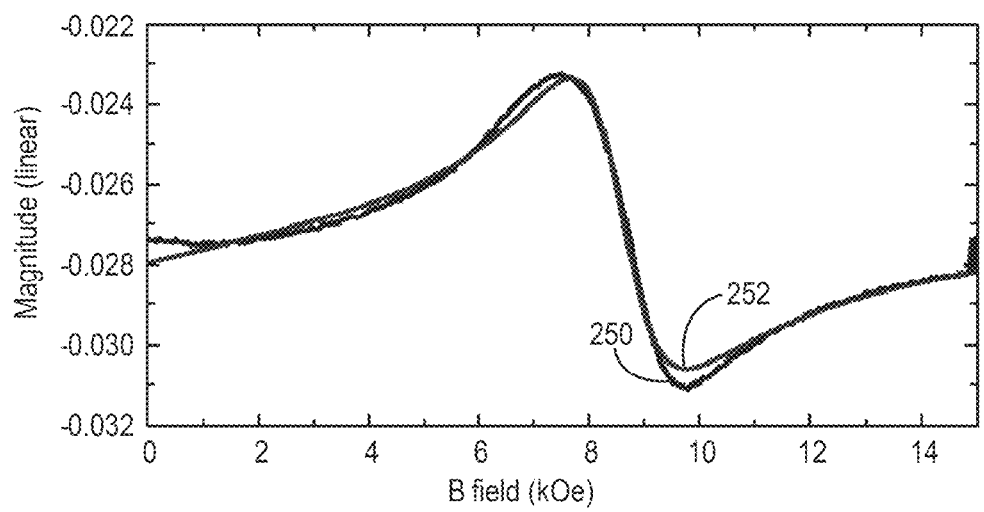
FIGS. 16A and 16B are graphical representations of data pertaining to an application of an example technique in accordance with this disclosure.
Figure 16B:
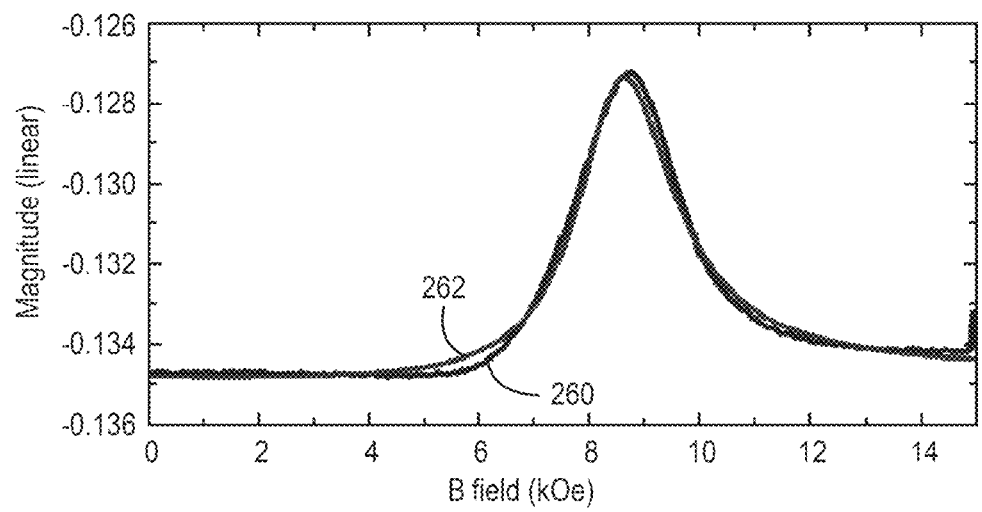

FIGS. 16A and 16B are graphical representations of data pertaining to an application of an example technique in accordance with this disclosure. FIG. 16A is an illustration of the real part of measured (250) and Lorentzian function fitted (252) S21 of Co72 MNWs with OOP $B_{DC}$ at 40 GHz. FIG. 16B is an illustration of the imaginary part of measured (250) and Lorentzian function fitted (252) $S_{21}$ of the Co72 MNWs with OOP BDC at 40 GHz. As described above, the Lorentzian function is applied to extracting the magnetic parameters ($M_{eff}$, $H_{eff}$ and $\Delta H$) from the measured $S_{21}$. For clarity, these parameters are described in kOe in the Lorentzian function fitting equation. Collectively, FIGS. 16A and 16B compare raw $S_{21}$ data and the mathematical model for Co72 MNWs and illustrate that the Lorentzian model captures the whole shape of the FMR absorption, showing a strong correlation for between raw data and the mathematical model for the Co72 MNWs. In the same manner, $M_{eff}$, $H_{eff}$ and $\Delta H$ for Fe49 MNWs and Ni 62 may be extracted and summarized.

FIGS. 17A and 17B are graphical representations of multiple types of MNW samples arranged on a CPW board in accordance with this disclosure. FIG. 17C is a graphical representation of a comparison of data obtained via an application of an example MNW identification technique to the multiple types of MNW samples FIGS. 17A and 17B with known data pertaining to individual MNW types. The techniques described above for the identification of MNW types out of a mixture has two parts. The first part may include acquiring magnetic properties related parameters ($M_{eff}$, $H_{eff}$ and dH) from individual MNW type FMR measurements, as described above. The second part may include feeding these parameters into Equation 4 to extract the coefficients (ck), which then may be associated with each specific type of MNWs present in a mixture of a plurality of types of MNWs.

In the example of FIG. 17A, a multiple-MNW stack 260 containing Fe49 MNWs 262, Co72 MNWs 264, and Ni62 MNWs 266 are positioned over a CPW board 268. In the example of FIG. 17B, a multiple-MNW stack 270 containing Co72 MNWs 272, Fe49 MNWs 274, and Ni62 MNWs 276 are positioned over a CPW board 278, which may be substantially similar to CPW board 268. Direct contact of magnetic material between MNW array samples may be avoided by underfilled AAO templates positioned between MNW array samples within stacks 260, 270.

As illustrated in FIG. 17C, the parameters of Co72 MNWs 264, 272, Fe49 MNWs 262, 274 and Ni62 MNWs 266, 276 may be extracted from their individual measurements. Normalized $S_{21}$ magnitude of Co72 (280), Fe49 (282), Ni62 (dashed cyan) and multiple MNW arrays stack configurations (Ni62-Co72-Fe49 (286) and Ni62-Fe49-Co72 (288)) measured with OOP BDC at 40 GHz. First, the FMR null locations of each individual MNW arrays line up with the locations in the stacked cases. Second, comparing the two stacked cases, with Co72 sandwiched between Ni62 and Fe49 three nulls are observed, while with Fe49 sandwiched only two nulls are observed.

One method of identifying MNW types is to search for nulls in magnitude of transmission coefficient $S_{21}$ plots. Another method to discern FMR presence, as described herein, is to evaluate the extracted coefficient ck from the fitting of Equation 4. The following Table 2 summarizes the coefficients of Co72, Fe49 and Ni62 MNW arrays in the two stacked configurations of stacks 260, 270, in which data are presented in magnitude/phase format to show a direct indication of FMR null depth:

TABLE 2

COEFFICIENT (CK) EXTRACTED FROM
FITTING EQUATION 3 (×10⁻⁴)

| Test Configuration | Co72 | Fe49 | Ni62 |
|---|---|---|---|
| Ni62-Fe49-Co72 | 16∠−14° | 90∠1° | 20∠9° |
| Ni62-Co72-Fe49 | 25∠60° | 38∠45° | 19∠56° |

Figure 18A:
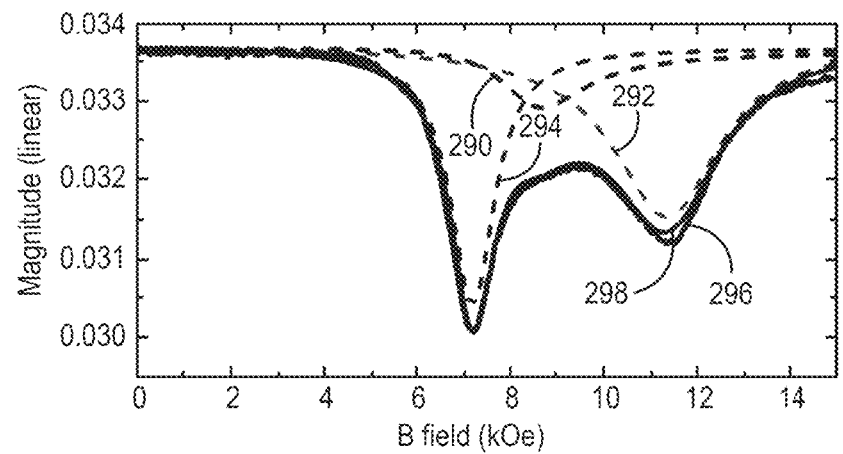
FIGS. 18A and 18B are graphical representations of raw data and fitted data pertaining to the MNW stacks 260, 270 of FIGS. 17A and 17B in accordance with this disclosure.
Figure 18B:
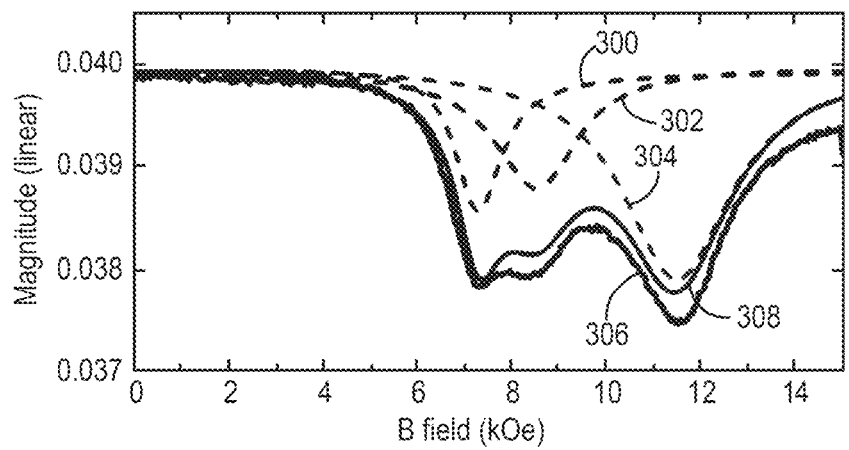

FIGS. 18A and 18B are graphical representations of raw data and fitted data pertaining to MNW stacks 260 and 270 of FIGS. 17A and 17B, respectively. Magnitudes of $S_{21}$ for each MNW array sample, having ck listed in Table 4 and having the same linear terms, are also plotted in FIGS. 18A and 18B to show the contribution of each MNW type to the overall $S_{21}$ magnitude shape. In FIG. 18A, Co $S_{21}$ is illustrated by curve 290, Ni $S_{21}$ is illustrated by curve 292, and Fe $S_{21}$ is illustrated by curve 294. In FIG. 18B, Co $S_{21}$ is illustrated by curve 302, Ni $S_{21}$ is illustrated by curve 304, and Fe $S_{21}$ is illustrated by curve 306.

FIG. 18A presents a high correlation between raw data curve 296 and fitting curve 298, even with only two noticeable nulls. In FIG. 18B, there is a gap between raw data curve 306 and fitting curve 308, which indicates a larger error term. Nonetheless, based on Table 4 and FIGS. 18A and 18B, it can be determined that the FMR of all three MNW samples, in both cases, show up in the measured $S_{21}$. Therefore, applying model fitting provides a higher sample identification capability than a MNW identification technique of looking for FMR nulls in $S_{21}$ plots.

Figure 19:
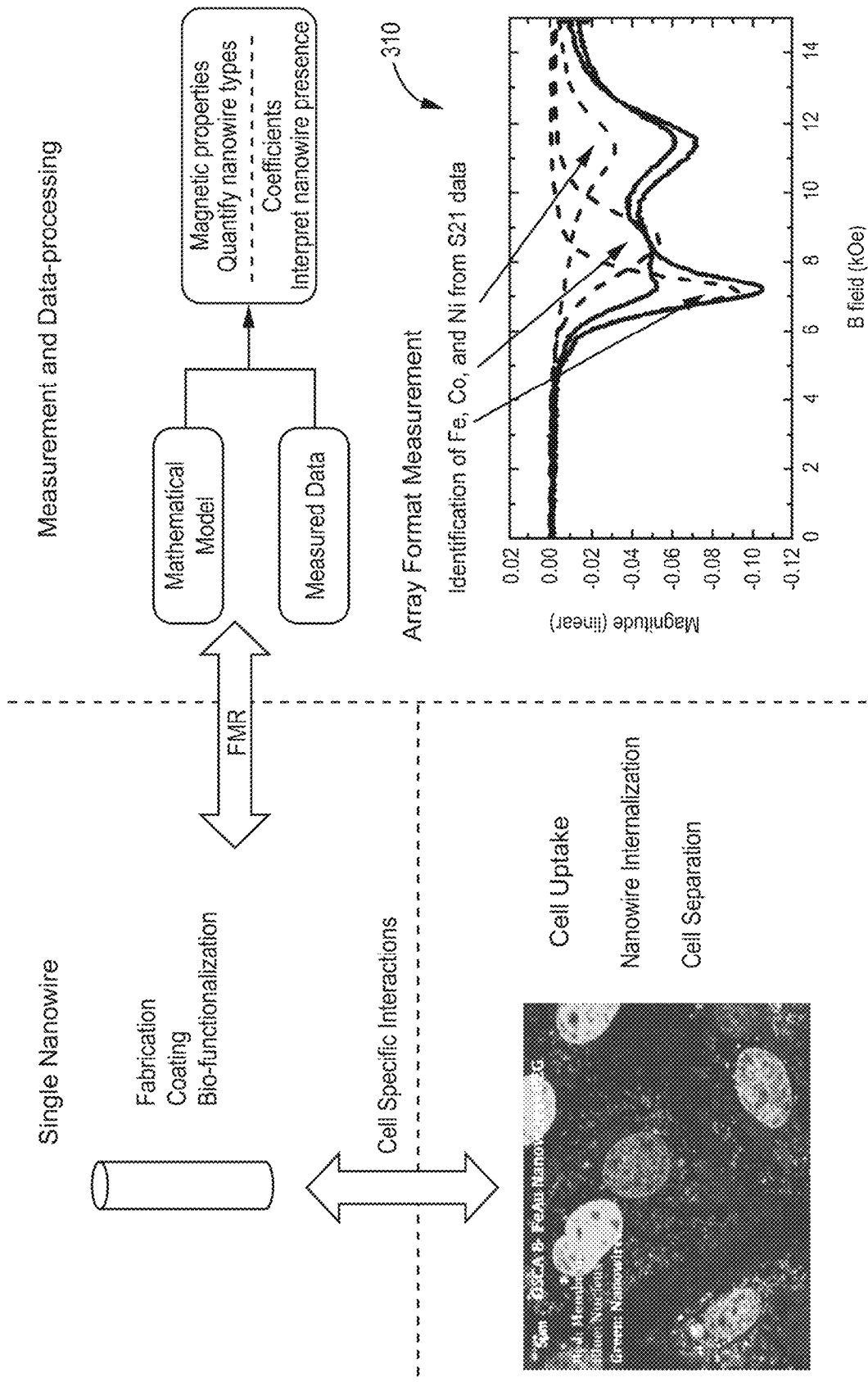
FIG. 19 is graphical representation of an example technique for use of MNWs in a labeling application.

FIG. 19 is graphical representation of an example technique for use of multiple types of MNWs in a biolabeling application, from MNW fabrication to MNW introduction into cells and later isolation therefrom, to identification of MNW types using the techniques described above. Although FIG. 19 illustrates a biolabeling application, the relationship between MNW manufacture, use, and later identification may be substantially similar in other applications of the use of MNWs as nanoscale labels, such as in the labeling of chemical compositions or articles of manufacture, devices, or any other non-biological application. In any such examples, the techniques and systems described above for the manufacture, characterization, and identification of one or more types of MNWs may be applied.

As illustrated in FIG. 19, MNWs (e.g., a single MNW) may be manufactured, such as by wire fabrication (e.g., as described above with respect to FIGS. 1A-3C), and optionally coated with a biocompatible coating, which may be functionalized with a biologically-active compound to help enable the MNW to interact with a cell type or tissue of interest within an organism into which the MNWs are introduced. Following manufacturing, the MNWs may be measured and processed to characterize the MNWs, such as prior to introduction into an organism. As discussed above, the characterization of MNWs may include determining one or more magnetic transmission and/or FMR characteristics of the MNWs, which may help enable later identification of the MNWs (e.g., from a mixture contained within a biological sample).

Next, MNWs may be introduced into tissue derived from a host organism. For example, MNWs may be introduced into a sample of tumor cells derived from a donor animal. Such cells then may take up (i.e., internalize) the MNWs, after which the cells from the donor animal may be introduced into a host organism. Later, biological samples may be obtained from the host organism and processed to separate cells and/or exosomes containing MNWs from cells and/or exosomes that do not contain MNWs or that contain different types of MNWs. Following MNW separation from the biological samples, further measurement and data processing may be carried out, using the models and techniques described above, to identify and, in some examples, quantify, one or more types of MNWs present within the biological samples. The parameters of of each type of MNW of a plurality of MNW types may be extracted from a sample containing a mixture of a plurality of types of MNWs based on the earlier characterization of each type of MNW, as described above with respect to the example of FIG. 17C, which is inset into FIG. 19 as chart 310 for the sake of illustration.

Figure 20:
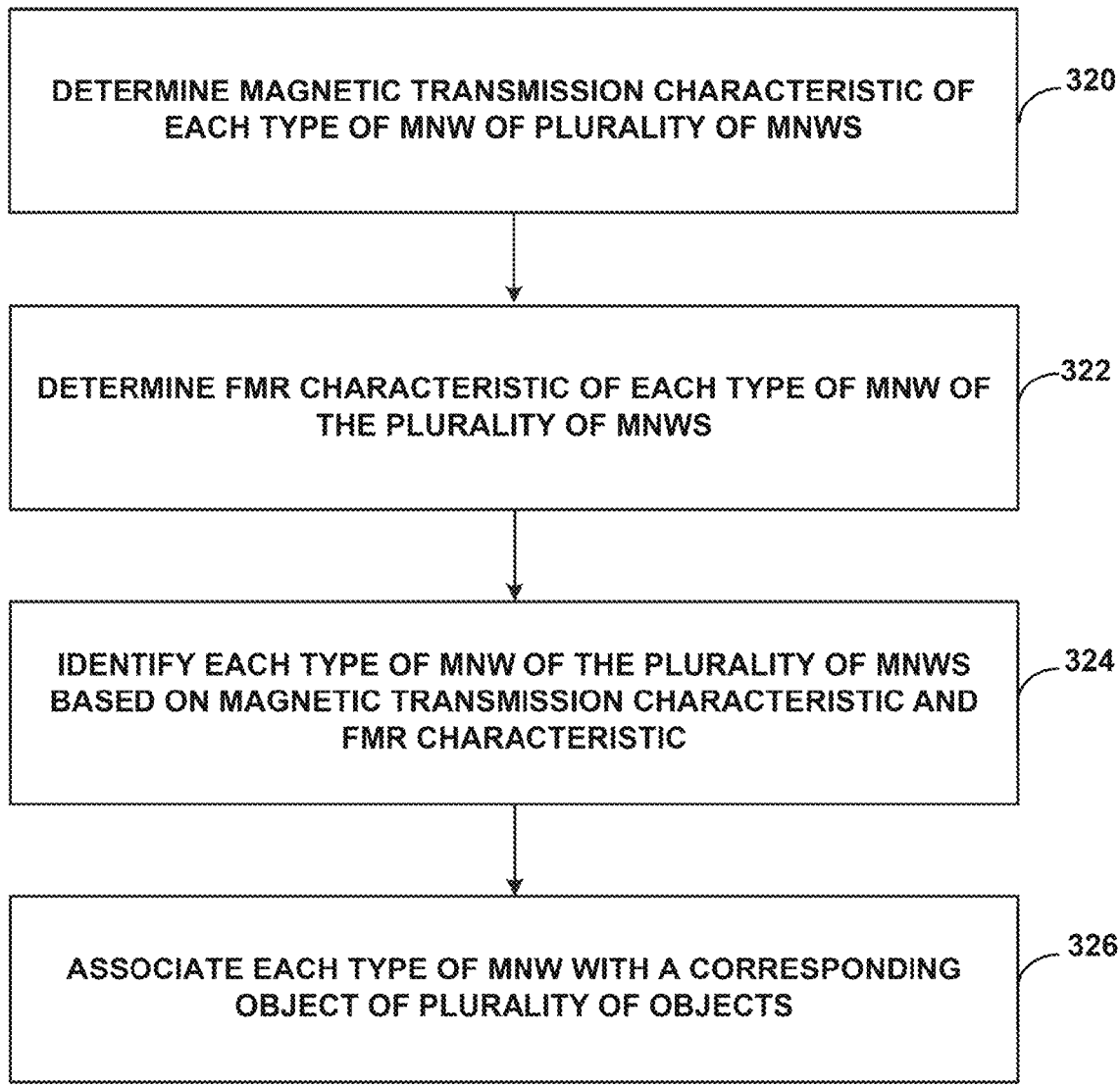
FIG. 20 is a flow diagram illustrating an example technique for characterizing MNWs in accordance with examples of this disclosure.
Figure 21:
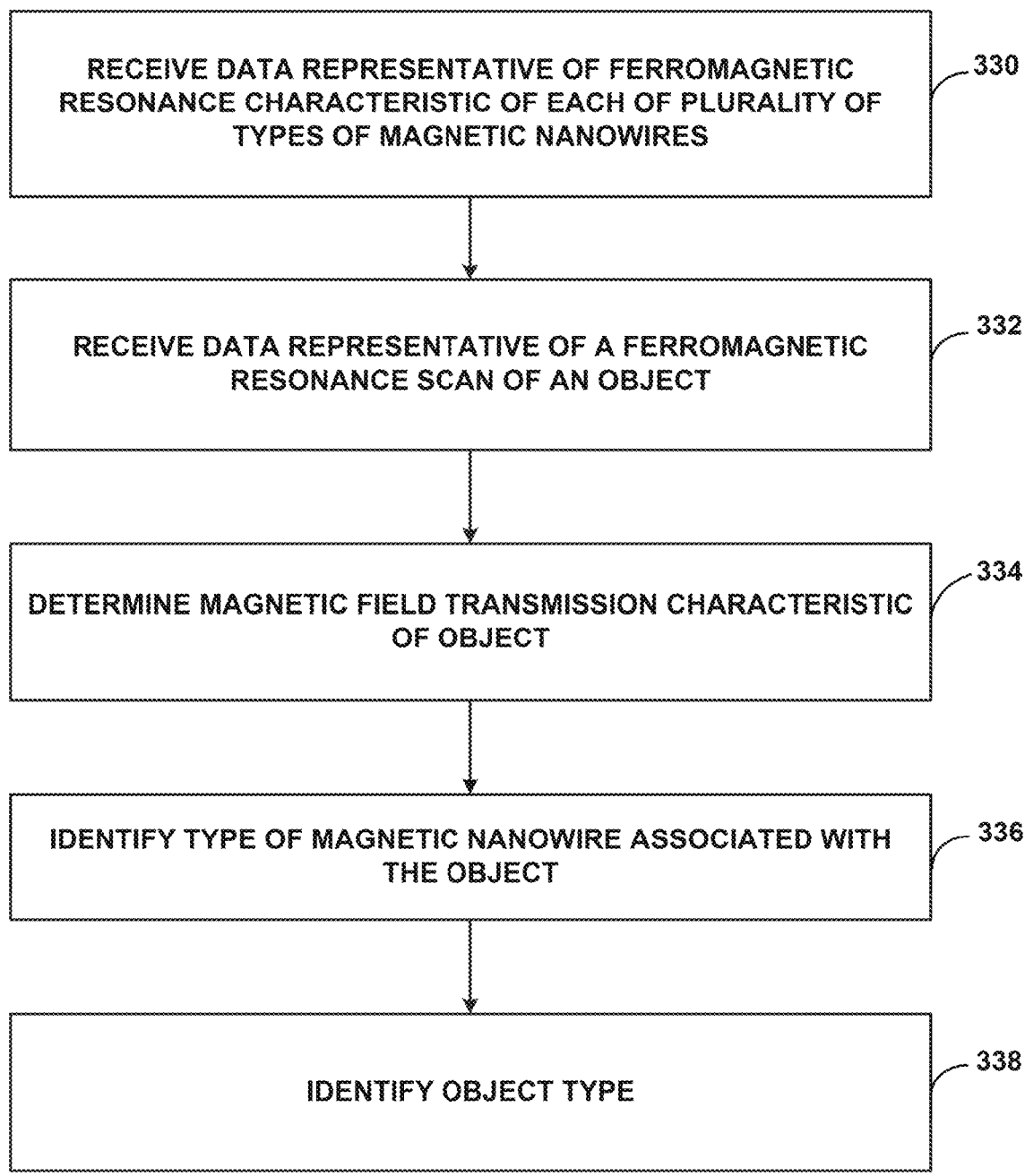
FIG. 21 is a flow diagram illustrating an example technique for identifying an object type based on a type of MNW associated with the object in accordance with this disclosure.
Figure 22:
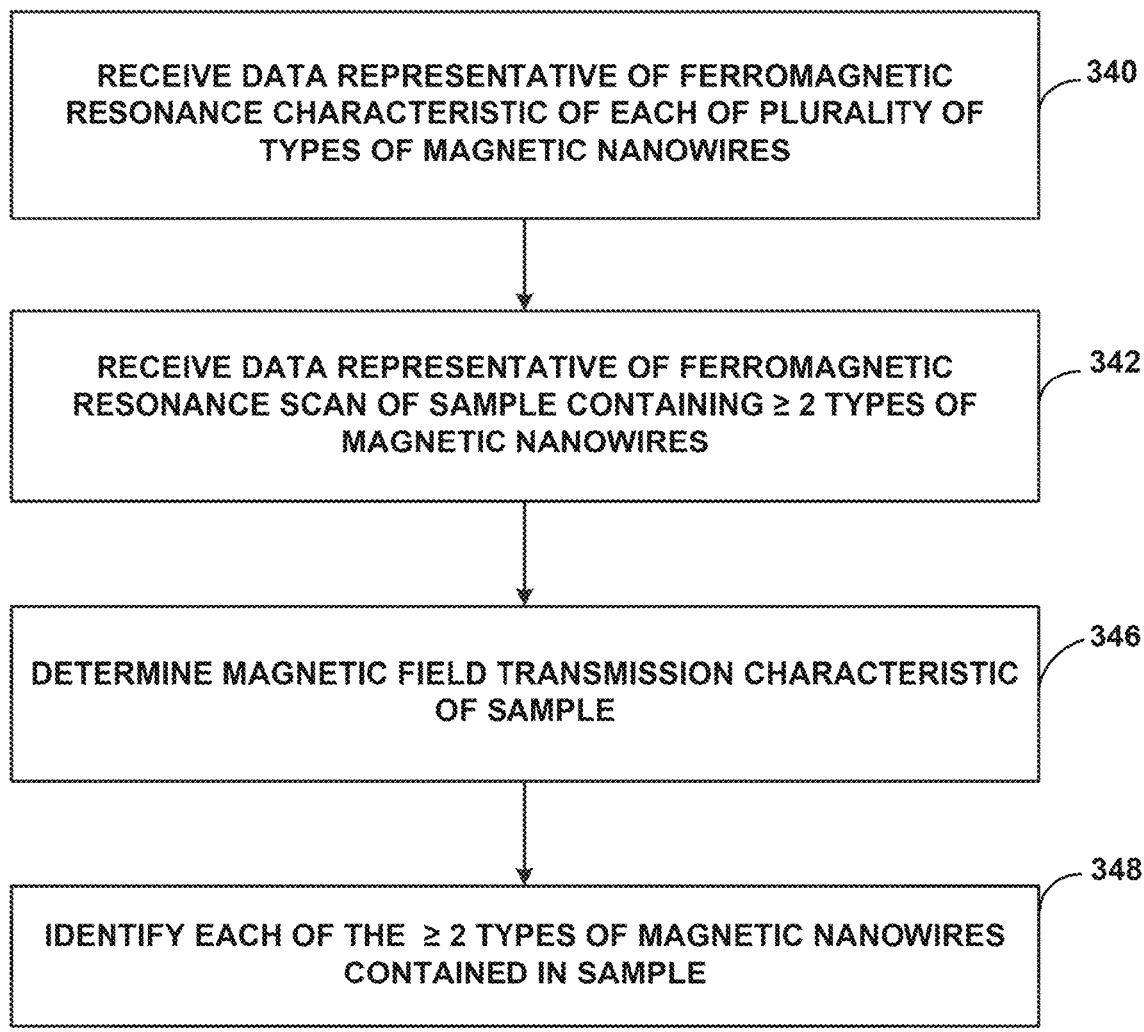
FIG. 22 is a flow diagram illustrating an example technique for identifying a plurality of types of MNWs in a sample containing the plurality of types of MNWs.
Figure 23:
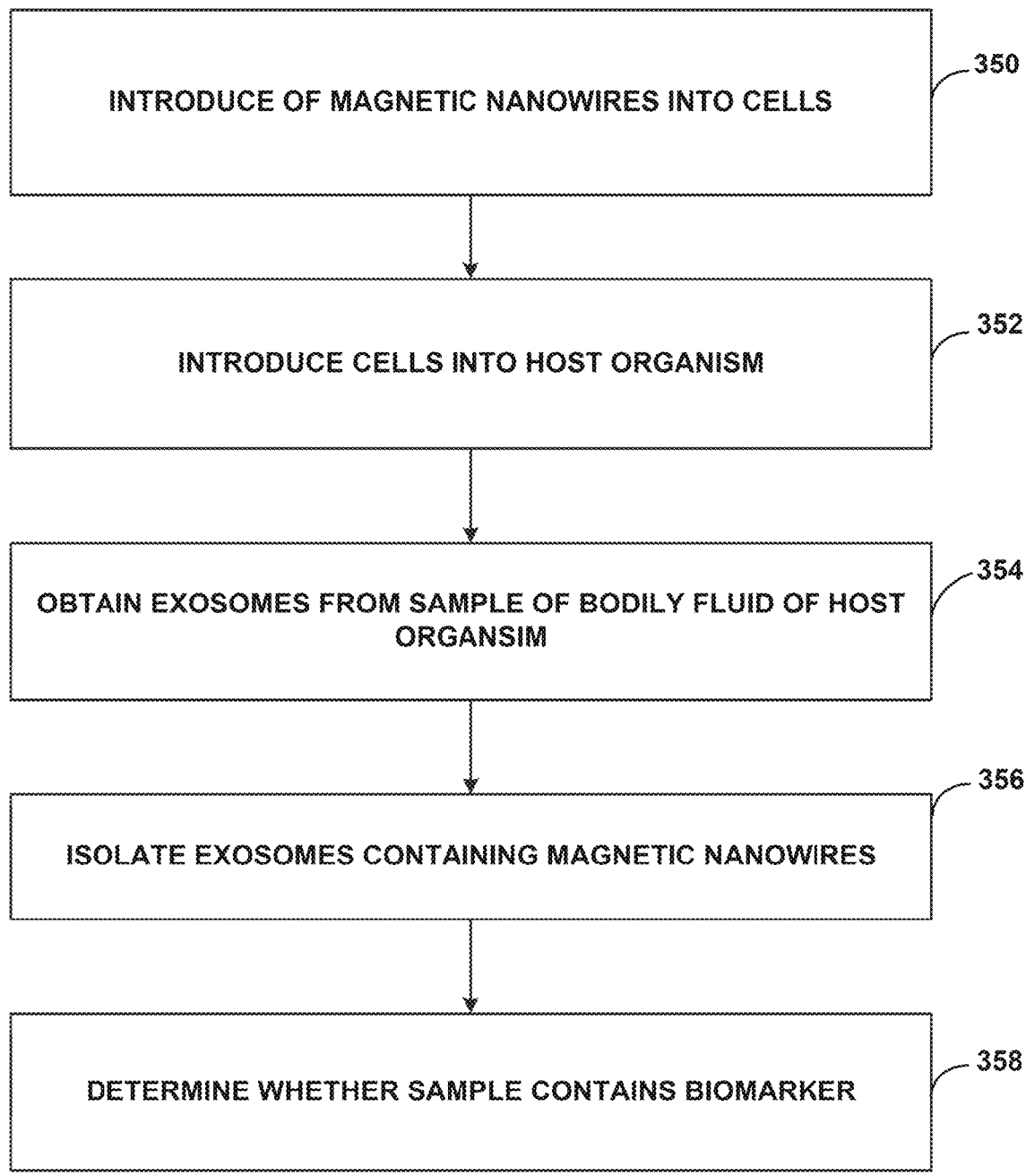
FIG. 23 is a flow diagram illustrating an example technique for determining whether a sample of bodily fluid from an organism contains exosomes containing MNWs associated with a biomarker.
Figure 24:
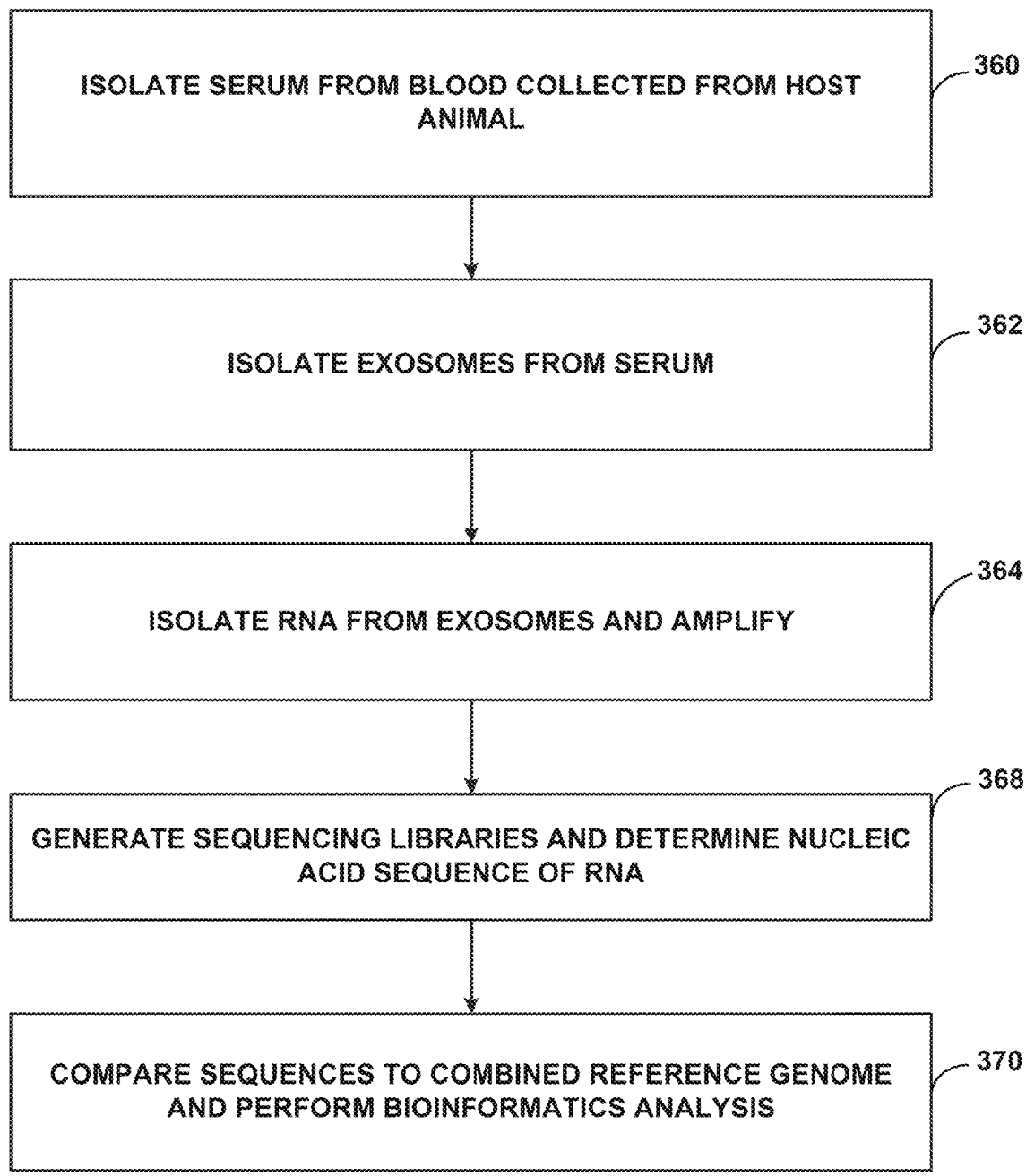
FIG. 24 is a flow diagram illustrating an example technique for identifying exosomes in accordance with examples of this disclosure.
Figure 25:
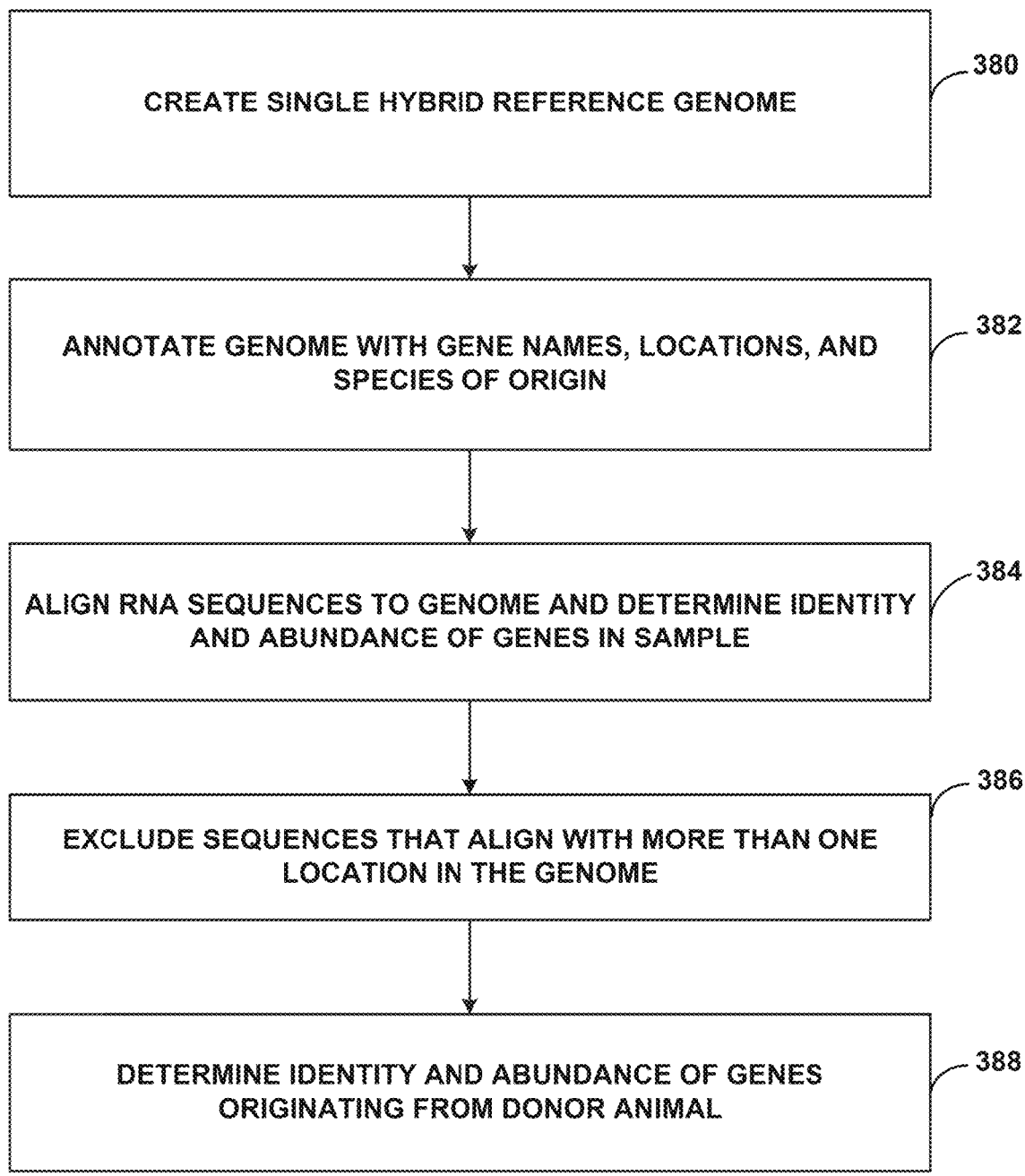
FIG. 25 is a flow diagram illustrating another example technique for identifying exosomes in accordance with examples of this disclosure.

FIGS. 20-25 are flow diagrams illustrating example techniques in accordance with examples of this disclosure. The flow diagrams of FIGS. 20-22 are broadly applicable to any of the example applications of MNWs as labels. The flow diagrams of FIGS. 23-25 are applicable to example biolabeling applications of MNWs. FMR detection system 80 illustrated in FIG. 8 and/or computing device 110 illustrated in FIG. 9 may be described for the example techniques of FIGS. 20-25, although other devices, processing circuitry, or combination thereof may be used to perform the techniques of FIGS. 20-25 and other techniques described herein in other examples.

FIG. 20 is a flow diagram illustrating an example technique for determining characteristics of a plurality of types of MNWs, identifying the types of MNWs, and associating each of the types of MNWs with a corresponding object. According to the example of FIG. 20, processing circuitry 112 of computing device 110 may determine a magnetic field transmission characteristic corresponding to each type of MNW of a plurality of types of MNWs (320). For example, processing circuitry 112 may receive data from computing device of a system configured to measure and/or calculate magnetic parameters of each type of MNW, such as described above with respect to FIGS. 8 and 9.

Processing circuitry 112 then determines an FMR characteristic of each type of MNW of the plurality of types of MNWs, where each type of MNW has an FMR characteristic that differs from an FMR characteristic of each other type of MNW of the plurality of types of MNWs (322). For example, processing circuitry 112 determines the FMR characteristic of the type of MNW as being the at least one of a strength of a magnetic field or a frequency of a first radio frequency signal that corresponds to an FMR of the type of MNW based on data representative thereof, which processing circuitry receives from a computing device such as computing device 82 of FMR detection system 80.

In some such examples, FMR detection system 80 obtains such data by conducting an FMR scan of each type of MNW, which includes, for each type of MNW, applying the magnetic field to the type of MNW, directing the first radio frequency signal to the type of MNW while the type of MNW is subject to the magnetic field, and detecting a second radio frequency signal resulting from the first radio frequency signal passing by the type of MNW, such as by processing circuitry of computing device 82, where a difference between the first radio frequency signal and the second radio frequency signal corresponds to a radio frequency absorption of the type of MNW.

Processing circuitry 112 then identifies each type of MNW of the plurality of types of MNWs based on the corresponding magnetic field transmission characteristic and the corresponding FMR characteristic (324), and associating each type of MNW of the plurality of MNWs with a corresponding object of a plurality of objects, where each object differs from at least one other object of the plurality of objects (326). In this manner, a system of "barcoded" MNWs may be established, each of which having at least one of a composition or a dimension that differs from at least one of a composition or a dimension of each other type of MNW of the plurality of types of MNWs. Although FIG. 20 describes a specific technique for performing each of these steps, the steps may be performed in different orders, by two or more different devices/systems, or even using only a subset of the steps. For example, a system may receive the FMR characteristic that has already been determined by a different device and use that FMR characteristic to associate with various objects.

FIG. 21 is a flow diagram illustrating an example technique for identifying an object type based on a type of MNW associated with the object in accordance with this disclosure. In some examples, processing circuitry 112 receives data representative of an FMR characteristic of each type of MNW of a plurality of types of MNWs, such as from computing device 82 of FMR detection system 80 (330). In such examples, each type of MNW has an FMR characteristic that differs from an FMR characteristic of each other type of MNW of the plurality of types of MNWs, such as one or more of a different S11 or S21 at a given frequency and magnetic field strength, coefficient $c_k$, or other characteristic of interest.

Processing circuitry 112 then receives data representative of an FMR scan of an object, such as from computing device 82, where such an FMR scan includes an application of a magnetic field to the object (332). In some such examples, computing device 82 obtains and conveys the data representative of the FMR scan of the object by directing a first radio frequency signal toward the object while the object is subject to the magnetic field, detecting a second radio frequency signal resulting from the first radio frequency signal passing by the object, generating data representative of the second radio frequency signal, and transmitting, to processing circuitry 112, the data representative of the second radio frequency signal.

Based on the data received from computing device 82, processing circuitry 112 determines a magnetic field transmission characteristic of the object (334) and identify one or more types of MNWs of the plurality of types of MNWs associated with the object based on the magnetic field transmission characteristic of the object (336). Processing circuitry 112 then identifies the object based on the one or more types of MNWs identified based on the magnetic field transmission characteristic of the object (338). In some such examples, processing circuitry 112 identifies the object based on the one or more types of MNW based on the magnetic field transmission characteristic of the object by at least comparing the magnetic field transmission characteristic of the object to respective FMR characteristics of the at least one type of MNW of the plurality of MNWs and identifying the object based on the comparison. In some such examples, computing device 110 stores the FMR characteristics of the at least one type of MNW in memory 114 of computing device 110, which facilitates the identification of MNWs and the objects associated with the types of MNWs. In some examples, processing circuitry 112 causes user interface 120 to display one or more of an identify of one or more types of MNWs that may be associated with an object and/or an identify of the object associated with the one or more types of MNWs. Although FIG. 21 describes a specific technique for performing each of these steps, the steps may be performed in different orders, by two or more different devices/systems, or even using only a subset of the steps. For example, a system may receive the magnetic field transmission characteristic that has already been determined by a different device and use that magnetic transmission characteristic to identify the one or more types of MNWs associated with an object.

FIG. 22 is a flow diagram illustrating an example technique for identifying a plurality of types of MNWs in a sample containing the plurality of types of MNWs. In the example technique of FIG. 22, processing circuitry 112 receives data representative of a FMR characteristic of each type of MNW of a plurality of types of MNW (340). In some such examples, each type of MNW of the plurality of types of MNW has a respective composition different from the compositions of other types of MNWs of the plurality of types of MNWs, and the respective FMR characteristic of each type of MNW of the plurality of types of MNWs differs from FMR characteristics of other types of MNWs of the plurality of types of MNWs.

Processing circuitry 112 further receives data representative of an FMR scan of a sample containing at least two types of MNWs of the plurality of types of MNWs (342) where the FMR scan includes an application of a magnetic field to the sample. For example, the processing circuitry then determines a magnetic field transmission characteristic of the sample based on the data, where the magnetic field transmission characteristic of the sample corresponds to a combination of the respective FMR characteristics of the at least two types of MNWs contained in the sample (346).

In some such examples, FMR detection system 80 conducts the FMR scan of the object by a technique substantially similar to the technique described above with respect to FIG. 21, such as by applying the magnetic field to the object, directing a first radio frequency signal toward the object while the object is subject to the magnetic field, detecting a second radio frequency signal resulting from the first radio frequency signal passing by the object, generating data representative of the second radio frequency signal, and transmitting, to processing circuitry 112, the data representative of the second radio frequency signal.

Processing circuitry 112 is further configured to identify each of the at least two types of MNW of the plurality of types of MNWs contained in the sample (348). For example, processing circuitry 112 uses one or more magnetic field transmission characteristics of the sample and the FMR characteristics corresponding to each type of MNW of the plurality of types of MNWs to fit such data to Equation 4 to determine the contributions of each type of MNW of the plurality of MNWs to the magnetic field transmission characteristic of the sample. Although FIG. 22 describes a specific technique for performing each of these steps, the steps may be performed in different orders, by two or more different devices/systems, or even using only a subset of the steps. For example, a system may receive the magnetic field transmission characteristic that has already been determined by a different device and use that magnetic transmission characteristic to identify each of the plurality of types of MNWs contained within a sample.

FIGS. 23-30 illustrate an example application of the techniques and systems for manufacturing, characterizing, and identifying MNWs described above. As described below with respect to the example of FIGS. 24-30, MNWs may be used to label biological materials containing a biomarker of interest (e.g., RNA expression products of one or more genes of interest), which may be associated with a health condition or other biological state. There is a new drive for personalized health care, especially for cancer treatment and cancer prevention. Medical needs include, e.g., tests to accurately predict cancer risk; robust tests for early cancer detection; biomarkers to provide reliable prognosis of cancer progression and response to therapy; and tests that can be used to tailor personalized therapies (e.g., which drugs to use on which patient). In some examples, the magnetic characteristics of the MNWs may facilitate the later isolation and analysis of the biological materials containing the MNWs and the biomarker of interest.

Personalized health care (e.g., cancer treatment and prevention) may be available by meeting desired features such as: 1) accurate predictors of risk; 2) robust tests for early detection; 3) precise biomarkers to determine progression; and 4) companion diagnostics for individualizing therapy.

These desired features may be met using blood biopsies, which are minimally invasive and safe compared to tissue biopsies. In various organisms, circulating exosomes, which are secreted by cells to communicate with both local and distant environments and seem to be necessary for both tumor survival and preparation of new metastasis sites. As described herein, FMR analysis (as described above) or customized radio frequency identification (cRFID) may be used to detect and then isolate exosomes labeled with MNWs that may enable biomarker discovery. Tumor cells, or other types of cells in other examples, may take up (e.g., internalize) such MNWs, package them into exosomes, and actively release them for a period of time, such as at least 11 days. The identification of biomarkers in exosomes may address the personalized healthcare needs above, and may have broad impact on the medical, magnetic, and high-frequency industries.

The example techniques described herein for isolation of exosomes released by cells (e.g., cells from various types of tissue that may include cancer cells) and identification of presence and/or abundance of biomarkers of interest include identifying MNWs derived from exosomes via FMR analysis or cRFID signals. Such methods may enable early detection and progression assessment of different tumors or other tissue behavior using a simple blood test, through fast and inexpensive magnetic isolation of the MNWs. It should be understood that although the example techniques for using MNWs in exosome isolation and biomarker analysis are described in the context of cancer detection and analysis, such techniques are not limited to this context. For example, such techniques may be used to isolate exosomes, cells, or other biological materials containing MNWs previously delivered to the organism and associated with any biomarker of interest.

Current methods for cancer detection and analysis are mostly based on tissue biopsies, which are expensive and often unreliable in the early stages of cancer. Cancer cells appear to use exosomes to survive and metastasize to other tissues. Because exosomes contain materials that are unique to each cell, they can provide us information about the state of tumor cells. Recently a method was developed to identify tumor and host-derived exosomes using xenografts and a bioinformatic pipeline to map and quantify unique mRNAs based on species of origin. An immune deficient host organism is typically used in this process, and exosomes released by cancer cells are separated from exosomes corresponding to other cells of the host organism.

A solution for more personalized healthcare solutions may involve "blood biopsies." In some practices, material accessed from a sample of peripheral blood is used to obtain or refine a diagnosis or predict the course of a disease. Obtaining blood samples is safe, rapid, and minimally invasive, and blood biopsies are well suited for routine and/or repeated patient monitoring.

Blood biopsies can be used to understand tumor behavior. As tumors evolve and adapt to their environment, they communicate with cells in the near environment as well as with distant tissues. This communication is important for survival of tumor cells, as well as for successful establishment of metastasis. Understanding the interactions of tumors and their local environment can aid in risk assessment (i.e., will a tumor become established), early detection, and the probability of disease progression.

An important mode of communication used by tumors is secretion of small, membrane bound vesicles called exosomes. Exosomes are synthesized in the endosomal pathways. Extracellular molecules are "ingested" into membrane bound vesicles, and cells then actively package materials into these vesicles. This means that exosomes contain materials that are unique to each tumor. However, among tumors, exosomes may share molecules that are reflective of specific biological processes. Therefore, the material in secreted exosomes can specifically inform the state of tumor cells whether they are present or absent, whether they are actively growing, and whether they are preparing distant sites for metastasis. For example, while much of a cell's nucleic acids are located within the cell, some nucleic acids, such as RNA, can be transported out of the cell inside exosomes. In particular, cell-free RNA may be found in the bloodstream of animals inside exosomes. These cell-free nucleic acids can then be used as biomarkers to determine the presence of disease, its biological behavior, its rate of progression, and its potential to respond to unique therapies.

Exosomes can be isolated from blood samples (serum or plasma). The isolation methods are well established, but they are laborious. Furthermore, exosomes derived from tumor cells represent the proverbial "needle in a haystack," because they co-exist with quadrillions of exosomes in blood that are secreted by every other cell in the body. The tumor can represent $10^9$ cells; the body represents $>10^{13}$ cells. Even if a tumor cell secretes 10× as many exosomes as a normal cell, there is still only 1 exosome from tumor cells for every 1,000 exosomes from normal cells. Techniques for using MNWs to identify tumor-derived exosomes with high efficiency in animal models, as described below, advantageously may help enable the isolation of such tumor-derived exosomes.

In some examples, techniques for using MNWs to identify tumor-derived exosomes may, include establishing the presence and composition of nucleic acids in the blood of mice harboring a disease of humans or companion animals. For example, such techniques may include using orthotopic xenografts of canine osteosarcoma in nude mice. In this case, potential biomarkers for disease include nucleic acids (genes) indicative of osteosarcoma (canine origin), nucleic acids indicative of biological behavior and/or progression for specific osteosarcomas (canine origin), and nucleic acids indicative of host response to bone invasion, host response to osteosarcoma in general, and response to distinct osteosarcomas with different biological behavior in particular (all of mice origin).

In some such other examples, cells used for xenografts are called OS-1 (OSCA-32) and OS-2 (OSCA-40). Such cells may be derived from canine tumors with distinct biological behavior and recapitulate this behavior in xenografts. In this example, the cross-species hybrid genome approach may be used to identify separate canine and mouse sequences from tumor xenografts that inform the progression of disease (in the mouse). Thus, it is possible to use tumor samples grown in mice to determine the contribution of dog sequences (derived from the implanted, growing tumor cells) and mouse sequences (derived from infiltrating stroma) to define features of progression for tumors arising from implantation of the different cell lines.

FIGS. 23-25 are flow diagrams illustrating example techniques for using MNWs as biolabels that enable a determination of whether a sample contains a biomarker of interest. It should be understood that although the example techniques of FIGS. 23-25 are described with respect to a specific application of the techniques, such example techniques may instead be carried out using different types of donor and/or host animals, investigating one or more different biomarkers, or using other suitable laboratory techniques to carry out the steps of FIGS. 23-25.

FIG. 23 is a flow diagram illustrating an example technique for determining whether a sample of bodily fluid from an organism contains exosomes containing MNWs associated with a biomarker, such as in the example of a mouse host organism that contains a canine tumor xenograft as described above. In some examples, the technique of FIG. 23 may include introducing a plurality of MNWs into one or more cells (350), which may be done either within or outside of a host organism. The cells may be introduced into one or more cells into a body of a host organism (352), such as a body of a mouse or other suitable host organism. A plurality of exosomes from a sample of bodily fluid from the host organism may be obtained from the plurality of exosomes (354), one or more of which each may contain one or more MNWs of the plurality of MNWs. In some examples, the technique of FIG. 23 may further include determining that the sample of bodily fluid contains a biomarker indicative of a biological status based on the presence of the one or more exosomes isolated from the plurality of exosomes that each contain the one or more MNWs of the plurality of MNWs (356).

FIG. 24 is a flow diagram illustrating an example technique for identifying exosomes in accordance with examples of this disclosure. Serum is isolated from blood collected from mice at a "time 0," i.e., prior to any manipulation (360). In some such examples, experimental groups may include: mice injected intratibially with PBS (phosphate-buffered saline), with no cells, i.e., control for host response to intratibial injection and possible consequent inflammation; mice injected intratibially with OS-1 cells; and mice injected intratibially with OS-2 cells. In this example, serum is isolated from blood collected from mice in each group every two weeks up to 8 weeks. For each group, there are two cages of 4 mice each. Each cage is an experimental replicate (blood pooled from all the mice in the cage to isolate sufficient serum for exosomes; furthermore, blood may be pooled for analysis from weeks 2, 4, 6, and 8 for each cage, although aliquots may be preserved from the pool for each week for validation by qRT-PCR).

Exosomes then are isolated from the serum (362). In some examples, this is accomplished by using ExoQuick kits from System Biosciences, Inc. (SBI), although other suitable techniques may be used. Next, total RNA is isolated from the exosomes (364) and amplified. For example, this may be accomplished by using the Complete SeraMir Exosome RNA Amplification kit from SBI and precipitated with the Dr. GenTLE (Gene Trapping by Liquid Extraction) System from SBI, although other suitable techniques may be used.

Sequencing libraries then may be generated from the RNA isolated from the exosomes, such as by using Nextera XT DNA Library Preparation Kit (Clontech) at the University of Minnesota Genomics Center (UMGC) (368), although other suitable techniques and facilities may be used. In some examples, sequencing is done at UMGC on a 50 base-pair paired-end (PE) run on a HiSeq 2500 nucleic acid sequencing instrument using Rapid chemistry. In some examples, the technique uses 8 samples per lane and generate >120 M reads, which may be fairly well balanced across different applications. Preferably, average quality scores are above Q30 for all PE reads.

Comparison of the sequences obtained at (368) to a cross-species hybrid genome is then performed (370), followed by bioinformatic analyses (370). A summary of example bioinformatics methods for creation and mapping to cross-species hybrid genome and the workflow of data analysis steps with illustrations is described in further detail below.

FIG. 25 is a flow diagram illustrating an example bioinformatics method related to the example method of identifying exosomes described with respect to FIG. 24. A single hybrid reference genome for two species is created by combining the reference sequences of all chromosomes of each species into one file, with chromosome names modified to indicate the species of origin (380). Next, a single hybrid genome annotation file describing the locations of genes in the genome is created by combining the annotation of each species into one file, with chromosome and gene names modified to indicate the species of origin (382). A sequence alignment program, such as HISAT2, then is used to align RNA-Seq sequence reads to the hybrid genome (384). Most reads will map uniquely to a chromosome of one of the species. Some parts of the genomes will be identical in both species resulting in a small number of multi-mapped reads mapping to two chromosomes, one from each species, although longer sequence reads reduce the number of multi-mapped reads. The presence and abundance levels of genes may be determined by comparing the genomic location of each uniquely aligned read with the genomic locations of genes in the hybrid annotation file and summing the number of reads aligning to each gene.

Multi-mapped genes then are excluded from the analysis (386). Excluding multi-mapped reads from the abundance estimation step may be useful to avoid incorrectly identifying the presence of graft-derived nucleic acids. Aligning RNA-Seq reads only to the reference genome of the graft species may result in the spurious identification of graft-derived genes in cases where the genes have identical sequences in both species. It may be desirable to compare gene expressions levels from a xenograft sample with a negative control sample way provide further power to reduce false-positives. Next, the identity and abundance of genes originating from the donor animal, which in this example may be a dog, is determined (388). As described in further detail below, the determined identity and abundance of genes originating from the donor animal may be used to determine the presence of disease and disease progression, and may inform treatment decisions.

In the examples described above and illustrated in FIGS. 24 and 25, tumor-derived exosomes may be identified with high efficiency in laboratory animal models. The method of such examples is graphically illustrated in FIG. 26. The rationalization is that if the 0.1% of exosomes that come from a tumor could be reliably identified, the unique biomarkers that are present in these exosomes could be subsequently identified to address the desired features for a solution as described above. Not only that, by also excluding the tumor exosomes, potential differences could be discovered for how normal cells in the host animal (the surrogate "patient") respond to distinct tumors by altering the profile of molecules in their exosomes (the other 99.9%). These and other examples are described in additional detail in U.S. Provisional Patent Application Ser. No. 62/407,987, entitled "IDENTIFYING PRESENCE AND COMPOSITION OF CELL-FREE NUCLEIC ACIDS" and filed on Oct. 13, 2016, the entire content of which is incorporated herein by reference.

Figure 26:
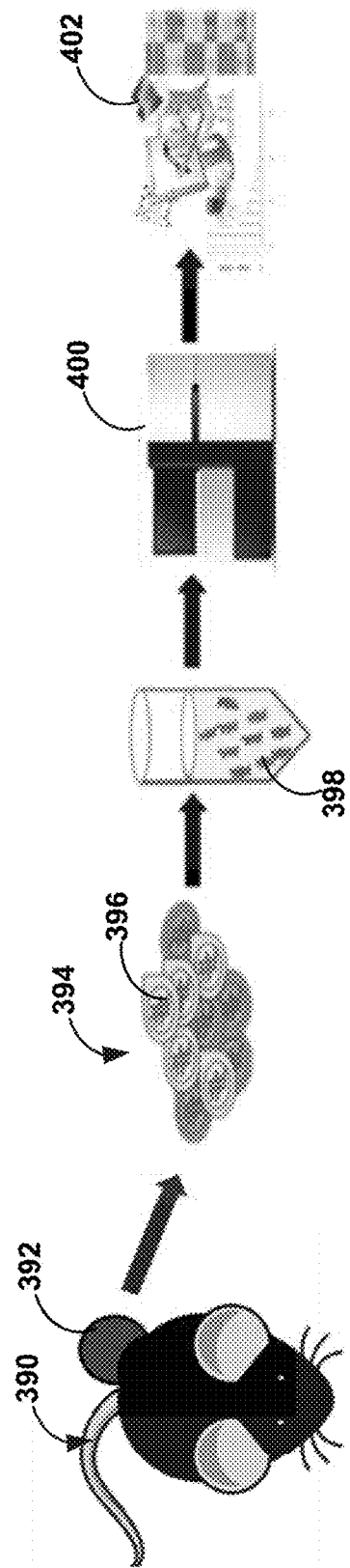
FIG. 26 is a graphical representation of portions of the example techniques illustrated in FIGS. 24 and 25.

FIG. 26 is a graphical representation of portions of the example techniques illustrated in FIGS. 24 and 25. In the example of FIG. 26, cells of a patient tumor are injected into a mouse host 390. The "patient" can be a human, a dog, or any animal that is not a mouse. The tumor 392, called a xenograft (xeno=foreign, graft=tissue transplant), grows in mouse 390 and secretes some of exosomes 394 into the blood of mouse 390. Tumor-cell exosomes are mixed with the mouse exosomes (made by normal mouse cells as part of the normal background, but also, potentially, in response to tumor 392) in total exosomes 394. Blood samples are obtained from mouse 390 and total exosomes 394, which includes exosomes that do not contain MNWs as well as exosomes 396, which do contain MNWs, are isolated from the samples. NNW-containing exosomes 396 may be isolated from total exosomes 394, such as by using magnetic isolation as described below with respect to FIGS. 28A-28C.

RNA 398 then may be extracted from isolated exosomes 396. Using genomic tools (e.g., any suitable sequencing apparatus), all of the messenger RNA (mRNA) in exosomes 396 may be sequenced. The mRNA sequences that belong to mouse 390 are then separated from the ones that belong to the patient (donor) via bioinformatics analysis 402. This technique has confirmed the feasibility and robustness of the experiments using dog bone tumors transplanted into the bone of mouse hosts.

However, in order to grow tumor xenografts in mice (e.g., mouse 390), the mice must have deficiencies in their immune system. If mice have normal immune systems, they reject the tumors. This creates a "hole" in the exosome data, including both exosomes that would be secreted from the tumor cells if they interact with immune cells (normally present in patients) and exosomes secreted by the immune cells in response to the tumor. Such exosomes may be important in the present environment where immunotherapy is becoming a major modality for cancer treatment.

Therefore, a complementary method to separate exosomes in animals that have intact immune systems may be desirable. Mice with complete immune systems can serve as hosts for tumors if the tumors originate from animals with identical genetic backgrounds (called "syngeneic"). In these cases, tumors grow because they are invisible to the immune system. Even though not all tumors are able to evade the immune system, and the transplantation models still have some differences from tumors that arise spontaneously, these models have been highly informative to understand tumor growth, tumor-immune and tumor-environment interactions, and to develop therapies.

Several methods may be used to separate exosomes derived from tumor cells and exosomes derived from normal cells in "syngeneic" systems. As described above, processes have been developed to make MNWs that are taken up by tumors, such as by applying coatings on MNWs that reduce surface oxidation and/or by biofunctionalization of the MNWs by applying ligands that target a cell type of interest (e.g., the tumor cells). The MNWs are then packaged in exosomes and secreted by the cells continuously, at least over the course of 11 days. Because the MNWs are magnetic, the tumor-derived exosomes can be isolated from the rest of the mouse exosomes using a magnet. Tumor exosomes containing MNWs may maintain the same physical properties as the tumor exosomes derived from the same cells without MNWs.

Some example methods described herein may enable determination of whether MNWs alter packaging of RNA molecules into exosomes. There may not be significant differences in exosomes that contain MNWs compared to exosomes that do not, in which case magnetic separation of "natural" exosomes may be a significant advance the field of biomarkers by allowing fast, inexpensive magnetic isolation from syngeneic ("immunologically replete") animal models. However, even in the case that there are some differences in exosome RNA, once the differences are known they can be accounted for in final analysis. Also, recall that current identification of tumor RNA involves xenografts (tumors implanted from different a species) which cannot be used in hosts with immune systems. Combining the example methods described herein with other example methods (e.g., the methods illustrated in FIGS. 1 and 2) may enhance biomarker knowledge as they are orthogonal techniques: one with xenograft RNA but no immune cells, and the other with both magnetic separation and immune cells.

The example methods described herein may enable determination of variation in amounts of MNWs (e.g., MNWs 418) taken up by various types of cells. If more aggressive cancer cells take up more MNWs, then they may be easier to detect and then to use for biomarker identification. The results of such methods may not necessarily depend on the cRFID signature of the MNWs. The example methods described herein also may enable determination of whether a direct relationship exists between the magnitude of the detected signature and the number of cells and/or the number of MNWs loaded into the cells, and may enable determination of whether immune cells (white blood cells) may be loaded with MNWs.

Figure 27:
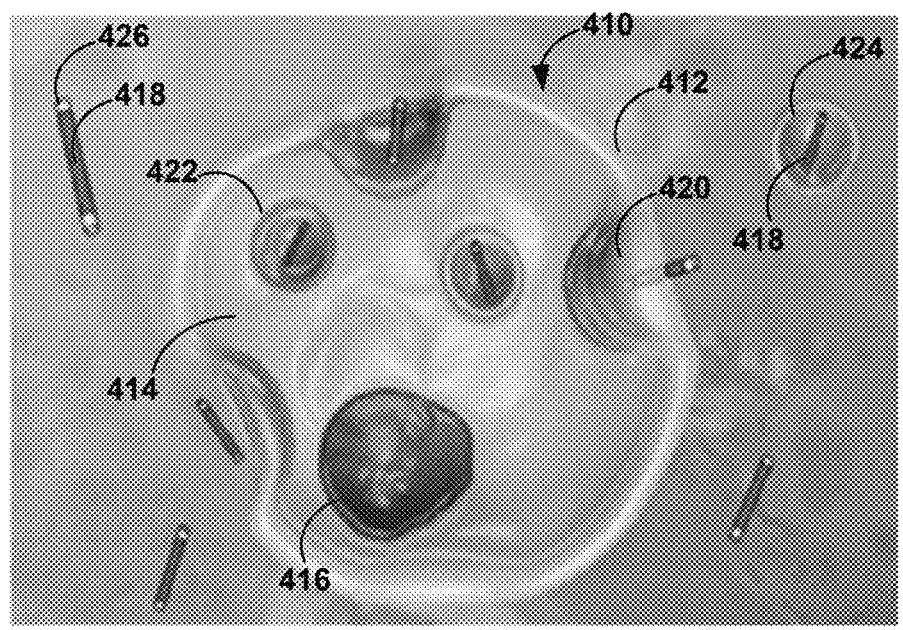
FIG. 27 is a graphical representation of example customized MNWs (diameters 10-100 nm, lengths 100-1000 nm) being taken up by a cancer cell and then released inside an exosome (on right).

FIG. 27 is a graphical representation of a cancer cell 410 having a cell membrane 412, cytoplasm 414, and a nucleus 416. As shown in FIG. 27, MNWs 418 (e.g., diameters 10-100 nm, lengths 100-1000 nm) may be being taken up by a cancer cell 410. For example, cancer cell 410 may take up MNWs 418 by forming a transport vesicle 420 containing one or more of MNWs 418 in cell membrane 412. Later, cell 410 may form exosomes, such as exosome 422, containing one or more of MNWs 418 within cytoplasm 414. Such exosomes then may be released by cell 410 via cell membrane 412, as depicted by exosome 424 that has been released by cell 410.

In some examples, MNWs 418 may be composed of iron with gold tips 426, although any suitable single-material MNWs (e.g., Co, Ni, or Fe) or segmented MNWs containing one or more such materials and a non-magnetic material in any suitable configuration may be used, such as any materials or configurations of MNWs described herein. Studies indicate that exosomes can be enriched from cell supernatants using MNWs after extended time in culture (up to 11 days). Thus, exosomes derived from different cell types can be distinguished from one another and enriched using MNWs 418 as identifying labels. This may enable discovery of biomarkers associated with the presence of tumors, their biological behavior, and the host response.

In one example application of MNWs 418, the contents of MNW 418-containing exosomes 424 are comparable, aside from the presence of MNWs 418, to exosomes that do not contain MNWs 418. For example, mouse LL3 Lewis lung carcinoma (lung cancer) and B16 melanoma tumor cell lines may be cultured with and without MNWs 418. Each of these cell lines reliably forms tumors in normal mice. Exosomes may be isolated from culture supernatants (to collect only secreted exosomes) before loading with MNWs 418 (time 0), 1-day after loading, 4-days after loading, and 10-days after loading. MNW 418-containing exosomes may be isolated by magnetic separation, and also by nonmagnetic methods, using exosome-free reagents and a modification of Exoquick-TC from Systems Biosciences Inc. The physical properties of exosomes from both preparations may be characterized by electron microscopy and by optical scattering tools (e.g., dynamic light scattering and NanoSight) available in the Minnesota Nanotechnology Center (MNC). In some of the example methods described herein, the exosomes' biochemical properties may also be studied, such as expression of specific tetraspanins proteins. In addition, in such example methods, RNA may be isolated from exosomes, libraries may be made using a validated low input synthesis method (Clontech), and next generation sequencing may be done, such as to a depth of 10 million paired end reads (sufficient for the low-level input). In some examples, MNWs 418 may not alter packaging of RNA molecules into exosomes, and MNWs 418 may allow for efficient isolation of exosomes from cell culture.

In some examples, tumors may take up MNWs 418 more avidly than normal cells. Based on previous studies of tumor cell behavior, tumor cells may preferentially ingest MNWs 418 with high avidity compared to normal and non-tumor cells, and that MNWs 418 can be detected in tumors in a matrix that resembles human skin and organs. In one application of this example, the loading of MNWs 418 into various cell types from three species (humans, dogs, and mice) may be examined, including at least three tumor cell lines from each species, non-malignant fibroblasts, non-malignant endothelial cells, and normal white blood cells. The MNWs 418 ingested by the cells may be quantified based on their magnetic properties (saturation magnetization, coercivity, and FMR). The cells may be cultured as described above, exosomes may be isolated from supernatants using magnetic separation, and characterized by their physical and biochemical properties.

In some examples, MNWs may be taken up in amounts that vary with the type of cell. For example, more aggressive cancer cells (i.e., ones from fast growing and metastasizing tumors from mice, or from canine and human patients) may take up more MNWs than less aggressive cells. These results may not necessarily depend on the MNW type.

Figures 28A, 28B, 28C:
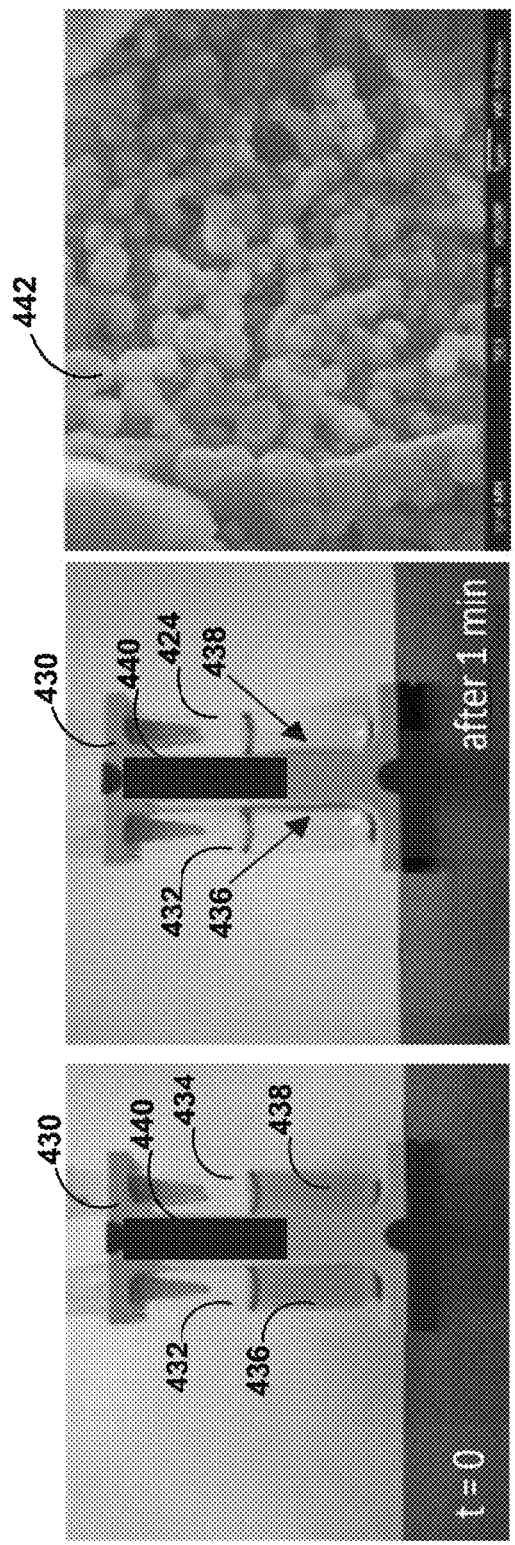
FIG. 28A is a digital image of example MNWs dispersed in solution before magnetic isolation.
FIG. 28B is a digital image of example MNWs aggregated in solution after magnetic isolation.
FIG. 28C is a digital image of example exosomes separated from the solution of FIG. 28B.

FIGS. 28A-28C illustrate an example technique for isolating exosomes that contain MNWs from a sample of bodily fluid from an organism. FIG. 28A is a digital image of MNWs dispersed in solution before magnetic isolation. FIG. 28B is a digital image of MNWs aggregated in solution during magnetic isolation. FIG. 28C is a digital image of exosomes separated from cancer cell assays. In the example of FIG. 28C, the exosomes were separated from osteosarcoma (bone cancer) cell assays. As illustrated by FIGS. 28A-28C, the magnetic characteristics of the MNWs described herein provide multiple functions by enabling magnetic separation of exosomes in addition to enabling identification of objects.

In FIG. 28A, an assay apparatus 430 holds vials 432 and 434 respectively containing fluid samples 436, 438 at t=0. Fluid samples 436, 438 contain exosomes containing MNWs. Fluid samples 436, 438 appear gray because the MNWs are suspended throughout samples 436, 438. Assay apparatus 430 further includes magnet 440, which is illustrated in FIGS. 28A and 28B as a black bar. Approximately one minute after vials 432 and 434 are placed in apparatus 430, the MNWs contained in samples 436, 438 are drawn to magnet 440, resulting in the MNWs being aggregated toward the sides of vials 432, 434 closest to magnet 440, as shown by the arrows at the center of FIG. 28B. With the MNWs thus aggregated, supernatant of samples 436, 438, which contains non-MNW containing exosomes and other components of the bodily fluid sample, may be drawn off, leaving behind exosomes that contain MNWs. Exosomes 442, which were separated from osteosarcoma (bone cancer) cell assays according to the technique described with respect to FIGS. 28A and 28B, are illustrated in FIG. 28C.

Figures 29A, 29B:
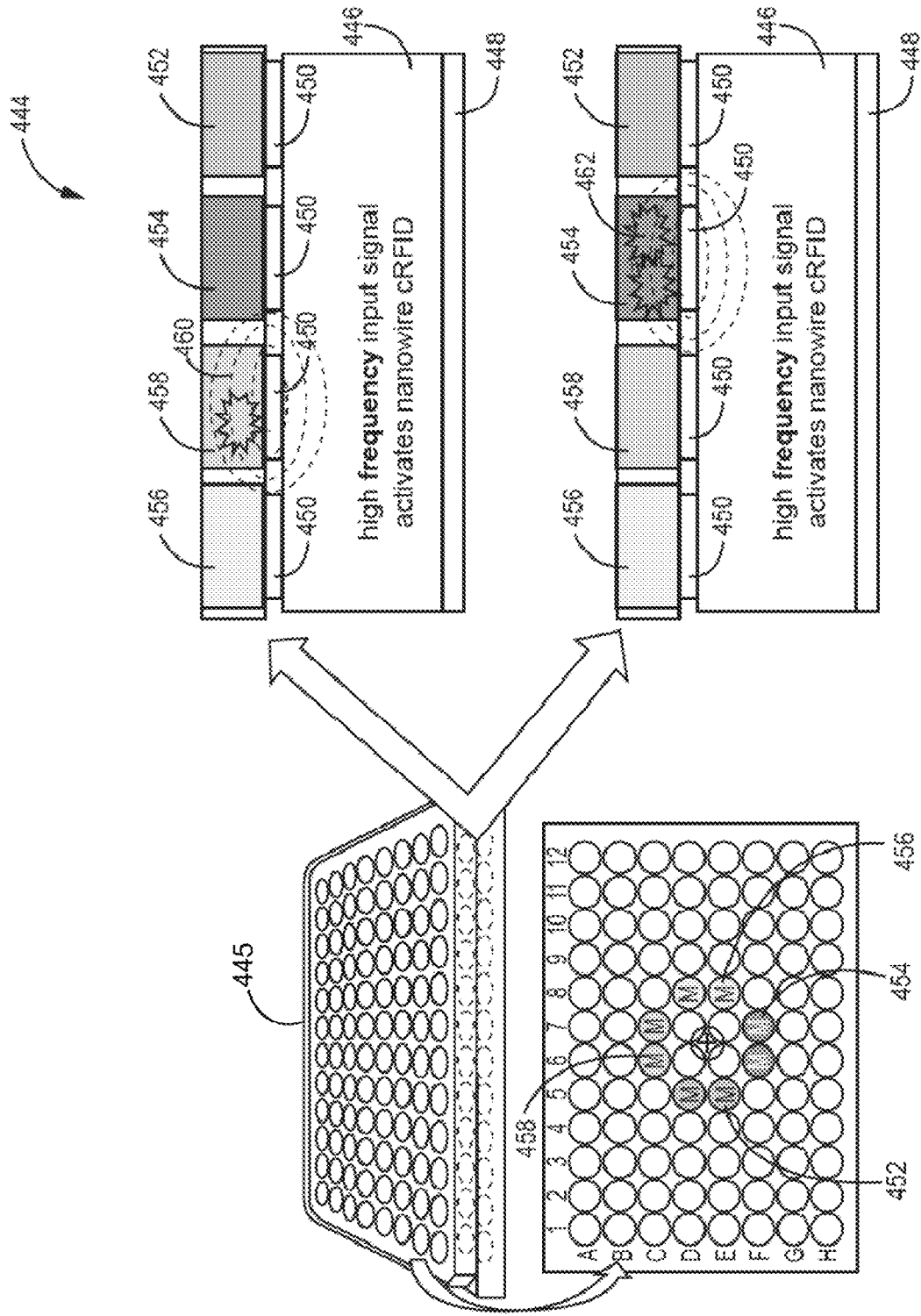
FIG. 29A is a graphical representation of an example 96-well plate that may be used in an alternative MNW analysis technique in accordance with the examples of this disclosure.
FIG. 29B is a graphical representation of an example cut-away of a detection system of the 96-well plate of FIG. 29A for use in MNW analysis technique of FIG. 29A.

FIG. 29A is a graphical representation of a 96 well plate 445, which may be used in an alternative MNW analysis technique with a microwell-integrated cRFID detection system in accordance with the examples of this disclosure. Instead of using FMR analysis of MNWs to identify MNWs associated with a sample or object, as described above, the technique of FIG. 29A using an RF model to predict the cRFID signatures of the MNWs described herein based on wire density, orientation, and quantity. Magnetic simulation software Object Oriented MicroMagnetic Framework (OOMMF) for carrying out this technique may be run at a supercomputer institute, e.g., at Minnesota Supercomputer Institute (MSI), where designs of the example MNWs and example MNW arrays described herein may be simulated and combined with high frequency simulations.

In some examples, high frequency properties of cell cultures, gels and cells may be analyzed with and without MNWs. Such analysis may provide an accurate understanding of the magnetic interactions of MNWs and of the interactions of the liquid and artificial tissue matrices with the test circuits. The measurements may be compared to simulations, and an iterative process may determine the realistic properties and predictions of designs for both the MNWs in a sample and the cRFID measurement system.

A cRFID microwave circuit may be integrated with standard biology analysis trays such as 96-well plate 445. As shown in FIG. 29B, 96-well plate 445 may include microwell-integrated cRFID detection system 444. In some examples, detection system 444 of 96-well plate 445 may include a dielectric substrate 446 that includes a gold ground plane 448 on one side, and microstrip lines 450 on the other. Microstrip line side 450 may be attached to 96-well plate 445 such that AC magnetic fields may be applied to the cell/MNW assays in well pairs 452, 454, 456, and 458, which respectively include wells D5, E5, wells F6, F7, wells D8, E8, and wells C6, C7. Microstrip lines 450 may have a mesh geometry so that individual wells (e.g., C4) can be addressed using crossing lines sequentially (e.g., the C line and then the 4 line).

FIG. 29B is a graphical representation of a cut-away of detection system 444 of 96-well plate 445 for use in MNW analysis technique of FIG. 29A. As the frequency is varied (called frequency sweeping), there may be a cRFID signal created by absorption at a specific frequency if one of the wells contain MNWs with their FMR resonance at that frequency (e.g., wells C6 and C7 of well pair 258). Wells containing other MNWs will create cRFID signals at other frequencies, or cRFID "colors." Activation events 460 and 462 are shown occurring at wells of well pairs 458 and 454 in FIG. 29A. The AC field around each line 450 is shown as dashed lines. The frequency (similar to "color" at optical frequencies) will be varied to provide a "rainbow" of RF color to the wells above microstrip line 450. When the resonance of MNWs in the well is matched by the AC field "color," the transmission may be reduced, and this can be measured so that that "color" has been "read-out." Next, a variety of MNW configurations may be measured to determine their FMR response. This technique thus demonstrates an integrated measurement platform based on known MNW signatures.

Figure 30:
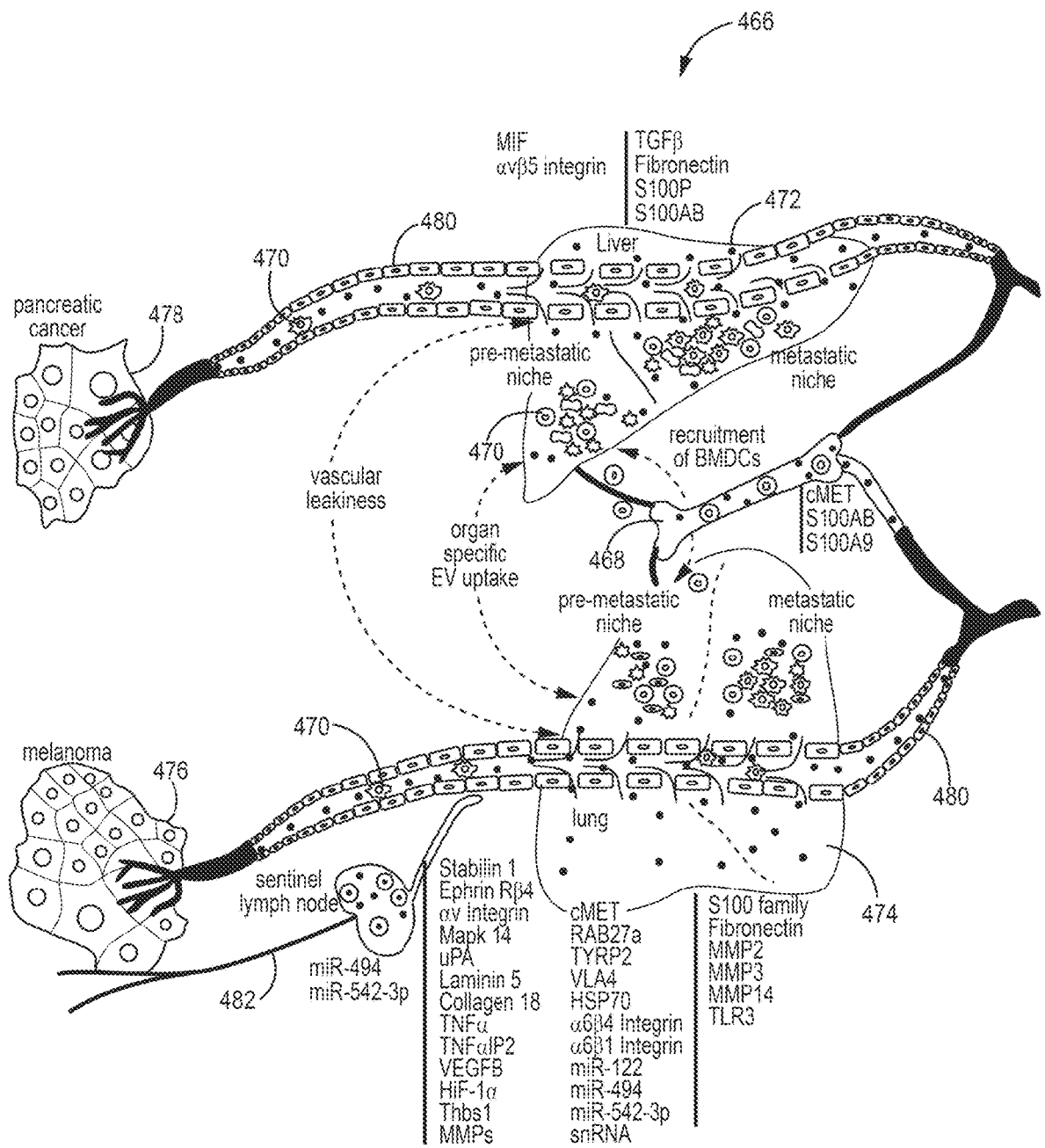
FIG. 30 is a graphical representation illustrating the process in which tumor-derived exosomes can promote pre-metastatic niche formation and metastasis.

FIG. 30 is a graphical representation illustrating how tumor-derived exosomes may promote pre-metastatic niche formation and metastasis in the context of example organ system 466, which in turn illustrates the potential advantages of exosome labeling and isolation using MNWs as described herein. Example organ system includes various organs, tissue types, and cell types as discussed below and may correspond to any animal having one or more such organs, tissue types, or cell types, such as a human, canine, feline, bovine, ovine, rodent, pig, or any other such organism. In the example of organ system 466, bone 468 may be a site of a primary tumor. Tumor cells 470 from bone 468 may migrate from bone 468 to other areas in organ system 466 due to one or more factors illustrated in organ system 466, such as recruitment of bone marrow dendritic cells (BMDCs), organ specific uptake of extracellular vesicles (EVs) such as exosomes, vascular leakiness, or other factors. For example, tumor cells 470 may migrate to liver 272, lung 474, skin 476, pancreas 478, or other organs or tissues via vasculature 480 and establish pre-metastatic or metastatic niches in the organ or tissue. In some examples, tumor cells 470 may additionally, or alternatively, migrate to a sentinel lymph node 482, such as in preparation for further metastasis. In any such examples, up-regulation or down-regulation of expression of one or more genes may contribute to metastatic behavior of a tumor in bone 468. The identification of such genes and quantification of their expression via exosome labeling and isolation techniques using MNWs, as described herein, thus may help enable early diagnosis, accurate prognosis, and/or drug response predictions for a patient having an organ system such as organ system 466.

FIG. 30 thus illustrates that tumor-derived exosomes may be active at multiple points in an organ system in the preparation of distant sites for future metastasis. First, various exosomes can circulate through both blood and/or lymph nodes after they are secreted from the tumor cells. Second, tumor-derived exosomes seem to induce leaks in blood vessels from target particular cells. Different RNAs or proteins are loaded into exosomes form specific cancer types and at different times in the progression of disease. Therefore, these molecules can be used to detect tumors, distinguish their origin, and infer the stage of disease. In order to fulfill an important role as biomarkers, the molecules in exosomes do not need to be associated with the biology of the tumor per se as long as they are invariably present (or absent) in correlation with the disease.

Thus, in some examples, it may be useful to determine the origin of exosomes found in blood biopsies. If tumor-derived, the exosomes could provide novel biomarkers to provide early detection of metastasis and also provide information on the efficacy of cancer therapies. For exosomes not originating from tumor cells, information can be gleaned about the response of the patient to the presence of tumors and/or therapy. Ultimately, the use of MNWs for biolabeling of exosomes or other biological materials having a biomarker of interest in the techniques described herein may enable the following: 1—accurate predictors of risk, 2—robust tests for early detection, 3—enhanced biomarkers to determine progression, and 4—companion diagnostics for determining therapy, although the results of such methods are not so limited.

The following examples are intended to illustrate the techniques, devices, and systems described above. They are not intended to be limiting.

Example 1: A method comprises determining a magnetic field transmission characteristic corresponding to each type of magnetic nanowire (MNW) of a plurality of types of MNWs; determining a ferromagnetic resonance (FMR) characteristic of each type of MNW of the plurality of types of MNWs, wherein each type of MNW has an FMR characteristic that differs from an FMR characteristic of each other type of MNW of the plurality of types of MNWs; identifying each type of MNW of the plurality of types of MNWs based on the corresponding magnetic field transmission characteristic and the corresponding FMR characteristic; and associating each type of MNW of the plurality of MNWs with a corresponding object of a plurality of objects, wherein each object differs from at least one other object of the plurality of objects.

Example 2: In Example 1, the composition of each type of MNW of the plurality of types of MNWs comprises at least one of cobalt, iron, nickel, copper, or gold.

Example 3: In Example 1 or 2, at least one type of MNW of the plurality of MNW comprises a plurality of segments, wherein a first segment of the plurality of segments comprises a first material being ferromagnetic and a second segment of the plurality of segments comprises a second material different from the first material.

Example 4: In Example 3, the first segment and the second segment are adjacent to one another.

Example 5: In Example 3, at least two segments of the plurality of segments have different dimensions.

Example 6: In any of Examples 1-5, determining the FMR characteristic of each type of MNW of the plurality of types of MNWs comprises, for each type of MNW: applying a magnetic field to the type of MNW; directing a first radio frequency signal to the type of MNW while the type of MNW is subject to the magnetic field; detecting a second radio frequency signal resulting from the first radio frequency signal passing by the type of MNW, wherein a difference between the first radio frequency signal and the second radio frequency signal corresponds to a radio frequency absorption of the type of MNW; identifying at least one of a strength of the magnetic field or a frequency of the first radio frequency signal at which the radio frequency absorption of the type of MNW satisfies a threshold absorption value (e.g., an absorption value that indicates that FMR has occurred) that corresponds to FMR of the type of MNW; and determining the FMR characteristic of the type of MNW as being the at least one of the strength of the magnetic field or the frequency of the first radio frequency signal that corresponds to the FMR of the type of MNW.

Example 7: In Example 6, the strength of the magnetic field or the frequency of the first radio frequency signal at which the radio frequency absorption of the type of MNW satisfies the threshold absorption value is a first strength of the magnetic field or a first frequency of the first radio frequency signal, the method further comprising: identifying at least one of a second strength of the magnetic field or a second frequency of the first radio frequency signal at which the radio frequency absorption of the type of MNW satisfies the threshold absorption value; and determining the FMR characteristic of the type of MNW as further being the at least one of the second strength of the magnetic field or the second frequency of the first radio frequency signal that corresponds to the FMR of the type of MNW.

Example 8: In any of Examples 1-7, the method further comprises manufacturing the plurality of types of MNWs, wherein at least one of a composition or a dimension of each type of MNW of the plurality of types of MNWs differs from at least one of a composition or a dimension of each other type of MNW of the plurality of types of MNWs.

Example 9: In any of Examples 1-8, at least one of a composition or a dimension of each type of MNW of the plurality of types of MNWs differs from at least one of a composition or a dimension of each other type of MNW of the plurality of types of MNWs.

Example 10: In any of Examples 1-9, an object of the plurality of objects comprises one of an article of manufacture or a chemical composition, and associating a type of MNW of the plurality of MNWs with the object comprises incorporating the type of MNW into a material of the one of the article of manufacture or the chemical composition or attaching the type of MNW to the one of the article of manufacture or the chemical composition.

Example 11: In any of Examples 1-10, an object of the plurality of objects comprises an organism, and wherein associating a type of MNW of the plurality of MNWs with the object comprises introducing the type of MNW into the organism or attaching the type of MNW to the organism.

Example 12: In Example 11, the type of MNW of the plurality of types of MNWs comprises a core of a ferromagnetic material and a biocompatible coating disposed at least partially external from the core.

Example 13: In Example 12, the type of MNW of the plurality of types of MNWs further comprises a biologically-active compound attached to an outer surface of the biocompatible coating, and the biologically-active compound is configured to biochemically interact with a selected cell type within the organism.

Example 14: A system comprises a memory; and processing circuitry configured to: receive, from a remote computer, data representative of a magnetic field transmission characteristic corresponding to each type of magnetic nanowire (MNW) of a plurality of types of MNWs; receive, from the remote computer, data representative of a ferromagnetic resonance (FMR) characteristic of each type of MNW of the plurality of types of MNWs, wherein each type of MNW has an FMR characteristic that differs from an FMR characteristic of each other type of MNW of the plurality of types of MNWs; identify each type of MNW of the plurality of types of MNWs based on the corresponding magnetic field transmission characteristic and the corresponding FMR characteristic; and associate, in the memory, each type of MNW of the plurality of MNWs with a corresponding object of a plurality of objects, wherein each object differs from at least one other object of the plurality of objects.

Example 15: In Example 14, the composition of each type of MNW of the plurality of types of MNWs comprises at least one of cobalt, iron, nickel, copper, or gold.

Example 16: In Example 14 or 15 at least one type of MNW of the plurality of MNW comprises a plurality of segments, wherein a first segment of the plurality of segments comprises a first material being ferromagnetic and a second segment of the plurality of segments comprises a second material different from the first material.

Example 17: In Example 16, the first segment and the second segment are adjacent to one another.

Example 18: In Example 16, at least two segments of the plurality of segments have different dimensions.

Example 19: In any of Examples 14-18, the system further comprises an electromagnet configured to, for each type of MNW of the plurality of MNWs, apply a magnetic field to the type of MNW; and a vector network analyzer (VNA) configured to, for each type of MNW of the plurality of MNWs, direct a first radio frequency signal to the type of MNW while the type of MNW is subject to the magnetic field, wherein the processing circuitry is configured to determine the FMR characteristic of each type of MNW of the plurality of MNWs by at least, for each type of MNW: receiving, from the remote computer, data representative of a second radio frequency signal resulting from the first radio frequency signal passing by the type of MNW, wherein a difference between the first radio frequency signal and the second radio frequency signal corresponds to a radio frequency absorption of the type of MNW; identifying at least one of a strength of the magnetic field or a frequency of the first radio frequency signal at which the radio frequency absorption of the type of MNW satisfies a threshold absorption value that corresponds to FMR of the type of MNW; and determining the FMR characteristic of the type of MNW as being the at least one of the strength of the magnetic field or the frequency of the first radio frequency signal that corresponds to the FMR of the type of MNW.

Example 20: In Example 19, the strength of the magnetic field or the frequency of the first radio frequency signal at which the radio frequency absorption of the type of MNW satisfies the threshold absorption value is a first strength of the magnetic field or a first frequency of the first radio frequency signal, wherein the processing circuitry is further configured to: identify at least one of a second strength of the magnetic field or a second frequency of the first radio frequency signal at which the radio frequency absorption of the type of MNW satisfies the threshold absorption value; and determine the FMR characteristic of the type of MNW as further being the at least one of the second strength of the magnetic field or the second frequency of the first radio frequency signal that corresponds to the FMR of the type of MNW.

Example 21: In any of Example 14-20, at least one of a composition or a dimension of each type of MNW of the plurality of types of MNWs differs from at least one of a composition or a dimension of each other type of MNW of the plurality of types of MNWs.

Example 22: In any of Examples 14-21, an object of the plurality of objects comprises one of an article of manufacture or a chemical composition, and wherein a type of MNW of the plurality of MNWs corresponds to the one of the article of manufacture or the chemical composition by at least being incorporated into a material of the one of the article of manufacture or the chemical composition or being attached to the one of the article of manufacture or the chemical composition.

Example 23: In any of Examples 14-22, an object of the plurality of objects comprises an organism, and wherein a type of MNW of the plurality of MNWs corresponds to the object by at least being introduced into the organism or being attached to the organism.

Example 24: In Example 23, the type of MNW of the plurality of types of MNWs comprises a core of a ferromagnetic material and a biocompatible coating disposed at least partially external from the core.

Example 25: In Example 24, the type of MNW of the plurality of types of MNWs further comprises a biologically-active compound attached to an outer surface of the biocompatible coating, and wherein the biologically-active compound is configured to biochemically interact with a selected cell type within the organism.

Example 26: A non-transitory computer-readable storage medium comprising instructions that, when executed by processing circuitry, cause the processing circuitry to: receive, from a remote computer, data representative of a magnetic field transmission characteristic corresponding to each type of magnetic nanowire (MNW) of a plurality of types of MNWs; receive, from the remote computer, data representative of a ferromagnetic resonance (FMR) characteristic of each type of MNW of the plurality of types of MNWs, wherein each type of MNW has an FMR characteristic that differs from an FMR characteristic of each other type of MNW of the plurality of types of MNWs; identify each type of MNW of the plurality of types of MNWs based on the corresponding magnetic field transmission characteristic and the corresponding FMR characteristic; and associate, in a memory, each type of MNW of the plurality of MNWs with a corresponding object of a plurality of objects, wherein each object differs from at least one other object of the plurality of objects.

Example 27: In Example 26, the composition of each type of MNW of the plurality of types of MNWs comprises at least one of cobalt, iron, nickel, copper, or gold.

Example 28: In Example 26 or 27, at least one type of MNW of the plurality of MNW comprises a plurality of segments, wherein a first segment of the plurality of segments comprises a first material being ferromagnetic and a second segment of the plurality of segments comprises a second material different from the first material.

Example 29: In Example 28, the first segment and the second segment are adjacent to one another.

Example 30: In Example 28 or 29, at least two segments of the plurality of segments have different dimensions.

Example 31: In any of Examples 26-30, the instructions, when executed by processing circuitry, further cause the processing circuitry to, for each type of MNW of the plurality of types of MNWs: receive, from the remote computer, data representative of a magnetic field applied to the type of MNW; receive, from the remote computer, data representative of a first radio frequency signal directed to the type of MNW while the type of MNW is subject to the magnetic field; receive, from the remote computer, data representative of a second radio frequency signal resulting from the first radio frequency signal passing by the type of MNW, wherein a difference between the first radio frequency signal and the second radio frequency signal corresponds to a radio frequency absorption of the type of MNW; identify at least one of a strength of the magnetic field or a frequency of the first radio frequency signal at which the radio frequency absorption of the type of MNW satisfies a threshold absorption value that corresponds to FMR of the type of MNW; and determine the FMR characteristic of the type of MNW as being the at least one of the strength of the magnetic field or the frequency of the first radio frequency signal that corresponds to the FMR of the type of MNW.

Example 32: In Example 31, the strength of the magnetic field or the frequency of the first radio frequency signal at which the radio frequency absorption of the type of MNW satisfies the threshold absorption value is a first strength of the magnetic field or a first frequency of the first radio frequency signal, wherein the processing circuitry is further configured to: identify at least one of a second strength of the magnetic field or a second frequency of the first radio frequency signal at which the radio frequency absorption of the type of MNW satisfies the threshold absorption value; and determine the FMR characteristic of the type of MNW as further being the at least one of the second strength of the magnetic field or the second frequency of the first radio frequency signal that corresponds to the FMR of the type of MNW.

Example 33: In any of Examples 26-32, at least one of a composition or a dimension of each type of MNW of the plurality of types of MNWs differs from at least one of a composition or a dimension of each other type of MNW of the plurality of types of MNWs.

Example 34: In any of Examples 26-33, an object of the plurality of objects comprises one of an article of manufacture or a chemical composition, and wherein a type of MNW of the plurality of MNWs corresponds to the one of the article of manufacture or the chemical composition by at least being incorporated into a material of the one of the article of manufacture or the chemical composition or being attached to the one of the article of manufacture or the chemical composition.

Example 35: In any of Examples 26-34, an object of the plurality of objects comprises an organism, and wherein a type of MNW of the plurality of MNWs corresponds to the object by at least being introduced into the organism or being attached to the organism.

Example 36: In Example 35, the type of MNW of the plurality of types of MNWs comprises a core of a ferromagnetic material and a biocompatible coating disposed at least partially external from the core.

Example 37: In Example 36, the type of MNW of the plurality of types of MNWs further comprises a biologically-active compound attached to an outer surface of the biocompatible coating, and wherein the biologically-active compound is configured to biochemically interact with a selected cell type within the organism.

Example 38: A method comprising receiving, by processing circuitry, data representative of a ferromagnetic resonance (FMR) characteristic of each type of magnetic nanowire (MNW) of a plurality of types of MNWs, wherein each type of MNW has an FMR characteristic that differs from an FMR characteristic of each other type of MNW of the plurality of types of MNWs; receiving, by the processing circuitry, data representative of an FMR scan of an object, the FMR scan comprising an application of a magnetic field to the object; determining, by the processing circuitry, a magnetic field transmission characteristic of the object based on the data; identifying, by the processing circuitry, one or more types of MNWs of the plurality of types of MNWs associated with the object based on the magnetic field transmission characteristic of the object; and identifying, by the processing circuitry, the object based on the one or more types of MNWs identified based on the magnetic field transmission characteristic of the object.

Example 39: In Example 38, the method further comprises conducting the FMR scan of the object by at least: applying the magnetic field to the object; directing a first radio frequency signal toward the object while the object is subject to the magnetic field; detecting a second radio frequency signal resulting from the first radio frequency signal passing by the object; generating data representative of the second radio frequency signal; and transmitting, to the processing circuitry, the data representative of the second radio frequency signal.

Example 40: In Example 39, identifying the object based on the one or more types of the MNWs identified by the magnetic field transmission characteristic of the object comprises: comparing, by the processing circuitry, the magnetic field transmission characteristic of the object to respective FMR characteristics of the at least one type of MNW of the plurality of MNWs; and identifying the object based on the comparison.

Example 41: In any of Examples 38-40, the composition of each type of MNW of the plurality of types of MNWs comprises at least one of cobalt, iron, nickel, copper, or gold.

Example 42: In any of Examples 38-41, at least one type of MNW of the plurality of MNW comprises a plurality of segments, wherein a first segment of the plurality of segments comprises a first material being ferromagnetic and a second segment of the plurality of segments comprises a second material different from the first material.

Example 43: In Example 42, the first segment and the second segment are adjacent to one another.

Example 44: In Example 42 or 43, at least two segments of the plurality of segments have different dimensions.

Example 45: In any of Examples 38-44, the object comprises a chemical composition, an article of manufacture, or an organism, and wherein the type of MNW associated with the object is one of incorporated into a material of the object or attached to the object.

Example 46: In Example 45, the object comprises the organism, and wherein the type of MNW comprises a core of a ferromagnetic material and a biocompatible coating disposed at least partially external from the core.

Example 47: In Example 45 or 46, the type of MNW further comprises a biologically-active compound attached to an outer surface of the biocompatible coating, wherein the biologically-active compound is configured to biochemically interact with a selected cell type within the organism.

Example 48: A system comprising: a memory; and processing circuitry configured to: receive, from a remote computer, data representative of a ferromagnetic resonance (FMR) characteristic of each type of magnetic nanowire (MNW) of a plurality of types of MNWs, wherein each type of MNW has an FMR characteristic that differs from an FMR characteristic of each other type of MNW of the plurality of types of MNWs; store the data representative of the FMR characteristic of each type of MNW of the plurality of types of MNW in the memory; receive, from a remote computer, data representative of an FMR scan of an object, the FMR scan comprising an application of a magnetic field to the object; determine a magnetic field transmission characteristic of the object based on the data; identify one or more types of MNWs of the plurality of types of MNWs associated with the object based on the magnetic field transmission characteristic of the object; and identify the object based on the one or more types of MNWs identified based on the magnetic field transmission characteristic of the object.

Example 49: In Example 48, the processing circuitry is a first processing circuitry and the remote computer comprises a second processing circuitry, the system further comprising a plurality of components configured to conduct the FMR scan, the plurality of components comprising: an electromagnet configured to apply the magnetic field to the object; a vector network analyzer (VNA) configured to direct a first radio frequency signal toward the object while the object is subject to the magnetic field, wherein the second processing circuitry is configured to: detect a second radio frequency signal resulting from the first radio frequency signal passing by the object; generate data representative of the second radio frequency signal; and instruct communication circuitry of the remote computer to transmit the data representative of the second radio frequency signal to the first processing circuitry.

Example 50: In Example 49, the first processing circuitry is configured to identify the object based on the one or more types of the MNWs identified by the magnetic field transmission characteristic of the object by at least: comparing the magnetic field transmission characteristic of the object to respective FMR characteristics of the at least one type of MNW of the plurality of MNWs; and identifying the object based on the comparison.

Example 51: In any of Examples 48-50, the composition of each type of MNW of the plurality of types of MNWs comprises at least one of cobalt, iron, nickel, copper, or gold.

Example 52: In any of Examples 48-51, at least one type of MNW of the plurality of MNW comprises a plurality of segments, wherein a first segment of the plurality of segments comprises a first material being ferromagnetic and a second segment of the plurality of segments comprises a second material different from the first material.

Example 53: In Example 52, the first and the second segment are adjacent to one another.

Example 54: In Example 52 or 53, at least two segments of the plurality of segments have different dimensions.

Example 55: In any of Examples 48-54, the object comprises a chemical composition, an article of manufacture, or an organism, wherein the type of MNW associated with the object is one of incorporated into a material of the object or attached to the object.

Example 56: In Example 55, the object comprises the organism, and wherein the type of MNW comprises a core of a ferromagnetic material and a biocompatible coating disposed at least partially external from the core.

Example 57: In Example 55 or 56, the type of MNW further comprises a biologically-active compound attached to an outer surface of the biocompatible coating, wherein the biologically-active compound is configured to biochemically interact with a selected cell type within the organism.

Example 58: A non-transitory computer-readable storage medium comprising instructions that, when executed by processing circuitry, cause the processing circuitry to: receive, from a remote computer, data representative of a ferromagnetic resonance (FMR) characteristic of each type of magnetic nanowire (MNW) of a plurality of types of MNWs, wherein each type of MNW has an FMR characteristic that differs from an FMR characteristic of each other type of MNW of the plurality of types of MNWs; receive, from the remote computer, data representative of an FMR scan of an object, the FMR scan comprising an application of a magnetic field to the object; determine a magnetic field transmission characteristic of the object based on the data; identify one or more types of MNWs of the plurality of types of MNWs associated with the object based on the magnetic field transmission characteristic of the object; and identify the object based on the one or more types of MNWs identified based on the magnetic field transmission characteristic of the object.

Example 59: In Example 58, the processing circuitry is a first processing circuitry and the remote computer comprises a second processing circuitry, and wherein the instructions, when executed by first processing circuitry, cause the first processing circuitry to receive, from the remote computer, data representative of an FMR scan of the object by at least: receiving, from the remote computer, data representative of the magnetic field applied to the object; and receiving, from the remote computer, data representative of a first radio frequency signal directed to the object while the object is subject to the magnetic field; wherein the second processing circuitry is configured to: detect a second radio frequency signal resulting from the first radio frequency signal passing by the object; generate data representative of the second radio frequency signal; and instruct communication circuitry of the remote computer to transmit the data representative of the second radio frequency signal to the first processing circuitry.

Example 60: In Example 59, the instructions, when executed by first processing circuitry, cause the first processing circuitry to identify the object based on the one or more types of the MNWs identified by the magnetic field transmission characteristic of the object by at least: comparing the magnetic field transmission characteristic of the object to respective FMR characteristics of the at least one type of MNW of the plurality of MNWs; and identifying the object based on the comparison.

Example 61: In any of Examples 58-60, the composition of each type of MNW of the plurality of types of MNWs comprises at least one of cobalt, iron, nickel, copper, or gold.

Example 62: In any of Examples 58-61, at least one type of MNW of the plurality of MNW comprises a plurality of segments, wherein a first segment of the plurality of segments comprises a first material being ferromagnetic and a second segment of the plurality of segments comprises a second material different from the first material.

Example 63: In Example 62, the first segment and the second segment are adjacent to one another.

Example 64: In Example 62 or 63, at least two segments of the plurality of segments have different dimensions.

Example 65: In any of Examples 58-64, the object comprises a chemical composition, an article of manufacture, or an organism, and wherein the type of MNW associated with the object is one of incorporated into a material of the object or attached to the object.

Example 66: In Example 65, the object comprises the organism, and wherein the type of MNW comprises a core of a ferromagnetic material and a biocompatible coating disposed at least partially external from the core.

Example 67: In Example 65 or 66, the type of MNW further comprises a biologically-active compound attached to an outer surface of the biocompatible coating, wherein the biologically-active compound is configured to biochemically interact with a selected cell type within the organism.

Example 68: A method comprising: receiving, by processing circuitry, data representative of a ferromagnetic resonance (FMR) characteristic of each type of magnetic nanowire (MNW) of a plurality of types of MNWs, wherein each type of MNW of the plurality of types of MNW comprises a respective composition different from compositions of other types of MNWs of the plurality of types of MNWs, and wherein the respective FMR characteristic of each type of MNW of the plurality of types of MNWs differs from FMR characteristics of other types of MNWs of the plurality of types of MNWs; receiving, by the processing circuitry, data representative of an FMR scan of a sample containing at least two types of MNWs of the plurality of types of MNWs, the FMR scan comprising an application of a magnetic field to the sample; determining, by the processing circuitry, a magnetic field transmission characteristic of the sample based on the data, wherein the magnetic field transmission characteristic of the sample corresponds to a combination of the respective FMR characteristics of the at least two types of MNWs contained in the sample; and identifying, by the processing circuitry, each of the at least two types of MNW of the plurality of types of MNWs contained in the sample based on the magnetic field transmission characteristic of the sample and the FMR characteristics corresponding to the plurality of types of MNWs.

Example 69: In Example 68, identifying each of the at least two types of MNWs of the plurality of types of MNWs contained in the sample based on the magnetic field transmission characteristic of the sample and the FMR characteristics corresponding to the plurality of types of MNWs comprises: comparing, by the processing circuitry, the magnetic field transmission characteristic of the sample to respective FMR characteristics of at least two types of MNWs of the plurality of MNWs; and identifying each of the at least two types of MNWs based on the comparison.

Example 70: In Example 68 or 69, the method further comprises conducting the FMR scan of the object by at least: applying the magnetic field to the sample; directing a first radio frequency signal toward the sample while the sample is subject to the magnetic field; detecting a second radio frequency signal resulting from the first radio frequency signal passing by the sample; generating data representative of the second radio frequency signal; and transmitting, to the processing circuitry, the data representative of the second radio frequency signal.

Example 71: In any of Examples 68-70, the composition of each type of MNW of the plurality of types of MNWs comprises at least one of cobalt, iron, nickel, copper, or gold.

Example 72: In any of Examples 68-71, at least one type of MNW of the plurality of MNW comprises a plurality of segments, wherein a first segment of the plurality of segments comprises a first material being ferromagnetic and a second segment of the plurality of segments comprises a second material different from the first material.

Example 73: In Example 72, the first segment and the second segment are adjacent to one another.

Example 74: In Example 72 or 73, at least two segments of the plurality of segments have different dimensions.

Example 75: A system comprising a memory; and processing circuitry configured to: receive, from a remote computer, data representative of a ferromagnetic resonance (FMR) characteristic of each type of magnetic nanowire (MNW) of a plurality of types of MNWs, wherein each type of MNW of the plurality of types of MNW comprises a respective composition different from compositions of other types of MNWs of the plurality of types of MNWs, and wherein the respective FMR characteristic of each type of MNW of the plurality of types of MNWs differs from FMR characteristics of other types of MNWs of the plurality of types of MNWs; store the data representative of the FMR characteristic of each type of MNW of a plurality of types of MNWs in the memory; receive, from the remote computer, data representative of an FMR scan of a sample containing at least two types of MNWs of the plurality of types of MNWs, the FMR scan comprising an application of a magnetic field to the sample; determine a magnetic field transmission characteristic of the sample based on the data, wherein the magnetic field transmission characteristic of the sample corresponds to a combination of the respective FMR characteristics of the at least two types of MNWs contained in the sample; and identify each of the at least two types of MNW of the plurality of types of MNWs contained in the sample based on the magnetic field transmission characteristic of the sample and the FMR characteristics corresponding to the plurality of types of MNWs.

Example 76: In Example 75, the processing circuitry is configured to identify each of the at least two types of MNWs of the plurality of types of MNWs contained in the sample based on the magnetic field transmission characteristic of the sample and the FMR characteristics corresponding to the plurality of types of MNWs by at least: comparing the magnetic field transmission characteristic of the sample to respective FMR characteristics of at least two types of MNWs of the plurality of MNWs; and identifying each of the at least two types of MNWs based on the comparison.

Example 77: In Example 75 or 76, the processing circuitry is a first processing circuitry and the remote computer comprises a second processing circuitry, the system further comprising a plurality of components configured to conduct the FMR scan, the plurality of components comprising: an electromagnet configured to apply the magnetic field to the sample; a vector network analyzer (VNA) configured to direct a first radio frequency signal toward the sample while the sample is subject to the magnetic field, wherein the second processing circuitry is configured to: detect a second radio frequency signal resulting from the first radio frequency signal passing by the sample; generate data representative of the second radio frequency signal; and instruct communication circuitry of the remote computer to transmit the data representative of the second radio frequency signal to the first processing circuitry.

Example 78: In any of Examples 75-77, the composition of each type of MNW of the plurality of types of MNWs comprises at least one of cobalt, iron, nickel, copper, or gold.

Example 79: In any of Examples 75-78, at least one type of MNW of the plurality of MNW comprises a plurality of segments, wherein a first segment of the plurality of segments comprises a first material being ferromagnetic and a second segment of the plurality of segments comprises a second material different from the first material.

Example 80: In Example 79, the first segment and the second segment are adjacent to one another.

Example 81: In Example 79 or 80, at least two segments of the plurality of segments have different dimensions.

Example 82: A non-transitory computer-readable storage medium comprising instructions that, when executed by processing circuitry, cause the processing circuitry to: receive, from a remote computer, data representative of a ferromagnetic resonance (FMR) characteristic of each type of magnetic nanowire (MNW) of a plurality of types of MNWs, wherein each type of MNW of the plurality of types of MNW comprises a respective composition different from compositions of other types of MNWs of the plurality of types of MNWs, and wherein the respective FMR characteristic of each type of MNW of the plurality of types of MNWs differs from FMR characteristics of other types of MNWs of the plurality of types of MNWs; receive, from the remote computer, data representative of an FMR scan of a sample containing at least two types of MNWs of the plurality of types of MNWs, the FMR scan comprising an application of a magnetic field to the sample; determine a magnetic field transmission characteristic of the sample based on the data, wherein the magnetic field transmission characteristic of the sample corresponds to a combination of the respective FMR characteristics of the at least two types of MNWs contained in the sample; and identify each of the at least two types of MNW of the plurality of types of MNWs contained in the sample based on the magnetic field transmission characteristic of the sample and the FMR characteristics corresponding to the plurality of types of MNWs.

Example 83: In Example 82, the instructions, when executed by processing circuitry, cause the processing circuitry to identify each of the at least two types of MNWs of the plurality of types of MNWs contained in the sample based on the magnetic field transmission characteristic of the sample and the FMR characteristics corresponding to the plurality of types of MNWs by at least: comparing the magnetic field transmission characteristic of the sample to respective FMR characteristics of at least two types of MNWs of the plurality of MNWs; and identifying each of the at least two types of MNWs based on the comparison.

Example 84: In Example 82 or 83, the processing circuitry is a first processing circuitry and the remote computer comprises a second processing circuitry, and wherein the instructions, when executed by first processing circuitry, cause the first processing circuitry to receive, from the remote computer, data representative of an FMR scan of the sample by at least: receiving, from the remote computer, data representative of the magnetic field applied to the sample; and receiving, from the remote computer, data representative of a first radio frequency signal directed to the sample while the sample is subject to the magnetic field, wherein the second processing circuitry is configured to: detect a second radio frequency signal resulting from the first radio frequency signal passing by the object; generate data representative of the second radio frequency signal; and instruct communication circuitry of the remote computer to transmit the data representative of the second radio frequency signal to the first processing circuitry.

Example 85: In any of Examples 82-84, the composition of each type of MNW of the plurality of types of MNWs comprises at least one of cobalt, iron, nickel, copper, or gold.

Example 86: In any of Examples 82-85, at least one type of MNW of the plurality of MNW comprises a plurality of segments, wherein a first segment of the plurality of segments comprises a first material being ferromagnetic and a second segment of the plurality of segments comprises a second material different from the first material.

Example 87: In Example 86, the first segment and the second segment are adjacent to one another.

Example 88: In Example 86 or 87, at least two segments of the plurality of segments have different dimensions.

Example 89: A method, comprising: introducing a plurality of magnetic nanowires (MNWs) into one or more cells; introducing the one or more cells into a body of a host organism; obtaining a plurality of exosomes from a sample of bodily fluid from the host organism; isolating, from the plurality of exosomes, one or more exosomes that each contain one or more MNWs of the plurality of MNWs; and determining that the sample of bodily fluid contains a biomarker indicative of a biological status based on the presence of the one or more exosomes isolated from the plurality of exosomes that each contain the one or more MNWs of the plurality of MNWs.

Example 90: In Example 89, the plurality of MNWs comprises a plurality of types of MNWs, wherein each type of MNW of the plurality of types of MNW comprises a respective composition different from compositions of other types of MNWs of the plurality of types of MNWs, and wherein the respective FMR characteristic of each type of MNW of the plurality of types of MNWs differs from FMR characteristics of other types of MNWs of the plurality of types of MNWs, the method further comprising identifying each of the one or more types of MNWs of the plurality of MNWs contained within the one or more exosomes.

Example 91: In Example 90, the method further comprises: conducting an FMR scan of the one or more exosomes by at least: applying a magnetic field to the one or more exosomes; directing a first radio frequency signal toward the one or more exosomes while the one or more exosomes are subject to the magnetic field; and detecting a second radio frequency signal resulting from the first radio frequency signal passing by the object; and determining a magnetic field transmission characteristic of the one or more exosomes based on the FMR scan, wherein identifying each of the one or more types of MNWs contained in the one or more exosomes comprises: comparing the magnetic field transmission characteristic of the one or more exosomes to respective FMR characteristics of one or more types of MNWs of the plurality of MNWs; and identifying each of the one or more types of MNWs based on the comparison.

Example 92: In Example 90 or 91, the one or more cells comprise a plurality of cell types and wherein each of the types of MNWs of the plurality of types of MNWs corresponds to a cell type of the host organism, the method further comprising identifying at least one cell type contained within in the sample of bodily fluid based on the identity of each of the one or more types of MNWs contained within the one or more exosomes.

Example 93: In any of Examples 89-92, the biological status is associated with one of a presence, absence, or stage of a health condition.

Example 94: In any of Examples 90-93, the composition of each type of MNW of the plurality of types of MNWs comprises cobalt, iron, nickel, copper, or gold.

Example 95: In any of Examples 90-94, at least one type of MNW of the plurality of MNW comprises a plurality of segments, wherein a first segment of the plurality of segments comprises a first material being ferromagnetic and a second segment of the plurality of segments comprises a second material different from the first material.

Example 96: In Example 95, the first segment and the second segment are adjacent to one another.

Example 97: In Example 95 or 96, at least two segments of the plurality of segments have different dimensions.

Example 98: In any of Examples 90-97, at least one type of MNW of the plurality of types of MNWs comprises a core of a ferromagnetic material and a biocompatible coating disposed at least partially external to the core.

Example 99: In Example 98, the at least one type of MNW further comprises a biologically-active compound attached to an outer surface of the biocompatible coating, wherein the biologically-active compound is configured to biochemically interact with a selected cell type within the organism.

Example 100: A method, comprising receiving, by processing circuitry, data representative of a ferromagnetic resonance (FMR) characteristic of each type of magnetic nanowire (MNW) of a plurality of types of MNWs, wherein each type of MNW has an FMR characteristic that differs from an FMR characteristic of each other type of MNW of the plurality of types of MNWs; receiving, by the processing circuitry, data representative of a magnetic field transmission characteristic of a sample containing at least two types of MNWs, and identifying, by the processing circuitry, each of the at least two types of MNW of the plurality of types of MNWs contained in the sample based on the magnetic field transmission characteristic of the sample and the FMR characteristics corresponding to the plurality of types of MNWs, wherein identifying each of the at least two types of MNW of the plurality of types of MNWs contained within the sample comprises: setting the magnetic field transmission characteristic of the sample as $S_{21}$ in Equation 4; fitting Equation 4 to the $S_{21}$ of the sample by at least sequentially setting the FMR characteristic of each type of MNW of the plurality of MNWs as one or more of $M_{eff,k}$ and $H_{eff,k}$ in Equation 4; extracting the coefficient ck for at least two types of MNW of the plurality of MNWs; determining, based on the extracted coefficient ck of the at least two types of MNW of the plurality of MNWs, whether ck is significant; and identifying at least two types of MNWs of the plurality of types of MNWs for which ck is significant as the at least two types of MNWs of the plurality of types of MNWs contained within the sample.

The techniques described in this disclosure may be implemented, at least in part, in hardware, software, firmware or any combination thereof. For example, various aspects of the described techniques may be implemented within one or more processors or processing circuitry, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, circuits or components may be implemented together or separately as discrete but interoperable logic devices. Depiction of different features as circuits or units is intended to highlight different functional aspects and does not necessarily imply that such circuits or units must be realized by separate hardware or software components. Rather, functionality associated with one or more circuits or units may be performed by separate hardware or software components or integrated within common or separate hardware or software components.

The techniques described in this disclosure may also be embodied or encoded in a computer-readable medium, such as a computer-readable storage medium, containing instructions that may be described as non-transitory media. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various aspects of the disclosure have been described. These and other aspects are within the scope of the following claims.

What is claimed is:

1. A method comprising:
    applying a magnetic field to an identification tag comprising a plurality of magnetic nanowires (MNWs);
    directing a first radio frequency signal to the identification tag comprising the plurality of MNWs while the identification tag is subject to the magnetic field;
    detecting absorption of a radio frequency resulting from the first radio frequency signal passing by the plurality of MNWs of the identification tag;
    determining, based on the radio frequency absorption, a ferromagnetic resonance (FMR) characteristic of the plurality of MNWs of the identification tag; and
    identifying, based on the FMR characteristic, a presence of the plurality of MNWs of the identification tag.

2. The method of claim 1, wherein the composition of the plurality of MNWs comprises at least one of cobalt, iron, nickel, copper, or gold.

3. The method of claim 1, wherein each wire of the plurality of MNWs comprises a plurality of segments, wherein a first segment of the plurality of segments comprises a first material being ferromagnetic and a second segment of the plurality of segments comprises a second material different from the first material.

4. The method of claim 3, wherein at least one of: the first segment and the second segment are adjacent to one another, or at least two segments of the plurality of segments have different dimensions.

5. The method of claim 1, wherein determining the FMR characteristic of the plurality of MNWs comprises:
    identifying at least one of a strength of the magnetic field or a frequency of the first radio frequency signal at which the radio frequency absorption of the plurality of MNWs satisfies a threshold absorption value that corresponds to FMR of the plurality of MNWs; and determining the FMR characteristic of the plurality of MNWs as being the at least one of the strength of the magnetic field or the frequency of the first radio frequency signal that corresponds to the FMR of the plurality of MNWs.

6. The method of claim 5, wherein the strength of the magnetic field or the frequency of the first radio frequency signal at which the radio frequency absorption of the plurality of MNWs satisfies the threshold absorption value is a first strength of the magnetic field or a first frequency of the first radio frequency signal, the method further comprising:
identifying at least one of a second strength of the magnetic field or a second frequency of the first radio frequency signal at which the radio frequency absorption of the plurality of MNWs satisfies the threshold absorption value; and
determining the FMR characteristic of the plurality of MNWs as further being the at least one of the second strength of the magnetic field or the second frequency of the first radio frequency signal that corresponds to the FMR of the plurality of MNWs.

7. The method of claim 1, further comprising:
determining a difference between the first radio frequency signal and a second radio frequency signal detected as a result of the first radio frequency signal passing by the plurality of MNWs of the identification tag; and
determining the radio frequency absorption based on the difference.

8. The method of claim 1, wherein:
the identification tag is a first identification tag,
the plurality of MNWs are a first type of MNWs different from other types of MNWs,
the FMR characteristic of the first type of MNWs is a first FMR characteristic different from other FMR characteristics of the other types of MNWs associated with respective identification tags, and
identifying the presences of the first type of MNWs of the identification tag comprises differentiating the first type of MNWs from the other types of MNWs based on detecting the first FMR characteristic instead of the other FMR characteristics of the other types of MNWs.

9. The method of claim 8, wherein at least one of a composition or a dimension of the first type of MNWs differs from at least one of a composition or a dimension of the other type of MNWs.

10. A system comprising:
a memory; and
processing circuitry configured to:
receive data representative of an absorption of a radio frequency resulting from a first radio frequency signal passing by a plurality of magnetic nanowires (MNWs) of an identification tag while the identification tag is subject to a magnetic field;
determine, based on the radio frequency absorption, a ferromagnetic resonance (FMR) characteristic of the plurality of types of MNWs of the identification tag; and
identify, based on the FMR characteristic, a presence of the plurality of MNWs of the identification tag.

11. The system of claim 10, further comprising:
a magnet configured to apply the magnetic field to the plurality of MNWs; and
a vector network analyzer (VNA) configured to direct the first radio frequency signal to the plurality of MNWs while the plurality of MNWs is subject to the magnetic field,
wherein the processing circuitry is configured to determine the FMR characteristic of the plurality of MNWs by at least:
identifying at least one of a strength of the magnetic field or a frequency of the first radio frequency signal at which the radio frequency absorption of the plurality of MNWs satisfies a threshold absorption value that corresponds to FMR of the plurality of MNWs; and
determining the FMR characteristic of the plurality of MNWs as being the at least one of the strength of the magnetic field or the frequency of the first radio frequency signal that corresponds to the FMR of the plurality of MNWs.

12. The system of claim 11, wherein the strength of the magnetic field or the frequency of the first radio frequency signal at which the radio frequency absorption of the plurality of MNWs satisfies the threshold absorption value is a first strength of the magnetic field or a first frequency of the first radio frequency signal, wherein the processing circuitry is further configured to:
identify at least one of a second strength of the magnetic field or a second frequency of the first radio frequency signal at which the radio frequency absorption of the plurality of MNWs satisfies the threshold absorption value; and
determine the FMR characteristic of the plurality of MNWs as further being the at least one of the second strength of the magnetic field or the second frequency of the first radio frequency signal that corresponds to the FMR of the plurality of MNWs.

13. The system of claim 10, wherein the composition of the plurality of MNWs comprises at least one of cobalt, iron, nickel, copper, or gold.

14. The system of claim 10, wherein each wire of the plurality of MNWs comprises a plurality of segments, wherein a first segment of the plurality of segments comprises a first material being ferromagnetic and a second segment of the plurality of segments comprises a second material different from the first material.

15. The system of claim 10, wherein the processing circuitry is further configured to:
determine a difference between the first radio frequency signal and a second radio frequency signal detected as a result of the first radio frequency signal passing by the plurality of MNWs of the identification tag; and
determine the radio frequency absorption based on the difference.

16. The system of claim 10, wherein:
the identification tag is a first identification tag,
the plurality of MNWs are a first type of MNWs different from other types of MNWs,
the FMR characteristic of the first type of MNWs is a first FMR characteristic different from other FMR characteristics of the other types of MNWs associated with respective identification tags, and
the processing circuitry is configured to identify the presence of the first type of MNWs of the identification tag by at least differentiating the first type of MNWs from the other types of MNWs based on detecting the first FMR characteristic instead of the other FMR characteristics of the other types of MNWs.

17. The system of claim 16, wherein at least one of a composition or a dimension of the first type of MNWs differs from at least one of a composition or a dimension of the other type of MNWs.

18. An identification tag comprising:
a material; and
a plurality of magnetic nanowires (MNWs) coupled with the material, wherein the plurality of MNWs are configured to transmit a second radio frequency signal resulting from a first radio frequency signal applied to the plurality of MNWs while the plurality of MNWs are subject to a magnetic field, wherein a radio frequency absorption by the plurality of MNWs corresponds to a difference between the first radiofrequency signal and the second radiofrequency signal, and wherein the presence of the plurality of MNWs is identifiable based on a ferromagnetic resonance (FMR) characteristic based on the radio frequency absorption.

19. The identification tag of claim 18, wherein the composition of the plurality of MNWs comprises at least one of cobalt, iron, nickel, copper, or gold.

20. The identification tag of claim 18, wherein each wire of the plurality of MNWs comprises a plurality of segments, wherein a first segment of the plurality of segments comprises a first material being ferromagnetic and a second segment of the plurality of segments comprises a second material different from the first material.

* * * * *

UNITED STATES PATENT AND TRADEMARK OFFICE
CERTIFICATE OF CORRECTION

| | |
|---|---|
| PATENT NO. | : 11,748,583 B2 |
| APPLICATION NO. | : 17/810155 |
| DATED | : September 5, 2023 |
| INVENTOR(S) | : Rhonda R. Franklin et al. |

It is certified that error appears in the above-identified patent and that said Letters Patent is hereby corrected as shown below:

In the Specification

Column 1, Lines 11-12 Please add Paragraph:
--This invention was made with government support under ECCS-1509543 awarded by National Science Foundation. The government has certain rights in the invention.--

Signed and Sealed this
Twenty-eighth Day of May, 2024

*Katherine Kelly Vidal*

Katherine Kelly Vidal
*Director of the United States Patent and Trademark Office*